(12) United States Patent
Hermkens et al.

(10) Patent No.: US 7,737,136 B2
(45) Date of Patent: Jun. 15, 2010

(54) NON-STEROIDAL PROGESTERONE RECEPTOR MODULATORS

(75) Inventors: Pedro Harold Han Hermkens, Oss (NL); Hans Lucas, Oss (NL); Paul Peter Marie Antonius Dols, Oss (NL); Johannes Bernardus Maria Rewinkel, Oss (NL); Brigitte Johanna Bernita Folmer, Oss (NL)

(73) Assignee: N.V. Organon, Oss (NL)

( * ) Notice: Subject to any disclaimer, the term of this patent is extended or adjusted under 35 U.S.C. 154(b) by 1172 days.

(21) Appl. No.: 10/510,275

(22) PCT Filed: Apr. 1, 2003

(86) PCT No.: PCT/EP03/50085

§ 371 (c)(1),
(2), (4) Date: Mar. 11, 2005

(87) PCT Pub. No.: WO03/084963

PCT Pub. Date: Oct. 16, 2003

(65) Prior Publication Data

US 2005/0171087 A1 Aug. 4, 2005

(30) Foreign Application Priority Data

Apr. 4, 2002 (EP) .................................. 02076350

(51) Int. Cl.
*A61P 5/24* (2006.01)
*A61P 35/00* (2006.01)
*A61K 31/55* (2006.01)
*C07D 498/04* (2006.01)
*C07D 513/04* (2006.01)
*C07D 471/04* (2006.01)

(52) U.S. Cl. .................................. 514/211.09; 540/546
(58) Field of Classification Search ............ 514/211.09; 540/546
See application file for complete search history.

(56) References Cited

U.S. PATENT DOCUMENTS

| 3,966,723 A | 6/1976 | van der Burg |
| 4,016,161 A * | 4/1977 | Van der Burg ............. 540/546 |
| 4,054,572 A * | 10/1977 | van der Burg ............. 540/555 |
| 5,688,810 A | 11/1997 | Jones et al. |

FOREIGN PATENT DOCUMENTS

| DE | 2420168 | 4/1974 |
| EP | 0 421 802 A2 | 4/1991 |
| EP | 0 303 306 | 3/1993 |
| EP | 0 876815 | 11/1998 |
| WO | WO 03/084963 | 10/2003 |
| WO | WO 2006/084917 | 8/2006 |
| WO | WO 2008/037746 | 4/2008 |

OTHER PUBLICATIONS

Beato et.al., "DNA Regulatory Elements for Steroid Hormones," *J. Steroid Biochem.* 32 (1989) 737-747.
Caufield, W., "Synthesis of 1-amino-1,2,3,14b-tetrahydro-4H-pyrido[1,2-d]-dibenzo[b,f] [1,4]oxazepine and related compounds", *J. Chem. Soc.*, Perkins Trans. 1, No. 6, pp. 545-553, (1996).
Dijkema, R., et al., "Human Progesterone Receptor A and B Isoforms in CHO cells. I. Stable Transfection of Receptor and Receptor-responsive Reporter Genes: Transcription Modulation by (Anti)progestagens", *J. Steroid Biochem. Biol.*, vol. 64, No. 3-4, pp. 147-156 (1998).
Schoonen, W., et al., "Development of High-Throughput in Vitro Bioassay to Assess Potencies of Progestagenic Compounds Using Chinese Hamster Ovary Cells Stably Transfected with the Human Progesterone Receptor and a Luciferase Reporter System", *Analytical Biochemistry*, vol. 261, pp. 222-224 (1998).
PCT International Search Report dated, Aug. 6, 2003, for corresponding PCT Application No. PCT/EP03/50085.
PCT International Search Report and Written Opinion, dated Aug. 12, 2008, which was issued during the prosecution of International Application No. PCT/EP2008/003714, which is related to the present application.
PCT International Search Report and Written Opinion, dated Dec. 28, 2007, which was issued during the prosecution of International Application No. PCT/EP2007/060225, which is related to the present application.

* cited by examiner

*Primary Examiner*—Brenda L Coleman
(74) *Attorney, Agent, or Firm*—Susan L. Hess

(57) ABSTRACT

The present invention provides compounds according to general Formula (I), a prodrug thereof, a pharmaceutically acceptable salt thereof, or a pharmaceutically acceptable salt of a prodrug thereof. More particularly, the present invention provides high affinity non-steroidal compounds which are agonists, partial agonists or antagonists of the progesterone receptor.

13 Claims, No Drawings

NON-STEROIDAL PROGESTERONE RECEPTOR MODULATORS

This application is a national stage entry under 35 U.S.C. §371 of PCT/EP03/50085, filed Apr. 1, 2003.

The present invention relates to progesterone receptor modulating compounds as well as to the use of these compounds in therapy.

Intracellular receptors are a class of structurally related proteins involved in the regulation of gene proteins. Steroid receptors are a subset of these receptors, including the progesterone receptor (PR), androgen receptor (AR), estrogen receptor (ER), glucocorticoid receptor (GR) and mineralocorticoid receptor (MR). Regulation of a gene by such factors requires the intracellular receptor and a corresponding ligand which has the ability to selectively bind to the receptor in a way that affects gene transcription.

Progesterone receptor modulators (progestagens) are known to play a n important role in the health of women. The natural ligand for the PR receptor is the steroid hormone progesterone, but synthetic compounds have been made which may also serve as ligands (see e.g. Jones et al U.S. Pat. No. 5,688,810).

Progestagens are currently widely used for hormonal contraception and in HRT. Other important clinical applications of progestagens are treatment of gynaecological disorders (e.g. endometriosis, dysmenorrhea, dysfunctional uterine bleeding, severe premenstrual syndrome), breast cancer, and luteal support during IVF. PR agonists are used in birth control formulations, whereas PR antagonists may be used in contraception, hormone dependent cancers, hormone displacement therapy, endometriosis etc.

The current steroidal progestagens have been proven to be quite safe and are well tolerated. Sometimes, however, side effects (e.g. breast tenderness, headaches, depression, and weight gain) have been reported that are attributed to these steroidal progestagens, either alone or in combination with estrogenic compounds.

Steroidal ligands for one receptor often show cross-reactivity with other steroidal receptors. Many progestagens also bind e.g. to the glucocorticoid receptor. Non-steroidal progestagens have no molecular structural similarity with steroids and therefore one might also expect differences in physicochemical properties, pharmacokinetic (PK) parameters, tissue distribution (e.g. CNS versus peripheral) and, more importantly, non-steroidal progestagens may show no/less cross-reactivity to other steroid receptors. Therefore, non-steroidal progestagens will score differently in these respects.

The present invention provides non-steroidal compounds that modulate progesterone receptor activity. More particularly, the present invention provides high affinity non-steroidal compounds which are agonists, partial agonists or antagonists of the progesterone receptor. Preferably these compounds are highly specific for the progesterone receptor. According to the present invention compounds are provided having a general Formula I, a prodrug thereof, or a pharmaceutically acceptable salt of either the compound or the prodrug.

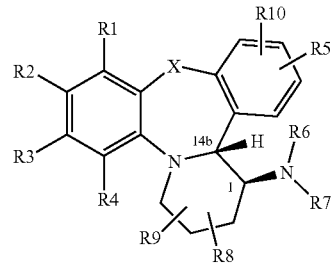

Formula I wherein
R1, R3, R4, R5 and R10 independently are selected from the group consisting of H, halogen, (1-4C)alkyl, (2-4C)alkenyl, (2-4C)alkynyl, OH, CN, O(1-4C)alkyl, $S(O)_m$(1-4C)alkyl (optionally substituted with one or more halogen atoms), C(O)(1-4C)alkyl, OC(O)(1-4C)alkyl and NR19R20, R2 is selected from the group consisting of H, halogen, $NO_2$, NR11R12, (1-4C)alkyl, (2-4C)alkenyl, (2-4C)alkynyl, OH, O(1-4C)alkyl, S(1-4C)alkyl and OC(O)(1-4C)alkyl, R6 is selected from the group consisting of H, C(Y)R15, C(O)OR16, C(S)NR17, (1-6C)alkyl, (1-6C)alkoxy-substituted (1-4C)alkyl and $(CH_2)_n$C(O)OR21, R7 is selected from the group consisting of (1-4C)alkyl, (2-4C)alkenyl and (2-4C)alkynyl, all optionally substituted with one or more halogen atoms or R7 is H.

R8 and R9 independently are selected from the group consisting of H and (1-4C)alkyl, R11 and R12 independently are selected from the group consisting of H, (1-4C)alkyl, (2-4C)alkenyl or (2-4C)alkynyl, (1-6C)alkoxycarbonyl, (1-4C)alkylsulfonyl and (6-10C)arylsulfonyl, R15 is H or R15 is selected from the group consisting of (1-6C)alkyl, (3-6C)cycloalkyl, (2-4C)alkenyl, (2-4C)alkynyl, (6-10C)aryl, 1,4-bisaryl, amino(1-4C)alkyl, hydroxy(1-4C)alkyl, and carboxy(1-4C)alkyl, all optionally substituted with one or more halogen atoms, R16 is (1-6C)alkyl, optionally substituted with one or more halogen atoms, R17 is selected from the group consisting of (1-4C)alkyl, (2-4C)alkenyl, (2-4C)alkynyl and (3-6C)cycloalkyl, all optionally substituted with one or more halogen atoms, X is selected from the group consisting of O, S, $CH_2$ and NR18, Y is selected from the group consisting of O, S, and NH, R18 is selected from the group consisting of H and (1-4C)alkyl, R19 is selected from the group consisting of H and (1-4C)alkyl, R20 is selected from the group consisting of H, (1-4C)alkyl, $CH_2$(6-10C)aryl, C(O)(1-6C)alkyl and C(O)NH(1-4C)alkyl, R21 is selected from the group consisting of H and (1-6C)alkyl, m is 0, 1 or 2, and
n is 1, 2 or 3, provided that (i) when X is O, R1-R5 are H, R8-R10 are H, and R6 is ethyl or C(O)CH 3 then R7 is not H;

(ii) when X is O, R1-R5 are H, R8-R10 are H, and R6 is methyl then R7 is not methyl; and (iii) when X is O, R1-R5 are H, R8-R10 are H and R6 is H then R7 is not H or ethyl or $(CO)CH_3$.

The term (1-4C)alkyl as used in the definition of the invention means a branched or unbranched alkyl group having 1-4 carbon atoms, for example methyl, ethyl, propyl, isopropyl, butyl, sec-butyl and tert-butyl.

The term (1-6C)alkyl as used in the definition of the invention means a branched or unbranched alkyl group having 1-6 carbon atoms, for example methyl, ethyl, propyl, isopropyl, butyl, sec-butyl, tert-butyl and hexyl. (1-5C)Alkyl groups are preferred, (1-4C)alkyl being the most preferred.

The term halogen means fluorine, chlorine, bromine or iodine.

The term (1-6C)alkoxy means an alkoxy group having 1-6 carbon atoms, the alkyl moiety having the same meaning as previously defined. (1-2C)Alkoxy groups are preferred.

The term (1-6C)alkoxycarbonyl means an alkoxycarbonyl group, the alkoxy group of which contains 1-6 carbon atoms and has the same meaning as previously defined. (1-4C)Alkoxycarbonyl groups are preferred.

The term (1-4C)alkylsulfonyl means an alkylsulfonyl group, the alkyl group of which contains 1-4 carbon atoms and has the same meaning as previously defined. (1-2C)Alkylsulfonyl groups are preferred.

The term (6-10C)aryl means an aromatic hydrocarbon group having 6-10 carbon atoms, such as phenyl, naphthyl, tetrahydronaphthyl or indenyl, which may optionally be substituted with one or more substituents selected from hydroxy, amino, halogen, nitro, trifluoromethyl, cyano or (1-4C)alkyl, the alkyl moiety having the same meaning as previously defined. The preferred aromatic hydrocarbon group is phenyl.

The term (6-10)arylsulfonyl means an arylsulfonyl group, the aryl group of which contains 6-10 carbon atoms and has the same meaning as previously defined. Phenylsulfonyl is preferred.

The term (2-4C)alkenyl means a branched or unbranched alkenyl group having 2-4 carbon atoms, such as ethenyl and 2-butenyl.

The term (2-4C)alkynyl means a branched or unbranched alkynyl group having 2-4 carbon atoms, such as ethynyl and propynyl.

The term amino(1-4C)alkyl means an aminoalkyl group, the alkyl group of which contains 1-4 carbon atoms and has the same meaning as previously defined. Amino(1-2C)alkyl groups are preferred.

The term hydroxy(1-4C)alkyl means a hydroxyalkyl group, the alkyl group of which contains 1-4 carbon atoms and has the same meaning as previously defined. Hydroxy(1-2C)alkyl groups are preferred.

The term 1,4-bisaryl means two phenyl groups in which the second phenyl group is connected to the 4-position of the first phenyl group.

The term carboxy(1-4C)alkyl means a carboxyalkyl group, the alkyl group of which contains 1-4 carbon atoms and has the same meaning as previously defined. Carboxy(1-2C)alkyl groups are preferred.

The term (3-6C)cycloalkyl means a cycloalkyl group having 3-6 carbon atoms, being cyclopropyl, cyclobutyl, cyclopentyl and cyclohexyl.

The term pharmaceutically acceptable salt represents those salts which are, within the scope of medical judgement, suitable for use in contact for the tissues of humans and/or animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

For the purposes of the present invention, the term trans when naming fused polycyclic compounds is understood to mean that relative stereochemistry wherein the ring substituent in position 1 in Formula I is located on the other side of said ring from the ring bond to an annulated ring system in position 14b. Consequently, the substituent in position 1 is on the same side of the ring system as the bridgehead hydrogen atom occupying position 14b. In addition, the use of the term trans will be clear to those skilled in the art from the illustrations in the various diagrams, figures and reaction schemes.

Prodrugs represent compounds which are rapidly transformed in vivo to the parent compound of the above formula, for example by hydrolysis in blood.

The compounds of Formula I exist as mixtures of stereochemical isomers; preferred is absolute stereochemistry (1S,14bR).

Preferred compounds are those compounds wherein R2 is selected from the group consisting of H, halogen, $NO_2$, and NR11R12 wherein R11 and R12 independently are selected from the group consisting of H, (1-6C)alkoxycarbonyl, (1-4C)alkylsulfonyl and (6-10C)arylsulfonyl.

Particularly preferred are the compounds according to Formula I wherein R1 and R5 are H and R3 and R4 are independently selected from H or halogen.

X preferably is O, S or $CH_2$, more preferably O or $CH_2$. Other interesting compounds are those compounds wherein R6 is H or C(Y)R15 and R15 is H or (1-4C)alkyl, preferably (1-2C)alkyl, the alkyl groups optionally being substituted with one or more halogen atoms.

Also preferred are compounds wherein R2 is H, halogen or $NO_2$. Most preferred at R2 are H and F.

Most preferred compounds are those compounds wherein R11 is H and R12 is (1-6C)alkoxycarbonyl, (1-4C)alkylsulfonyl or (6-10C)arylsulfonyl.

Also highly preferred are compounds wherein R2 is H, R3 is halogen, R15 is methyl, optionally substituted with 1-3 halogen atoms, and Y is O or S, more particularly those compounds wherein R4 is H and X is O. Compounds having some or more of the preferences identified above combined in the general Formula I are highly preferred.

Additional preferred compounds are those wherein R2 is H or halogen, R3 and/or R4 are independently selected from the group consisting of H, CN, halogen, (2-4C)alkenyl and C(O)(1-4C)alkyl, and R5 and/or R10 are independently selected from H or halogen.

More preferred are compounds wherein X is selected from the group consisting of O, S and $NCH_3$.

Also preferred are compounds wherein R8 and R9 are H.

Furthermore preferred are compounds wherein R6 is H or C(Y)R15 and R15 is H or (1-4C)alkyl optionally substituted with one or more halogen atoms.

Also preferred are compounds wherein Y is O or S, and R15 is methyl, optionally substituted with one or more halogen atoms.

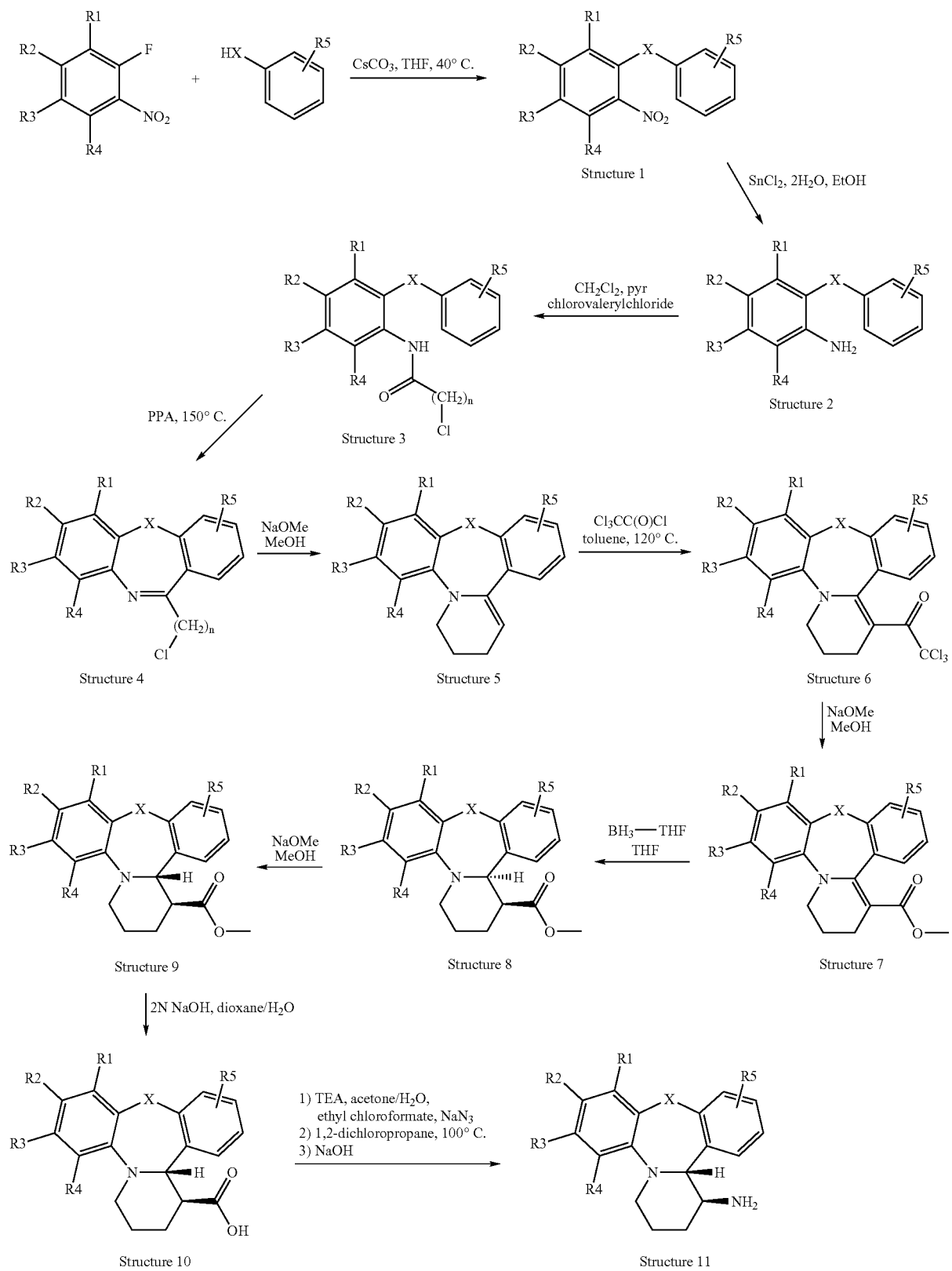

The sequences of steps to synthesize the compounds of the present invention are shown in Schemes I-XVIII. In each of the Schemes the R groups correspond to the substitution pattern noted in the Examples and to Formula I.

Tetracyclic templates (such as structure 11) were constructed by routine synthetic methods as described in Scheme I. Nucleophilic aromatic substitution of 2-fluoro nitrophenyls with appropriately substituted phenols, thiophenols or anilines provided the diaryl ethers, thioethers or amines 1, respectively. In the case of X=CH$_2$, structure 1 was commercially available. Reduction of the nitro group with SnCl$_2$ yielded the aniline derivatives 2. Acylation of the aniline functionality with 5-chlorovaleryl chloride yielded the amides 3. Subsequent ring closure was accomplished by treatment of the amide with PPA at 150° C. Treatment of imine structures 4 with sodium methoxide resulted in an intramolecular cyclization and afforded the tetracyclic systems 5. Reaction of the enamine functionality with trichloroacetyl chloride yielded the trichloroacetyl derivatives 6. The trichloroacetyl functionality was transformed into methyl ester derivatives 7 on treatment with sodium methoxide. Subsequent reduction of the alkene functionality of the unsaturated carboxylates 7 with borane gave exclusively cis isomers such as structures 8. Epimerisation to the trans isomers 9 was accomplished upon treatment of 8 with sodium methoxide. Saponification of the ester afforded the carboxylate 10 which subsequently was transformed via a classic Curtius reaction to an amine functionality resulting in the trans-1-amino-tetrahydropyrido-dibenz(ox/othi/odi)azepine derivatives 11. The racemic mixture was separated into its pure enantiomers via chiral HPLC (OJ column (25×0.46 cm)).

The tetracyclic compounds (11) were employed as starting materials in Schemes II and III. In Scheme II is depicted the acylation of the amine functionality of structure 11, which was accomplished via various different routine synthetic methods (i.e. acid chlorides, anhydrides, carboxylic acids with coupling reagents, or amidation). The resulting amide structures 12 were target of subsequent modification. Treatment of the amides such as structure 12 with phosphorous pentasulfide afforded the thioamides 13.

Alkylation of the amide in 12 with alkylating agents in the presence of sodium hydride afforded structures 14. Structures 15 have been prepared via amidine formation of the amine functionality of 11 by treatment with nitrile derivatives such as trifluoroacetonitrile.

Scheme II

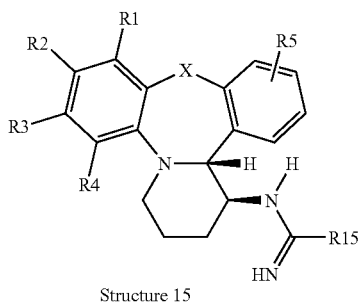

Structure 15

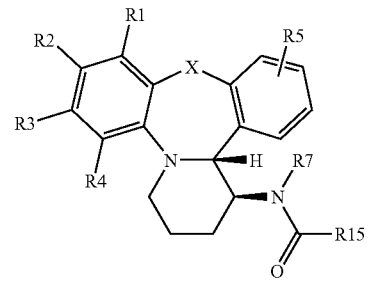

Structure 14

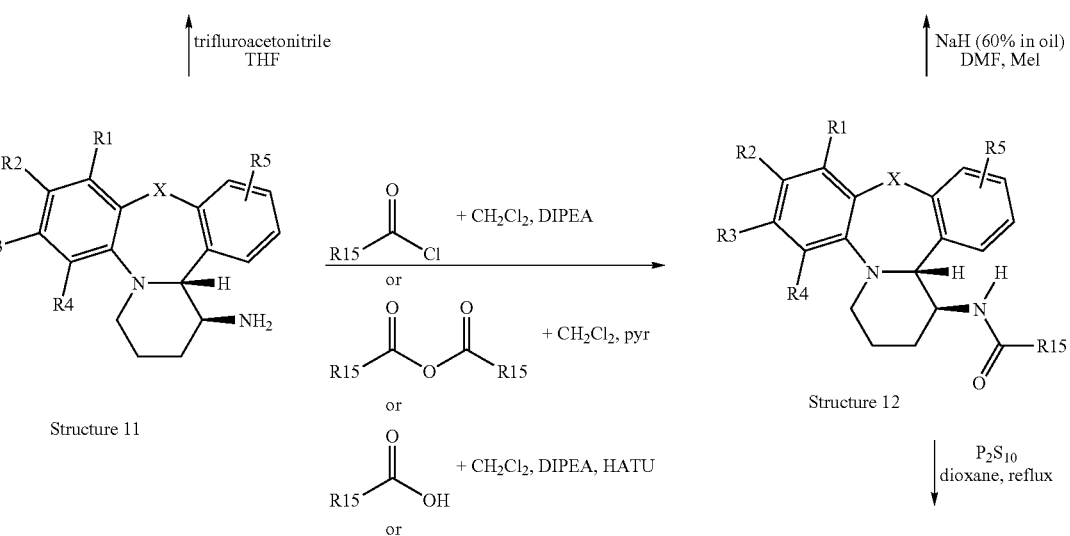

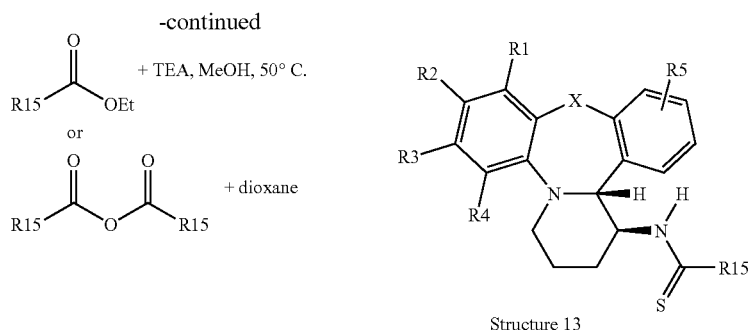

Structure 13

Scheme III describes the formation of the urethane structures 16 starting from 11 via reaction with chloroformates in the presence of sodium bicarbonate. Treatment of structure 11 with isothiocyanates afforded the thiourea derivatives 17. Reductive alkylation of the amine functionality in structure 11 with aldehydes in the presence of sodium triacetoxyborohydride afforded structures 18. Alkylation of the amine functionality with 2-methoxyethyl bromide afforded structures 26. Structures 27 were obtained by treatment with t-butyl bromoacetate.

Scheme III

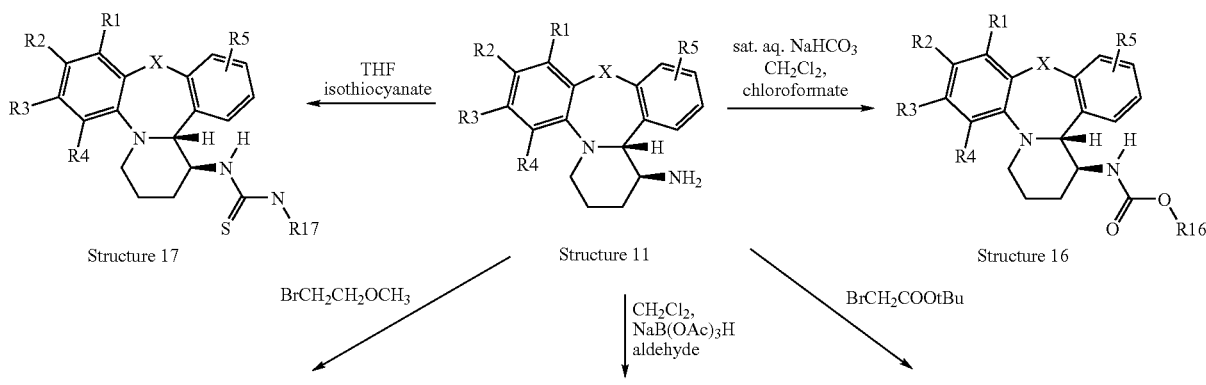

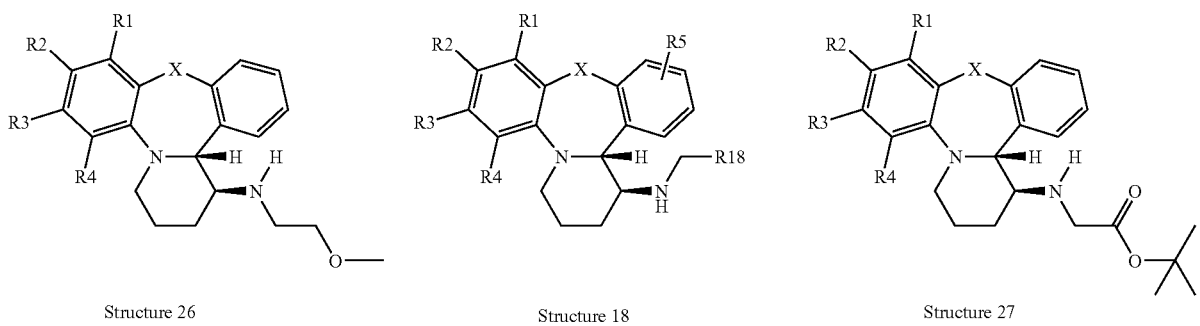

Structure 26  Structure 18  Structure 27

Direct electrophilic aromatic substitutions on core structures afforded various alternative aromatic substituted derivatives (Scheme IV-V).

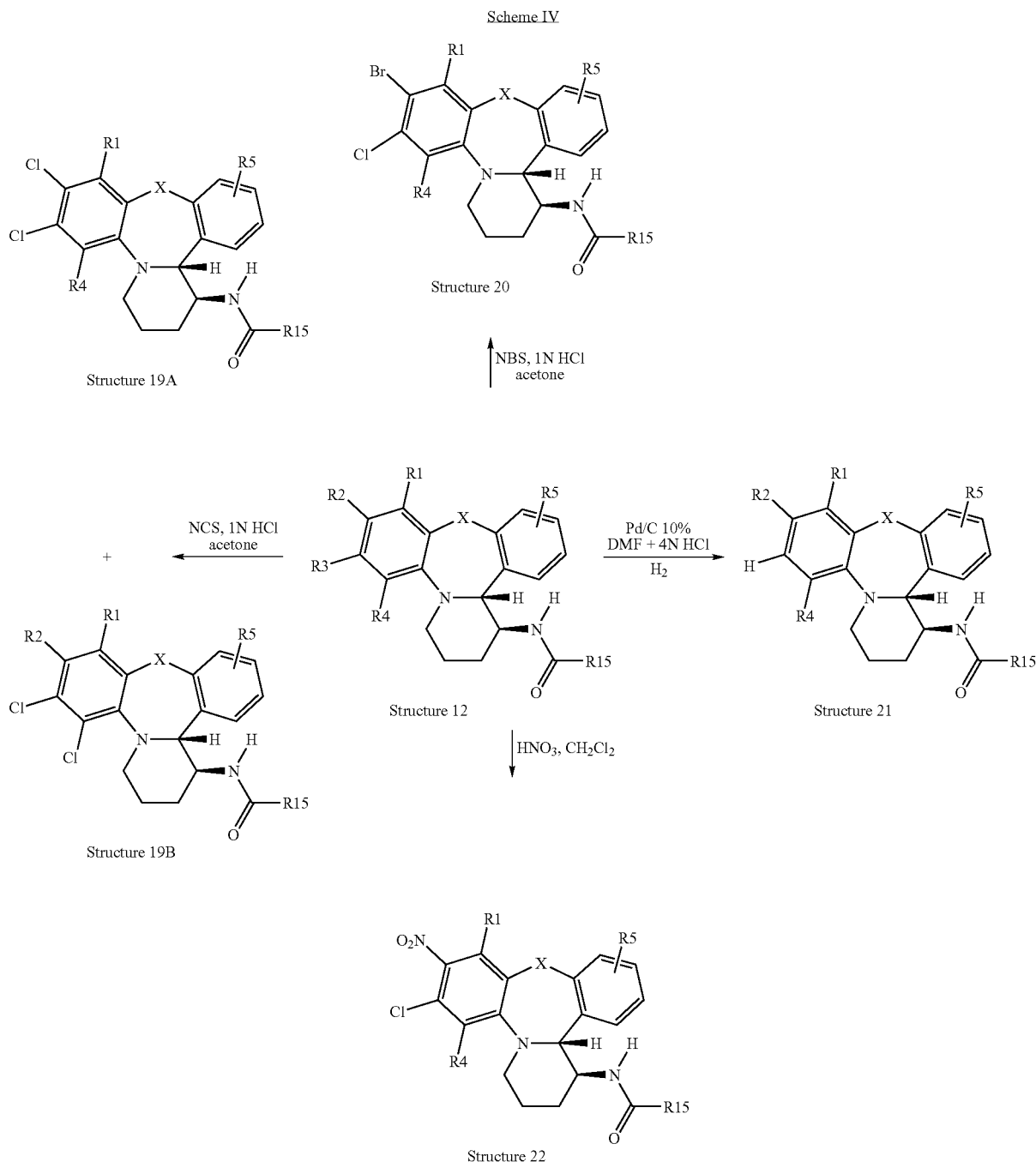

In Scheme IV is described the chlorination of 12 wherein R3 is Cl with N-chlorosuccinimide in the presence of a catalytic amount of HCl; this resulted in the formation of the two different substituted structures 19A and 19B, which were easily separated. In contrast, bromination of 12 with N-bromosuccinimide under identical conditions yielded only the compound with structure 20. Reductive dehalogenation of the chloro compound (12) was achieved by treatment with hydrogen in the presence of Pd/C and HCl to yield the hydro derivative 21. Nitration of structure 12 with nitric acid gave completely selectively the mono-substituted derivative 22.

Direct chlorination on structure 21 (Scheme V) with N-chlorosuccinimide afforded the two regioisomers 23A and 23B, two compounds which were easily separated by chromatographical methods.

Scheme V

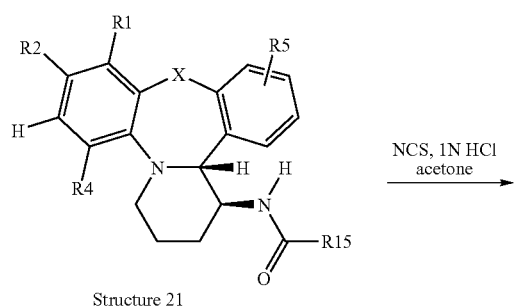

Structure 21

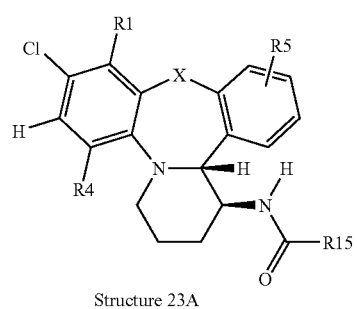

Structure 23A

+

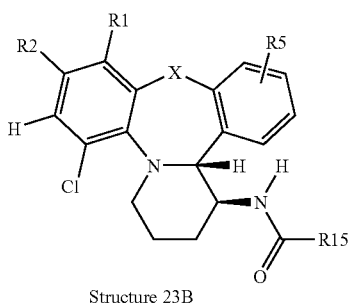

Structure 23B

As shown in Scheme VI reduction of the nitro functionality of structures such as 22 with SnCl$_2$.2H$_2$O in ethanol gave the aniline derivatives 24. Sulfonation or acylation of this aniline functionality afforded the substituted compounds such as structure 25,

Scheme VI

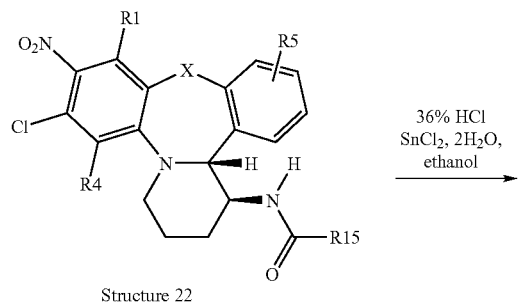

Structure 22

-continued

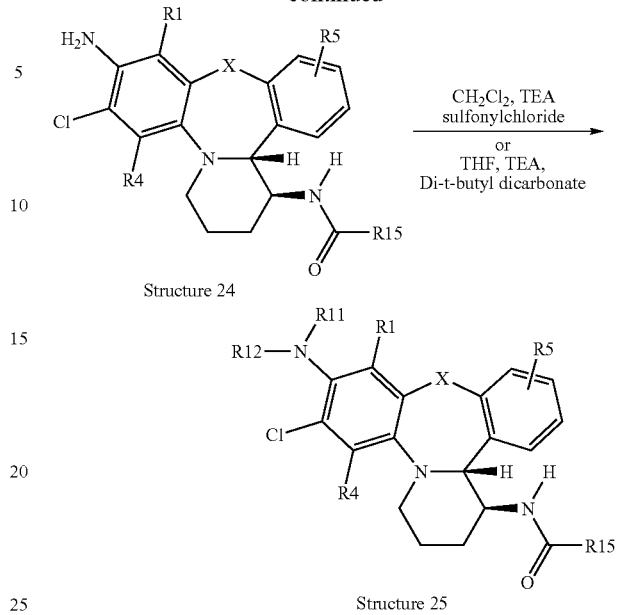

Structure 24

Structure 25

As outlined in Scheme VII, treatment of dichloro compound 19B with K$_2$CO$_3$ resulted in the formation of the corresponding amine 28 and subsequent formylation with ethyl formate afforded structure 29.

Scheme VII

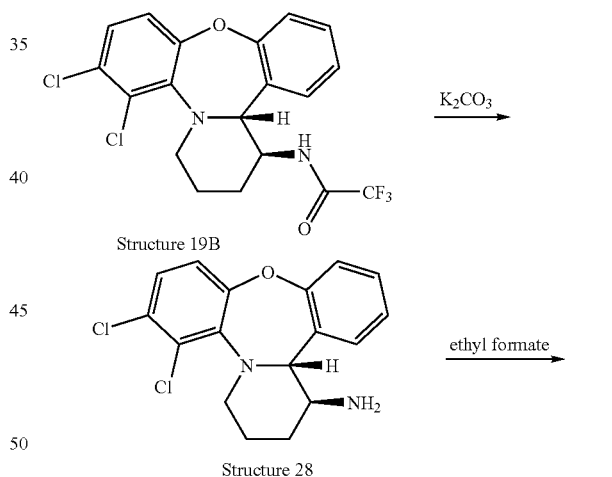

Structure 19B

Structure 28

Structure 29

Schemes VIII and IX describe the synthesis of bromo derivatives 36 where R4=Br. Imine formation by treatment of a mixture of the amine and salicyl aldehyde with p-toluenesulfonic acid and subsequent ring closure by etherification afforded tricyclic intermediates 31.

Scheme VIII

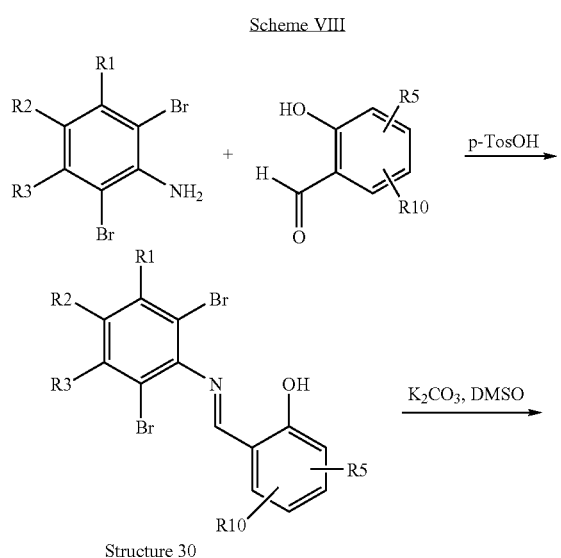

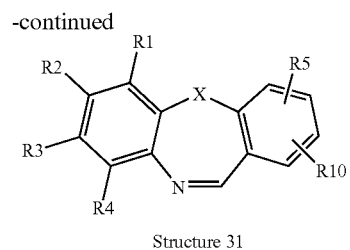

Scheme IX describes the sequences of steps to synthesize compounds 36 starting from tricyclic intermediates such as compounds 31. Treatment of tricyclic imine 31 with glutaric anhydride afforded tetracycles 32. A Curtius rearrangement with DPPA and an alcohol resulted in the formation of urethane structures 33. Reduction of the amide functionality was accomplished by applying borane in THF. Treatment of urethane structures 34 with HBr in acetic acid afforded amines 35. Acylation of the amine functionality with trifluoroacetic anhydride afforded the corresponding amides 36.

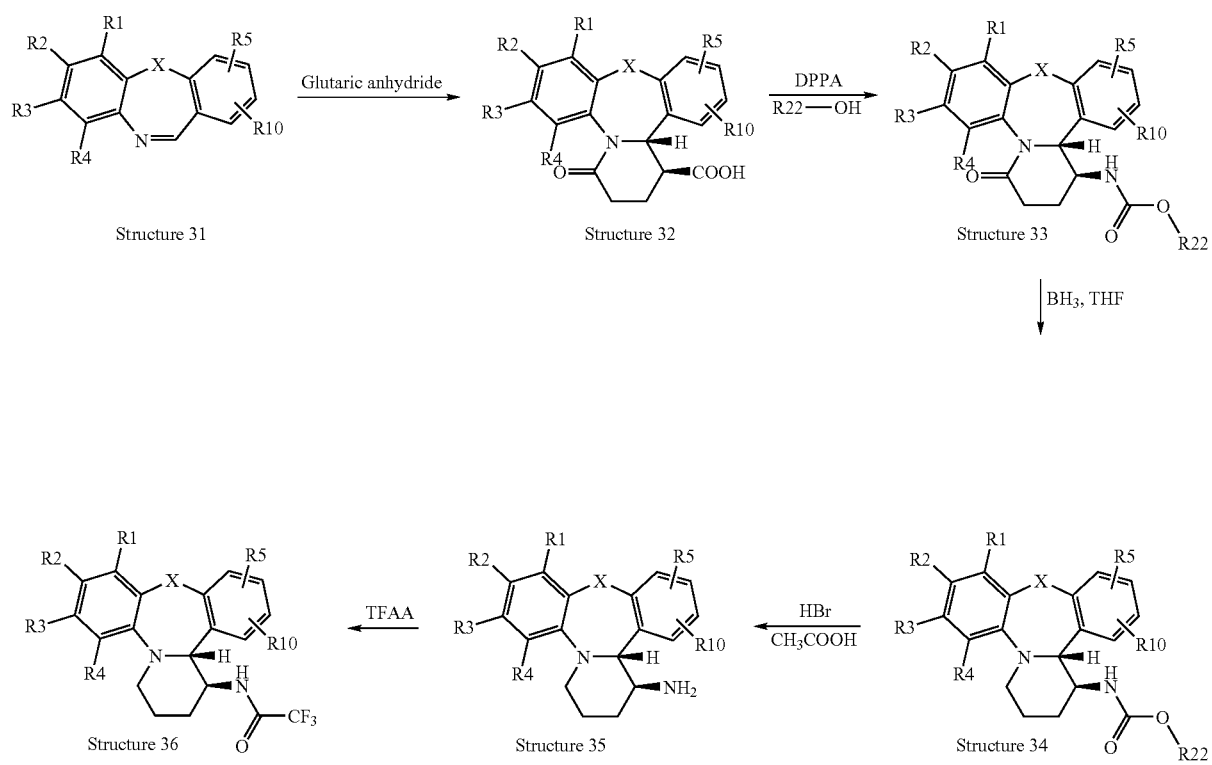

Bromo derivatives 36 were employed as starting materials in scheme X. Stille reactions afforded compounds with an acetyl (structures 37) or a vinyl functionality (structures 39). Treatment of bromo derivatives 36 with CuCN yielded the corresponding cyano compounds 38. Compound 40 was synthesized by a Negishi reaction with a palladium catalyst and methylzinc chloride. Treatment of bromo derivatives 36 with CuI and NaOMe yielded methoxy derivatives 41.

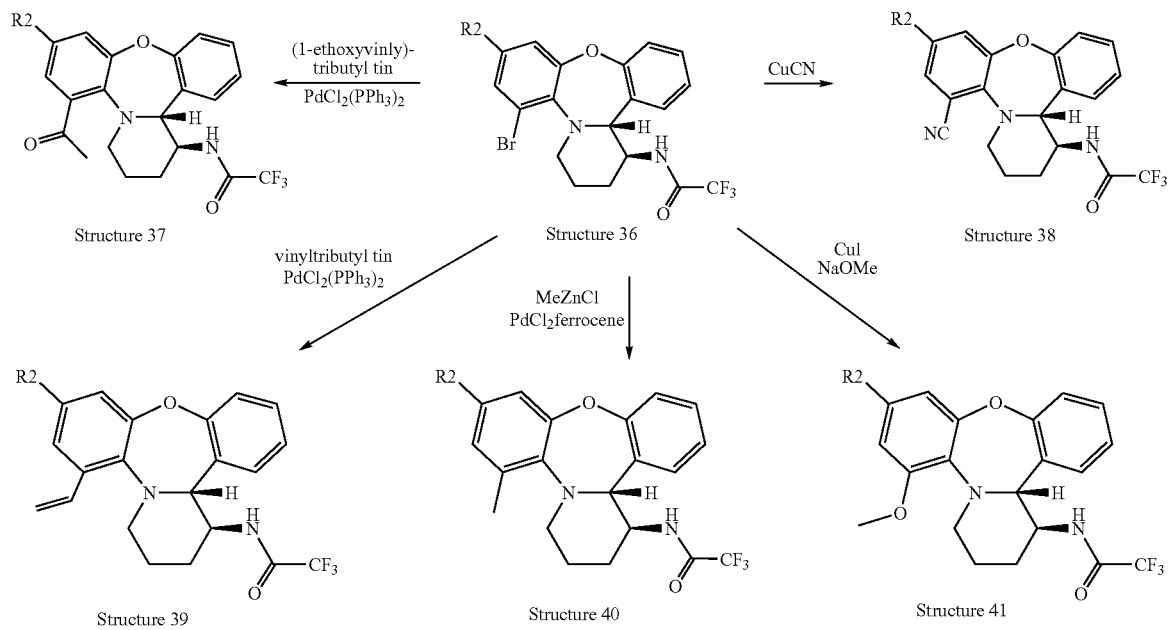

Scheme X

The synthesis of compounds 46 proceeded similar to the route described for bromo derivatives 36. The tricyclic intermediate 45 was synthesized in a different manner than described in scheme XI. The synthesis started with an etherification followed by a reduction of the nitro functionality and a formylation of the amine 43. Treatment with PPA then effected ring closure to tricyclic compound 45.

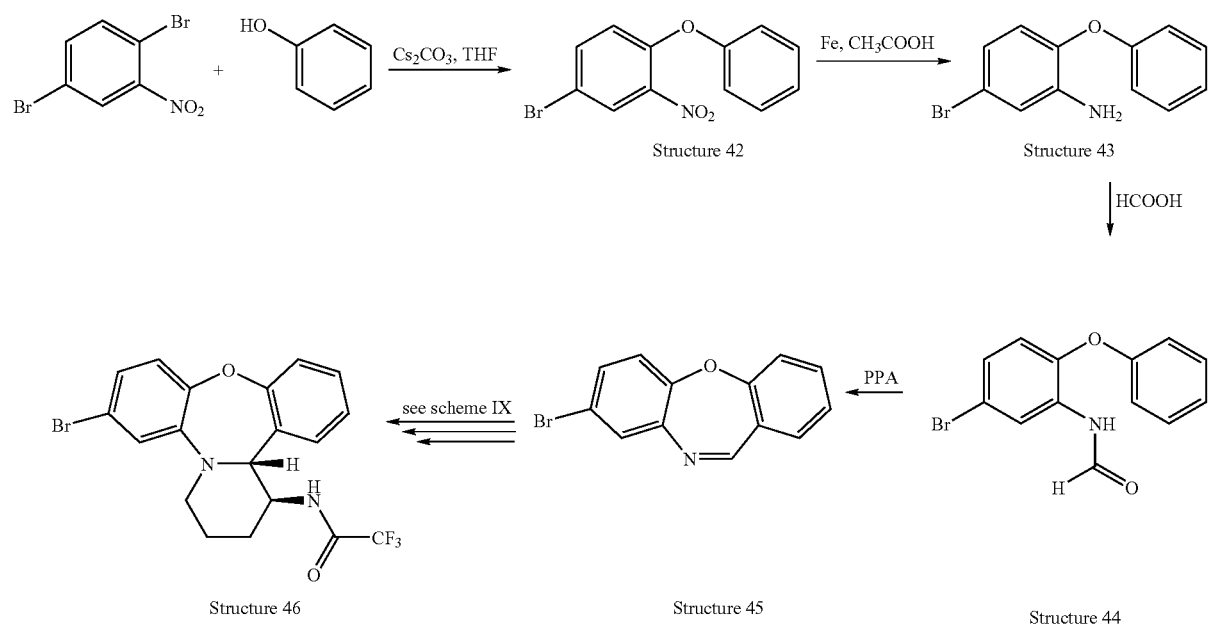

Scheme XI

The bromo derivative 46 was used as starting material in scheme XII where a vinyl (structure 49) and an acetyl derivative (structure 47) were formed by a Stille reaction. A nitrile functionality was introduced by treatment with CuCN. A benzylamine was introduced by a Buchwald reaction; subsequent hydrogenation of this product generated the amine 51. A reaction with propionyl chloride afforded the corresponding amide (structure 52).

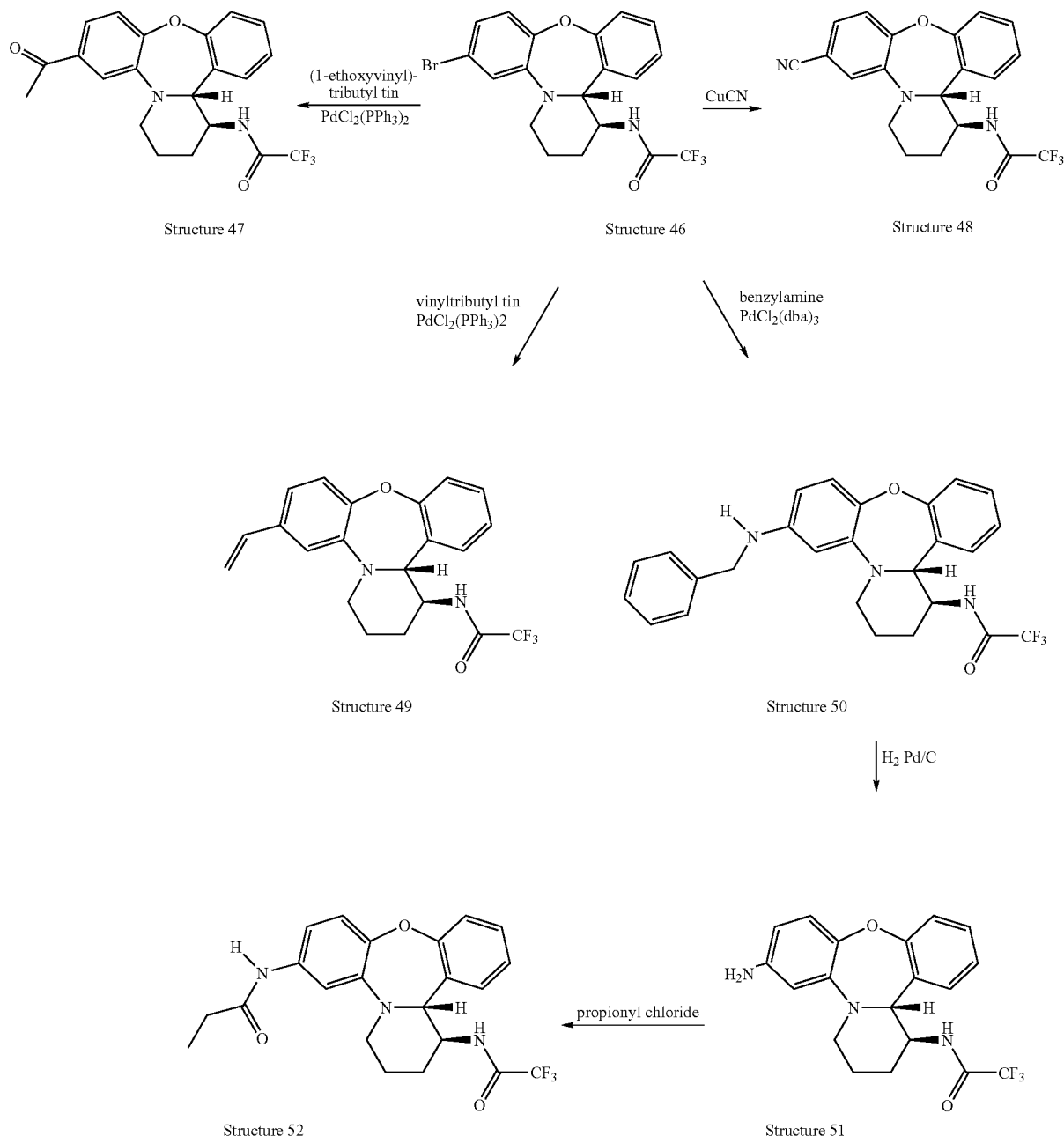

The synthesis of derivatives with R5≠H is described in Schemes XIII and XIV. The tricyclic intermediate was obtained by imine formation and subsequent ring closure through etherification.

Scheme XIII

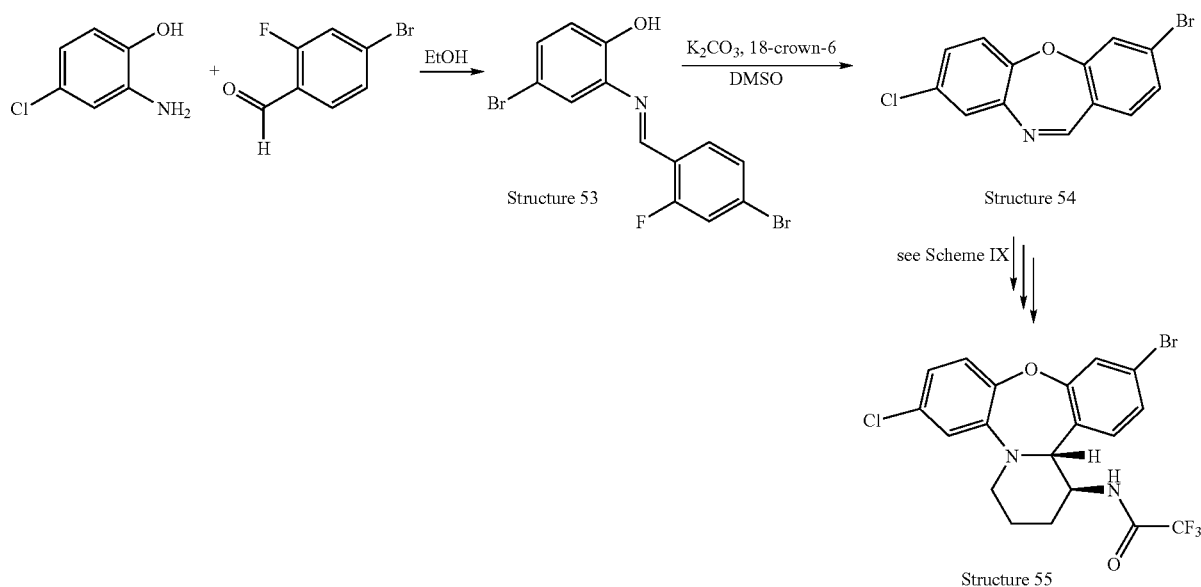

Cyano derivative 56, methyl derivative 57 and dichloro compound 58 were obtained by treatment of compound 55 with CuCN, methylzinc chloride or NCS, respectively, as was described in Scheme X.

Scheme XIV

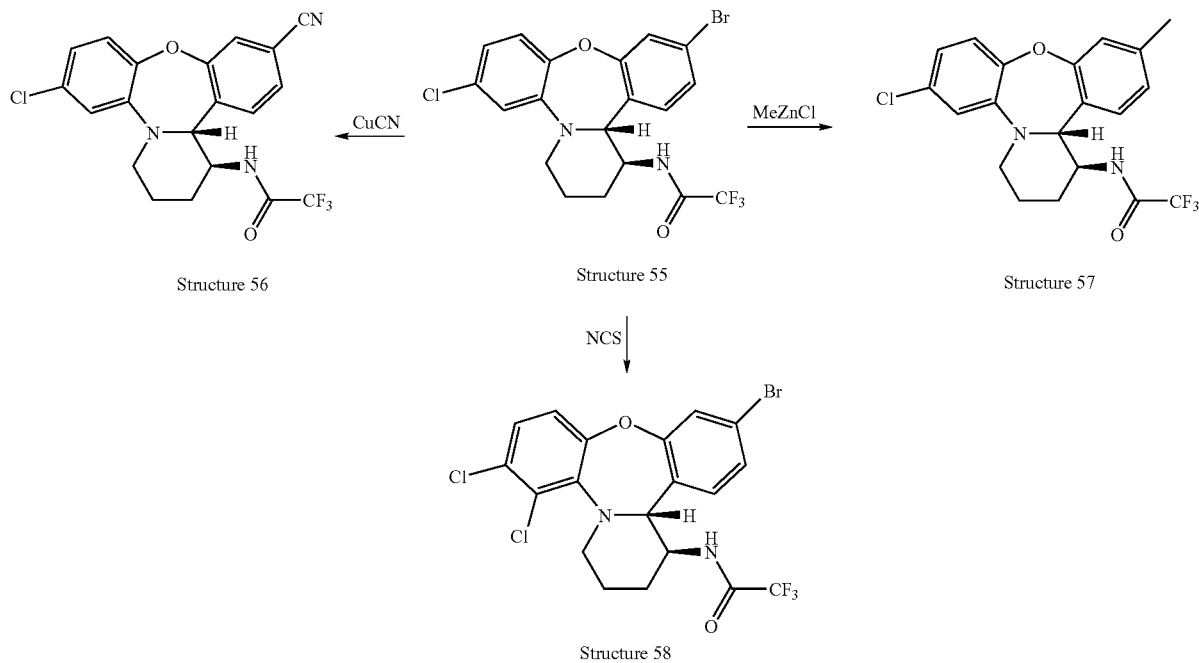

The synthetic route towards fluoro derivatives 61 (R5 and/or R10=F) is shown in Scheme XV and is similar to the synthetic route towards derivatives with R5 ≠H (Scheme XIII). In this case, ring closure by etherification was accomplished by using a microwave.

Scheme XV

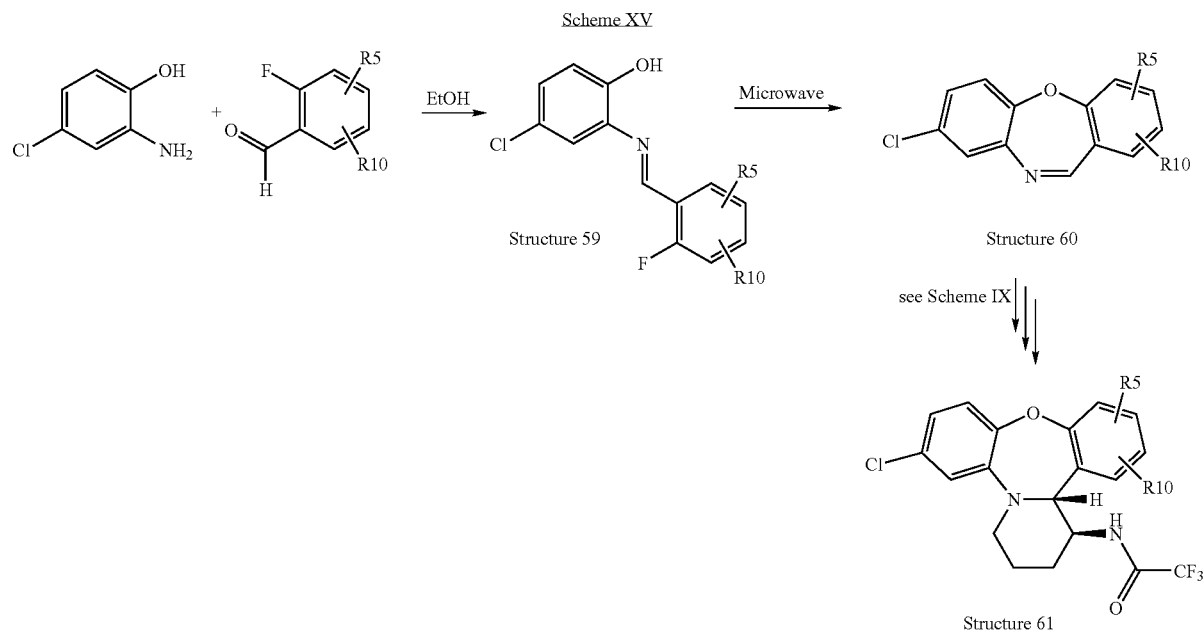

Derivatives with X=N-Me (structures 67, 68 and 69) were synthesized according to Scheme XVI. Tricyclic intermediate 65 was synthesized by a coupling of 4-chloro-1-fluoro-2-nitrobenzene and N-methylaniline, followed by a reduction of the nitro functionality and a formylation of the amine. Ring closure towards intermediate 65 was accomplished by treatment with PPA. The sequences of steps to synthesize compound 66 from compound 65 are described in scheme IX. The amine functionality of compound 66 was acylated to yield amide 67 or alkylated to afford compound 68. Subsequent saponification afforded compound 69.

Scheme XVI

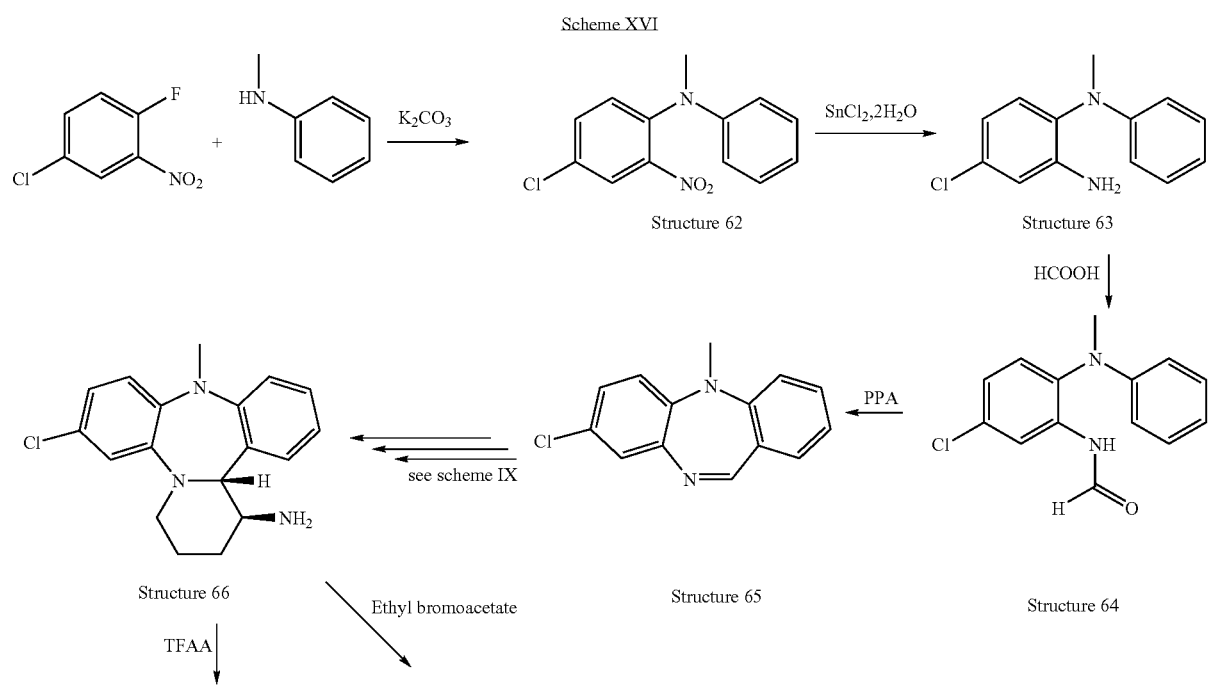

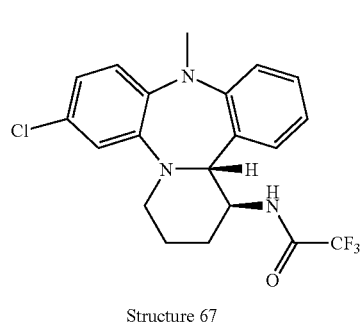
Structure 67
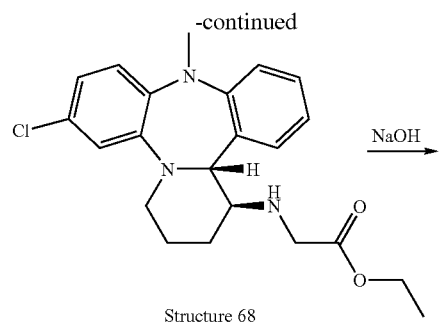
Structure 68
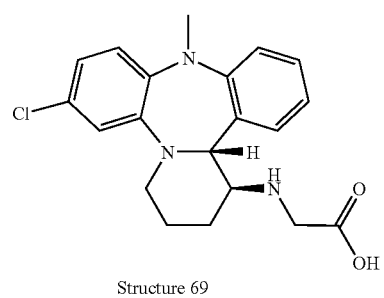
Structure 69
The route towards derivatives with X=N—H proceeded via tricyclic amide 72, which was obtained by an intramolecular condensation. Reduction with LiAlH$_4$ and subsequent oxidation with MnO$_2$ afforded tricyclic intermediate 74. The corresponding amide 75 was synthesized as described in Scheme IX.
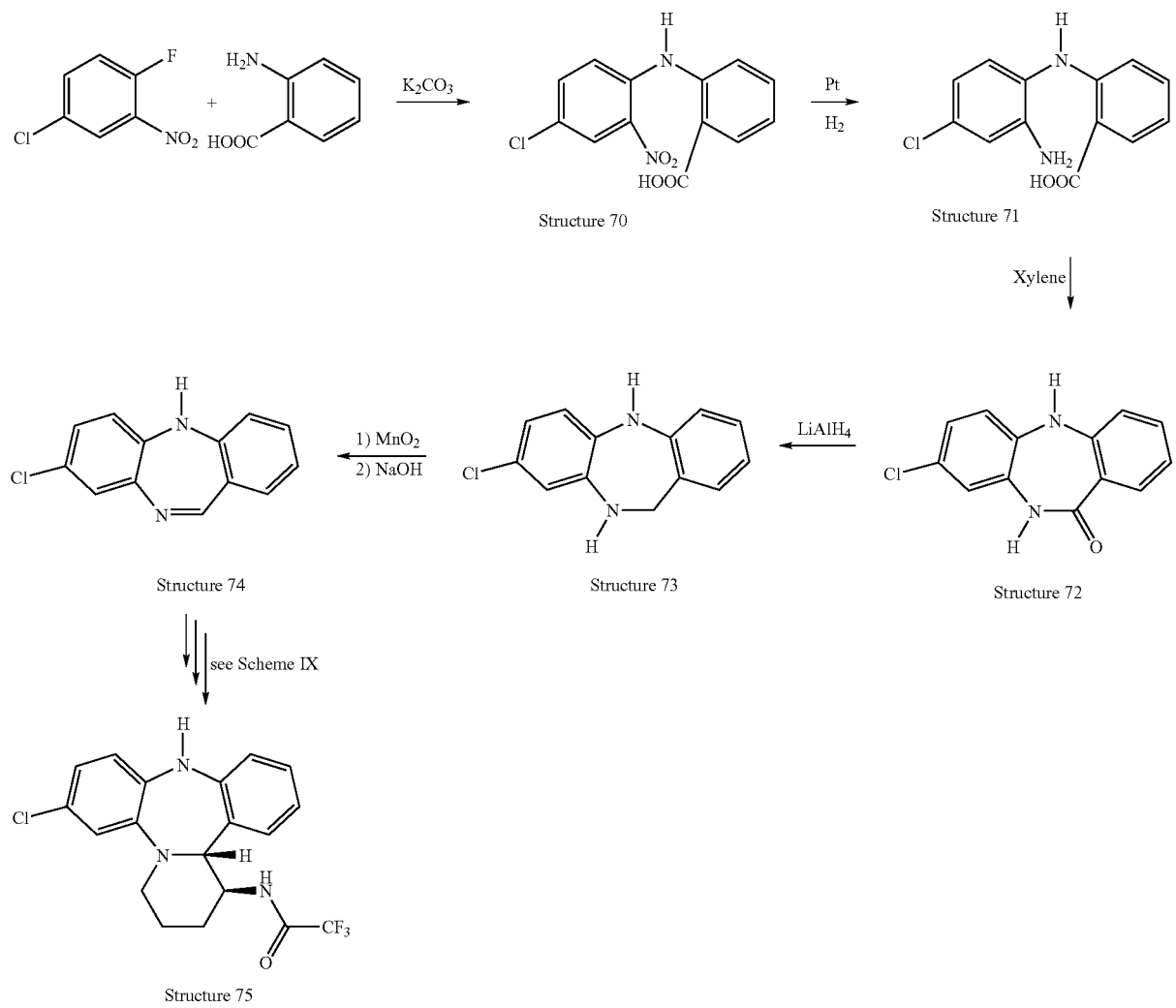

Application of 3-methyl glutaric anhydride in the formation of tetracyclic intermediate 78 and subsequent urethane formation resulted in a mixture of isomers 80, 81 and 82, as shown in Scheme XVIII. Treatment with HBr in acetic acid, followed by an acylation and separation of the isomers, resulted in the formation of amides 86, 87 and 88.
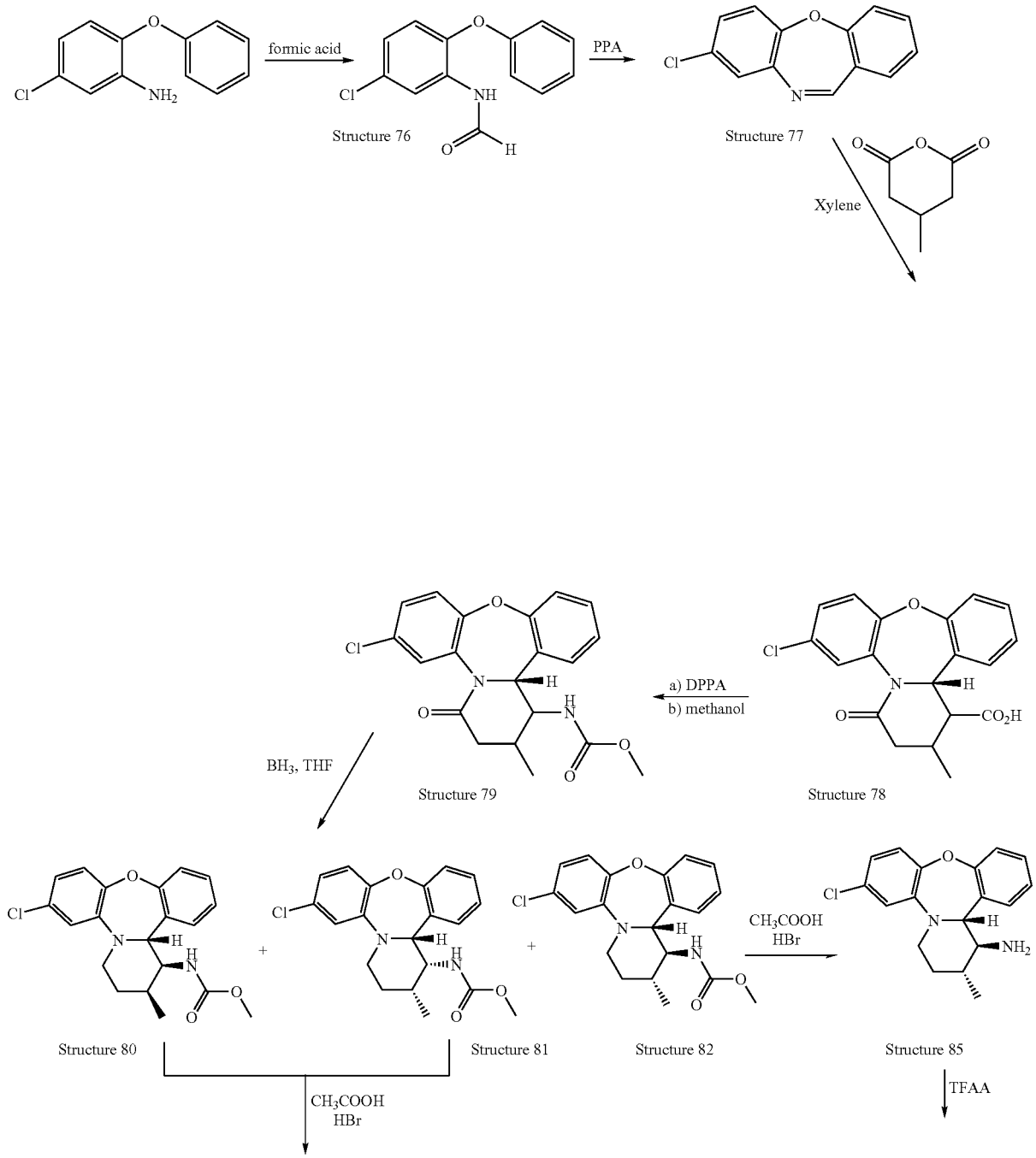

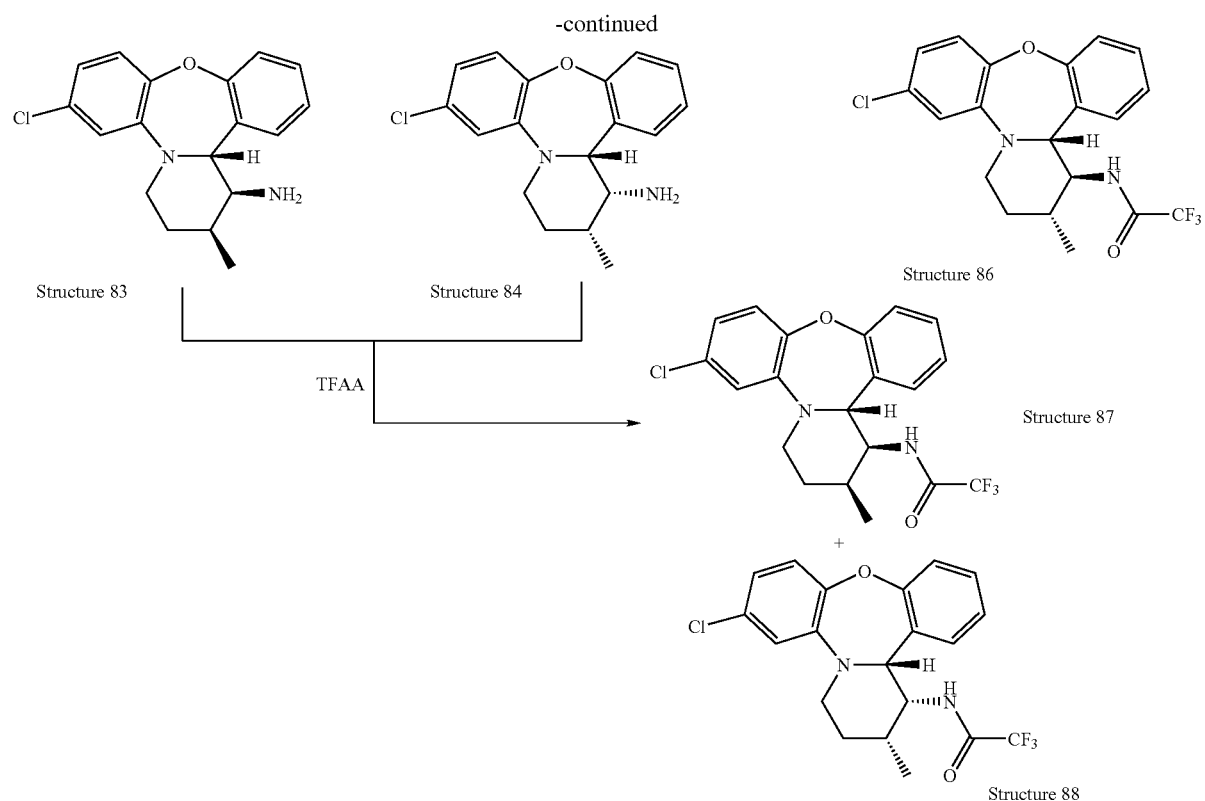

Methods to determine receptor binding as well as in vitro and in vivo assays to determine biological activity of the compounds are well known. In general, expressed receptor is treated with a compound of the invention and binding or stimulation or inhibition of a functional response is measured.

To measure a functional response, isolated DNA encoding the progesterone receptor gene, preferably the human receptor, is expressed in suitable host cells. Such a cell might be the Chinese Hamster Ovary (CHO) cell, but other cells are also suitable. Preferably the cells are of mammalian origin.

Methods to construct recombinant progesterone receptor-expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site-directed mutagenesis, ligation of additional sequences, PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided through the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with a compound of the invention to observe binding, or stimulation or inhibition of a functional response.

Alternatively, isolated cytosol containing the expressed receptor may be used to measure binding of a compound of the invention.

For measurement of binding, radioactive or fluorescence-labelled compounds may be used. As reference compound, the native hormone, or other compounds binding to the receptor, can be used. As an alternative, competition binding assays can be performed as well.

Another assay involves screening for progesterone receptor agonist compounds of the invention by determining regulation of receptor mediated natural target gene mRNA, i.e. genes regulated by the receptor through binding of the receptor in the promoter region of the gene. The levels of target gene mRNA will be reduced or increased, depending on the inhibitory or stimulating effect of a compound of the invention upon binding to the receptor.

In addition to direct measurement of mRNA levels in the exposed cells, cells can be used which in addition to transfection with receptor encoding DNA have also been transfected with a second DNA encoding a reporter gene, the expression of which responds to binding of the receptor towards responsive elements in the promoter of the particular reporter gene. Such responsive elements might be classical hormone responsive elements, well known in the art and described e.g., in Beato, M, Chalepakis, G, Schauer, M, Slater, E P (1989) J. Steroid Biochem. 5:737-47 or might be constructed in such a way that they are connected to novel responsive elements. In general, reporter gene expression might be controlled by any response element reacting to progesterone receptor binding. Suitable reporter genes are e.g. LacZ, alkaline phosphatase, firefly luciferase and green fluorescence protein.

For selecting active agonist compounds on the progesterone receptor, testing at $10^{-5}$ M must result in an activity of more than 30% of the maximal activity when (16α)-16-ethyl-21-hydroxy-19-norpregn-4-ene-3,20-dione (Org 2058) is used as a reference. For selecting antagonist compounds on the progesterone receptor, testing at $10^{-5}$ M must result in an activity of more than 10% of the maximal activity when (6β,11β,17β)-11-[4-(dimethylamino)phenyl]4',5'-dihydro-6-methylspiro[estra-4,9-diene-17,2'(3'H)-furan]-3-one (Org 31710) is used as a reference. Another criterion might be the $EC_{50}$ value, which must be $<10^{-5}$ M, preferably $<10^{-7}$ M.

The skilled artisan will recognize that desirable $EC_{50}$ values are dependent on the compound of the invention which is being tested. For example, a compound with an $EC_{50}$ which is less than $10^{-5}$ M is, generally, considered a candidate for drug selection. Preferably this value is lower than $10^{-7}$ M. However, a compound which has a higher $EC_{50}$, but is selective for the particular receptor, may still be a candidate for drug selection.

Basically any transactivation assay in mammalian cells (cell line or primary culture), that can yield information about the possible receptor activation can be used for the purpose of selecting potent ligands. The added value of using several cell systems, with cells which originate from different organs, will be that information on the potential tissue specificity of the ligands is obtained. Examples of cells frequently used to this end are, besides CHO cells, a.o. T47D cells, MCF7 cells, ECC-1 cells, HeLa cells, primary cultures of endometrial cells, and pituitary cells.

The invention further resides in a pharmaceutical composition comprising a compound having the general Formula I or a salt thereof.

Thus, the compounds according to the invention can be used in therapy.

The compounds of the present invention can be applied clinically in those regimens where progestagens are used.

The invention therefore resides in the use of a compound having the general Formula I for the manufacture of a medicament for modulating progesterone receptor mediated health conditions in women, more in particular hormone dependent cancers such as breast, ovary and uterus cancer; endometriosis and fertility control. The invention also relates to a treatment of the conditions identified above by administering a compound of the invention.

Suitable administration routes for the compounds of Formula I or pharmaceutically acceptable salts thereof, also referred to herein as the active ingredient, are intramuscular injections, subcutaneous injections, intravenous injections or intraperitoneal injections, oral and intranasal administration. Preferably, the compounds can be administered orally. The exact dose and regimen of administration of the active ingredient, or a pharmaceutical composition thereof, will necessarily be dependent upon the therapeutic effect to be achieved (e.g. treatment of infertility; contraception, endometriosis) and may vary with the particular compound, the route of administration, and the age and condition of the individual subject to whom the medicament is to be administered.

In general, parenteral administration requires lower dosages than other methods of administration which are more dependent upon adsorption. However, a dosage for humans preferably contains 0.0001-25 mg per kg body weight. The desired dose may be presented as one dose or as multiple subdoses administered at appropriate intervals throughout the day, or, in case of female recipients, as doses to be administered at appropriate (daily) intervals throughout the menstrual cycle. The dosage as well as the regimen of administration may differ between a female and a male recipient.

The present invention thus also relates to pharmaceutical compositions comprising a compound according to Formula I in admixture with pharmaceutically acceptable auxiliaries, and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy, for example, using methods such as those described in Gennaro et al., Remington's Pharmaceutical Sciences (18th ed., Mack Publishing company, 1990, see especially Part 8: *Pharmaceutical Preparations and Their Manufacture*).

Such methods include the step of bringing in association the active ingredient with any auxiliary agent. The auxiliary agent(s), also named accessory ingredients, include those conventional in the art (Gennaro, supra), such as, fillers, binders, diluents, disintegrants, lubricants, colorants, flavouring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for the use as hereinbefore described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions or formulations suitable for administration by nasal inhalation include fine dusts or mists which may be generated by means of metered dose pressurized aerosols, nebulisers or insufflators.

The derivatives of the invention can also be administered in the form of devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO N.V.).

The invention is illustrated by the foll owing examples.

EXAMPLES

Example 1 trans-7-Fluoro-2,3,4,14b-tetrahydro-1H-dibenzo[b,f] pyrido[1,2-d][1,4]oxazepine-1-amine (Structure 11 of Scheme I, where R1=H, R2=H, R3=F, R4=H, R5=H, R6=H, R7=H, X=O)

5-Fluoro-2-phenoxynitrobenzene $Cs_2CO_3$ (12.1 g, 62.9 mmol) was added to a solution of phenol (5.9 g, 62.9 mmol) in 400 mL of THF under $N_2$. After stirring for 15 min. 2,5-difluoronitrobenzene (6.82 mL, 62.9 mmol) in 50 mL of THF was added. The resulting mixture was heated to 40° C. for 25 h. Reaction was followed by HPLC to detect disappearance of 2,5-difluoronitrobenzene. Water and ethyl acetate were added, followed by extraction with ethyl acetate (2×). The combined organic layers were successively washed with saturated aq. sodium bicarbonate (3×), water and brine, dried (Na$_2$SO$_4$) and evaporated. The crude compound was chromatographed on silica to remove excess of phenol. Elution with toluene/ethyl acetate 95:5 gave the title compound (12.6 g, 86%). Data: (m/z)=234 (M+H)$^+$.

5-Fluoro-2-phenoxyaniline

General Method 1: Reduction of a Nitro Compound of Structure 1 to an Aniline of Structure 2.

SnCl$_2$.2H$_2$O (88.0 g, 390 mmol) was added to a solution of 5-Fluoro-2-phenoxynitrobenzene (22.3 g, 95.7 mmol) in 450 mL of ethanol under N$_2$. The resulting mixture was stirred at 40° C. for 30 min. and additionally under cooling for 2 h. Ethanol was removed by evaporation under reduced pressure and 300 mL of ethyl acetate was added. The organic layer was washed with water and cold 1N NaOH. The emulsion was filtered over decalite, washed with water, extracted with ethyl acetate, dried (Na$_2$SO4), and evaporated to give the crude compound as a dark brown oil (19.6 g, 100%). Data: (m/z)= 204 (M+H)$^+$.

5-Chloro-N-(5-fluoro-2-phenoxyphenyl)pentanamide

General Method 2: Acylation of an Aniline of Structure 2 to an Amide of Structure 3.

A solution of 5-chloropentanoyl chloride (13.0 mL, 100 mmol) in 13 mL CH$_2$Cl$_2$ was added in 30 minutes to a solution of 5-fluoro-2-phenoxyaniline (19.6 g, 95.7 mmol) in 88 mL of CH$_2$Cl$_2$ and 7 mL of pyridine at <25° C. After the mixture had been stirred for 1 h at room temperature 100 mL of ice-water was added at 0° C. After 18 h stirring at room temperature the two layers were separated. The organic layer was washed with cold 2N NaOH and water, dried (Na$_2$SO4) and evaporated to give the crude compound as a brown oil (31.0 g, 100%). Data: (m/z)=322 (M+H)$^+$.

8-Fluoro-11-(4-chlorobutyl)dibenz[b,f][1,4]oxazepine

General Method 3: Ring Closure of an Amide of Structure 3 to an Imine of Structure 4.

PPA (190 g, 84%) was added to a solution of 5-chloro-N-(5-fluoro-2-phenoxyphenyl)pentanamide (31.0 g, 95.7 mmol). The resulting mixture was stirred at 150° C. for 2.5 h and subsequently cooled to 50° C. 500 mL of ethyl acetate and 300 mL of ice-water were added. The mixture was stirred for 1 h. The organic layer was washed with cold 1N NaOH and water, dried (Na$_2$SO$_4$) and evaporated to give the crude compound as a black oil (26.3 g, 90%). Data: (m/z)=304 (M+H)$^+$.

7-Fluoro-3,4-dihydro-2H-dibenzo[b,f]pyrido[1,2-d][1,4]oxazepine

General Method 4: Ring Closure of an Imine of Structure 4 to a Tetracycle of Structure 5.

A solution of 8-fluoro-11-(4-chlorobutyl)dibenz[b,f][1,4] oxazepine (26.3 g, 86.6 mmol) in 45 mL of methanol was added to a solution of sodium methoxide (9.6 g, 177 mmol) in 115 mL of methanol under N$_2$. The resulting mixture was heated to reflux for 5 h, cooled to room temperature and stirred overnight. Water and CH$_2$Cl$_2$ were added and the mixture was poured into 500 mL of water and extracted with CH$_2$Cl$_2$. The organic layer was washed with water, dried (Na$_2$SO$_4$) and evaporated, and the crude compound was chromatographed on silica. Elution with toluene gave the title compound as a brown oil (16.5 g, 77%). Data: (m/z)=268 (M+H)$^+$.

7-Fluoro-1-(trichloroacetyl)-3,4-dihydro-2H-d]dibenzo[b,f] pyrido[1,2-d][1,4]oxazepine General Method 5: Conversion of an Enamine of Structure 5 to a Trichloroacetyl Derivative of Structure 6.

Trichloroacetyl chloride (8.75 mL, 78.5 mmol) was added to a solution of 7-fluoro-3,4-dihydro-2H-dibenzo[b,f]pyrido [1,2-d][1,4]oxazepine (16.5 g, 61.9 mmol) in 125 mL of toluene under N$_2$. After stirring for 15 min. triethylamine (7.7 mL) was added over 15 min. The resulting brown suspension was heated to 120° C. for 75 min. After cooling to 5° C. 100 mL of ice-water was added. After stirring for 1 h the mixture was poured into 500 mL water and extracted with ethyl acetate. The organic layer was washed with cold saturated aq. sodium bicarbonate and water, dried (Na$_2$SO$_4$) and evaporated to give the crude compound as a black foam (19.1 g, 75%). Data: (m/z)=412 (M+H)$^+$.

Methyl 7-fluoro-3,4-dihydro-2H-d]dibenzo[b,f]pyrido[1,2-d][1,4]oxazepine-1-carboxylate General Method 6: Conversion of a Trichloroacetyl Compound of Structure 6 to a Methyl Ester of Structure 7.

A solution of sodium methoxide (7.64 g, 141.6 mmol) in 60 mL of methanol was added to a suspension of 7-fluoro-1-(trichloroacetyl)-3,4-dihydro-2H-dibenzo[b,f]pyrido[1,2-d] [1,4]oxazepine (19.1 g, 46.4 mmol) in 60 mL of methanol. The resulting mixture was stirred for 30 min. at room temperature and heated to reflux for 1 h. After cooling to room temperature the mixture was poured into 700 mL of ice-water and extracted with CH$_2$Cl$_2$. The organic layer was washed with water, dried (Na$_2$SO$_4$) and evaporated to give the title compound as a black foam (13.9 g, 92%). Data: (m/z)=326 (M+H)$^+$.

Methyl cis-7-fluoro-2,3,4,14b-tetrahydro-1H-dibenzo[b,f] [pyrido[1,2-d][1,4]oxazepine-1-carboxylate General Method 7: Reduction of an Unsaturated Carboxylate of Structure 7 to a Saturated Carboxylate of Structure 8.

BH$_3$-THF complex (1M, 40 mL, 40.0 mmol) was added in 45 min. to a solution of methyl 7-fluoro-3,4-dihydro-2H-dibenzo[b,f]pyrido[1,2-d][1,4]oxazepine-1-carboxylate (14.0 g, 42.8 mmol) in 84 mL of THF under N2 (T<5° C.). The resulting mixture was stirred for 105 min. at 20° C. After cooling to 0° C. 20 mL of acetic acid was added in 2 h. The reaction mixture was poured into 500 mL of ice-water, extracted with CH$_2$Cl$_2$, washed with water, dried (Na$_2$SO$_4$) and evaporated. The crude product was chromatographed on silica. Elution with heptane/ethyl acetate 7:3 gave the title compound as a light brown foam (10.0 g, 71%). Data: (m/z)= 328 (M+H)$^+$.

Methyl trans-7-fluoro-2,3,4,14b-tetrahydro-1H-dibenzo[b,f] pyrido[1,2-d][1,4]oxazepine-1-carboxylate General Method 8: Epimerisation of cis-Carboxylate of Structure 8 to a trans-Carboxylate of Structure 9.

Sodium methoxide (1.00 g, 1.85 mol) was added to a suspension of methyl cis-7-fluoro-2,3,4,14b-tetrahydro-1H-dibenzo[b,f][pyrido[1,2-d][1,4]oxazepine-1-carboxylate (10.0 g, 30.6 mmol) in 100 mL of methanol under N$_2$. The resulting mixture was heated to reflux for 4.5 h. After cooling the clear brown solution was poured into 700 mL of ice-water and extracted with CH$_2$Cl$_2$. The organic layer was washed with water, dried (Na$_2$SO$_4$) and evaporated to give the title compound (9.1 g, 91%). Data: (m/z)=328 (M+H)$^+$.

trans-3-Fluoro-2,3,4,14b-tetrahydro-1H-dibenzo[b,f]pyrido [1,2-d][1,4]oxazepine-1-carboxylic Acid General Method 9: Saponification of a Carboxylate of Structure 9 to a Carboxylic Acid of Structure 10.

65 mL of 2N NaOH was added to a solution of methyl trans-7-fluoro-2,3,4,14b-tetrahydro-1H-dibenzo[b,f]pyrido[1,2-d][1,4]oxazepine-1-carboxylate (9.10 g, 27.8 mmol) in 280 mL of dioxane and 110 mL of water. The resulting mixture was heated to 70° C. for 2 h. The cooled mixture was poured into 1.5 L of ice-water and 100 mL of 2N HCl and extracted with $CH_2Cl_2$ (3×). The organic layer was washed with water, dried ($Na_2SO_4$) and evaporated. Crystallisation from $CH_2Cl_2$/ether 1:3 gave the title compound (5.3 g, 61%). Data: (m/z)=314 $(M+H)^+$.

trans-7-Fluoro-2,3,4,14b-tetrahydro-1H-d]-dibenzo[b,f]pyrido[1,2-d][1,4]oxazepine-1-amine (Structure 11 of Scheme 1, where R1=H, R2=H, R3=F, R4=H, R5=H, R6=H, R7=H, X=O)

General Method 10: Amination of Carboxylic Acid of Structure 10 to an Amine of Structure 11.

2.60 mL of triethylamine was added in 5 minutes at 0° C. under $N_2$ to a suspension of trans-7-fluoro-2,3,4,14b-tetrahydro-1H-dibenzo[b,f]pyrido[1,2-d][1,4]oxazepine-1-carboxylic Acid (4.0 g, 12.8 mmol) in 30 mL of acetone and 1 mL of water. Additionally 1.80 mL of ethyl chloroformate was added and the mixture was stirred at 0° C. for 30 min. Sodium azide (1.65 g, 26.3 mmol) in 8 mL of water was added to the resulting emulsion and stirring was continued for 2.5 h at 0° C. The mixture was poured into 500 mL of water and extracted with $CH_2Cl_2$. The organic layer was washed with water, dried ($Na_2SO_4$) and evaporated to give the crude compound. This crude product was dissolved in 90 mL of 1,2-dichloropropane and heated to 100° C. for 4 h. The mixture was then evaporated under reduced pressure. The residue was dissolved in 45 mL of methoxyethanol. A solution of sodium hydroxide (2.72 g, 84.7 mmol) in 6 mL of water was added. The resulting mixture was heated to 120° C. for 2.5 h after which it was cooled and poured into 400 mL of ice-water. The water layer was extracted with $CH_2Cl_2$ and the organic layer was washed with water, dried ($Na_2SO_4$), evaporated and chromatographed on alumina. Elution with toluene/ethyl acetate 3:7 gave the title compound as a brown oil (1.45 g, 34%). Data: (m/z)=285 $(M+H)^+$.

Example 2 trans-7-Chloro-2,3,4,14b-tetrahydro-1H-dibenzo[b,f]pyrido[1,2-d][1,4]thiazepine-1-amine (Structure 11 of Scheme I, where R1=H, R2=H, R3=Cl, R4=H, R5=H, R6=H, R7=H, X=S)

5-Chloro-2-(phenylthio)aniline

This compound was prepared by General Method 1 at room temperature to afford 5-chloro-2-(phenylthio)aniline (6.8 g, 77%). Data: (m/z)=236 $(M+H)^+$.

5-Chloro-N-[5-chloro-2-(phenylthio)phenyl]pentanamide

This compound was prepared by General Method 2 to afford 5-chloro-N-[5-chloro-2-(phenylthio)phenyl]pentanamide (11.0 g, 100%). Data: (m/z)=354 $(M+H)^+$.

8-Chloro-11-(4-chlorobutyl)dibenzo[b,f][1,4]thiazepine

This compound was prepared by General Method 3 to afford 8-chloro-11-(4-chlorobutyl)dibenzo[b,f][1,4]thiazepine as a black tar (4.0 g, 45%). Data: (m/z)=338 $(M+H)^+$.

7-Chloro-3,4-dihydro-2H-dibenzo[b,f]pyrido[1,2-d][1,4]thiazepine

This compound was prepared by General Method 4, followed by chromatography on silica. Elution with toluene gave 7-chloro-3,4-dihydro-2H-dibenzo[b,f]pyrido[1,2-d][1,4]thiazepine as a red-brown oil (1.2 g, 47%). Data: (m/z)=300 $(M+H)^+$.

7-Chloro-1-(trichloroacetyl)-3,4-dihydro-2H-dibenzo[b,f]pyrido[1,2-d][1,4]thiazepine This compound was prepared by General Method 5 to afford 7-chloro-1-(trichloroacetyl)-3,4-dihydro-2H-dibenzo[b,f]pyrido[1,2-d][1,4]thiazepine as a black tar (1.6 g, 93%). Data: (m/z)=446 $(M+H)^+$.

Methyl 7-chloro-3,4-dihydro-2H-dibenzo[b,f]pyrido[1,2-d][1,4]thiazepine-1-carboxylate This compound was prepared by General Method 6 to afford methyl 7-chloro-3,4-dihydro-2H-dibenzo[b,f]pyrido[1,2-d][1,4]thiazepine-1-carboxylate as a black foam (1.2 g, 94%).

Methyl cis-7-chloro-2,3,4,14b-tetrahydro-1H-dibenzo[b,f]pyrido[1,2-d][1,4]thiazepine-1-carboxylate This compound was prepared by General Method 7 to afford methyl cis-7-chloro-2,3,4,14b-tetrahydro-1H-dibenzo[b,f]pyrido[1,2-d][1,4]thiazepine-1-carboxylate as a brown foam (1.0 g, 100%). Data: (m/z)=360 $(M+H)^+$.

Methyl trans-7-chloro-2,3,4,14b-tetrahydro-1H-dibenzo[b,f]pyrido[1,2-d][1,4]thiazepine-1-carboxylate This compound was prepared by General Method 8 to afford methyl trans-7-chloro-2,3,4,14b-tetrahydro-1H-dibenzo[b,f]pyrido[1,2-d][1,4]thiazepine-1-carboxylate (0.77 g, 73%). Data: (m/z)=360 $(M+H)^+$.

trans-7-Chloro-2,3,4,14b-tetrahydro-1H-dibenzo[b,f]pyrido[1,2-d][1,4]thiazepine-1-carboxylic Acid This compound was prepared by General Method 9 to afford trans-7-chloro-2,3,4,14b-tetrahydro-1H-dibenzo[b,f]pyrido[1,2-d][1,4]thiazepine-1-carboxylic acid (0.24 g, 32%). Data: (m/z)=346 $(M+H)^+$.

trans-7-Chloro-2,3,4,14b-tetrahydro-1H-dibenzo[b,f]pyrido[1,2-d][1,4]thiazepine-1-amine (Structure 11 of Scheme I, where R1=H, R2=H, R3=Cl, R4=H, R5=H, R6=H, R7=H, X=S)

This compound was prepared by General Method 10 to afford trans-7-chloro-2,3,4,14b-tetrahydro-1H-dibenzo[b,f]pyrido[1,2-d][1,4]thiazepine-1-amine as a brown solid (165 mg, 75%). Data: (m/z)=317 $(M+H)^+$.

Example 3 trans-7-Chloro-2,3,4,14b-tetrahydro-1H-dibenzo[b,f]pyrido[1,2-d][1,4]oxazepine-1-amine (Structure 11 of Scheme I, where R1=H, R2=H, R3=Cl, R4=H, R5=H, X=O)

5-Chloro-N-(5-chloro-2-phenoxyphenyl)pentanamide

This compound was prepared by General Method 2 to afford 5-chloro-N-(5-chloro-2-phenoxyphenyl)pentanamide as a brown oil (24.1 g, 100%). Data: $^1$H-NMR (400 MHz, $CDCl_3$) 1.83 (m, 4H), 2.40 (t, J=7.0, 2H), 3.54 (t, J=7.0, 2H), 6.76 (d, J=8.0, 1H), 6.97 (dd, J=8.0, 2.0, 1H), 6.99 (s, 1H), 7.02 (s, 1H), 7.17 (t, J=8.0, 1H, 7.37 (d, J=8.0, 1H), 7.39 (d, J=8.0, 1H), 7.72 (br, 1H), 8.54 (d, J=2.0, 1H). (m/z)=338 $(M+H)^+$.

8-Chloro-11-(4-chlorobutyl)dibenz[b,f][1,4]oxazepine

This compound was prepared by General Method 3 to afford 8-chloro-11-(4-chlorobutyl)dibenz[b,f][1,4]oxazepine as a thick brown-greenish oil (21.6 g, 94%). Data:

¹H-NMR (400 MHz, CDCl₃) 1.90 (m, 4H), 2.96 (t, J=8.0, 2H), 3.58 (t, J=8.0, 2H), 7.04-7.48 (7 arH). (m/z)=320 (M+H)⁺.

7-Chloro-3,4-dihydro-2H-dibenz[b,f]pyrido[1,2-d][1,4]oxazepine

This compound was prepared by General Method 4, followed by chromatography on alumina. Elution with toluene gave 7-chloro-3,4-dihydro-2H-dibenz[b,f]pyrido[1,2-d][1,4]oxazepine as a dark brown oil (3.92 g, 83%). Data: ¹H-NMR (400 MHz, CDCl₃) 2.06 (dt, J=16.0, 8.0, 2H), 2.32 (m, 2H), 3.69 (t, J=8.0, 2H), 4.87 (t, J=4.0, 1H), 6.73 (dd, J=8.0, 3.0, 1H), 6.90 (d, J=3.0, 1H), 7.02 (d, J=8.0, 1H), 7.09 (m, 2H), 7.22 (m, 1H), 7.36 (dd, J=8.0, 2.0, 1H). (m/z)=284 (M+H)⁺.

7-Chloro-1-(trichloroacetyl)-3,4-dihydro-2H-dibenzo[b,f]pyrido[1,2-d][1,4]oxazepine This compound was prepared by General Method 5 to afford 7-chloro-1-(trichloroacetyl)-3,4-dihydro-2H-dibenzo[b,f]pyrido[1,2-d][1,4]oxazepine] as a black tar (5.70 g, >100% crude). Data: ¹H-NMR (400 MHz, CDCl₃) 2.19 (dt, J=16.0, 8.0, 2H), 2.95 (m, 2H), 3.90 (m, 2H), 6.96 (dd, J=8.0, 3.0, 1H), 7.04-7.37 (7 arH). (m/z)=430 (M+H)⁺.

Methyl 7-chloro-3,4-dihydro-2H-dibenzo[b,f]pyrido[1,2-d][1,4]oxazepine-1-carboxylate This compound was prepared by General Method 6 followed by chromatography on silica. Elution with toluene/ethyl acetate 9:1 gave methyl 7-chloro-3,4-dihydro-2H-dibenzo[b,f]pyrido[1,2-d][1,4]oxazepine-1-carboxylate] (2.75 g, 65%). Data: ¹H-NMR (400 MHz, CDCl₃) 2.11 (dt, J=16.0, 8.0, 2H), 2.65 (m, 2H), 3.38 (s, 3H), 3.82 (m, 2H), 6.88 (dd, J=8.0, 3.0, 1H), 7.06 (m, 3H), 7.14 (d, J=8.0, 1H), 7.23 (dd, J=8.0, 2.0, 1H), 7.30 (dt, J=8.0, 2.0, 1H). (m/z)=342 (M+H)⁺.

Methyl cis-7-chloro-2,3,4,14b-tetrahydro-1H-dibenzo[b,f]pyrido[1,2-d][1,4]oxazepine-1-carboxylate This compound was prepared by General Method 7 to afford methyl cis-7-chloro-2,3,4,14b-tetrahydro-1H-dibenzo[b,f]pyrido[1,2-d][1,4]oxazepin-1-carboxylate] as a yellow-brown foam (10.2 g, 100%). Data: ¹H-NMR (400 MHz, CDCl₃) 2.27 (m, 4H), 3.02 (dt, J=12.0, 4.0, 1H), 3.16 (m, 2H), 3.53 (s, 3H), 5.06 br, 1H), 6.75 (dd, J=8.0, 3.0, 1H), 6.90 (d, J=3.0, 1H), 7.00 (d, J=8.0, 1H), 7.05 (dt, J=8.0, 2.0, 1H), 7.17 (dt, J=8.0, 2.0, 2H), 7.20 (dt, J=8.0, 2.0, 1H). (m/z)=344 (M+H)⁺.

Methyl trans-7-chloro-2,3,4,14b-tetrahydro-1H-dibenzo[b,f]pyrido[1,2-d][1,4]oxazepine-1-carboxylate This compound was prepared by General Method 8 to afford methyl trans-7-chloro-2,3,4,14b-tetrahydro-1H-dibenzo[b,f]pyrido[1,2-d][1,4]oxazepine-1-carboxylate (9.5 g, 93%). Data: (m/z)=344 (M+H)⁺.

trans-7-Chloro-2,3,4,14b-tetrahydro-1H-dibenzo[b,f]pyrido[1,2-d][1,4]oxazepine-1-carboxylic Acid This compound was prepared by General Method 9. Crystallisation from CH₂Cl₂/ether 1:3 gave trans-7-chloro-2,3,4,14b-tetrahydro-1H-dibenzo[b,f]pyrido[1,2-d][1,4]oxazepine-1-carboxylic acid] (3.89 g, 51%) Data: (m/z)=302 (M+H)⁺.

trans-7-Chloro-2,3,4,14b-tetrahydro-1H-dibenzo[b,f]pyrido[1,2-d][1,4]oxazepine-1-amine (Structure 11 of Scheme I, where R1=H, R2=H, R3=Cl, R4=H, R5=H, X=O)

This compound was prepared by General Method 10. Crystallisation from ether gave trans-7-chloro-2,3,4,14b-tetrahydro-1H-dibenzo[b,f]pyrido[1,2-d][1,4]oxazepine-1-amine as an off-white solid (2.97 g, 68%). Data: (m/z)=301 (M+H)⁺.

Example 4 trans-7-Chloro-1,2,3,4,10,14b-hexahydro-dibenzo[c,f]pyrido[1,2-a]azepine-1-amine (Structure 11 of Scheme I, where R1=H, R2=H, R3=Cl, R4=H, R5=H, R6=H, R7=H, X=CH₂)

5-Chloro-N-[5-chloro-2-(phenylmethyl)phenyl]pentanamide

This compound was prepared by General Method 2 to afford 5-chloro-N-[5-chloro-2-(phenylmethyl)phenyl]pentanamide as an off-white solid (2.90 g, 100%). Data: (m/z)= 336 (M+H)⁺.

3-Chloro-6-(4-chlorobutyl)-11H-dibenz[b,e]azepine

This compound was prepared by General Method 3 to afford 3-chloro-6-(4-chlorobutyl)-11H-dibenz[b,e]azepine (Scheme I, structure 4 wherein R1=R2=R4=R5=H, R3=Cl, X=CH₂ and n=4) as a black tar (2.60 g, 97%). Data: (m/z)= 318 (M+H)⁺.

7-Chloro-2,3,4,10-tetrahydrodibenzo[c,f]pyrido[1,2-a]azepine

This compound was prepared by General Method 4, followed by chromatography on silica. Elution with toluene gave 7-chloro-2,3,4,10-tetrahydrodibenzo[c,f]pyrido[1,2-a]azepine as a orange-brown oil (0.89 g, 39%). Data: (m/z)=282 (M+H)⁺.

7-Chloro-1-(trichloroacetyl)-2,3,4,10-tetrahydrodibenzo[c,f]pyrido[1,2-a]azepine This compound was prepared by General Method 5 to afford 7-chloro-1-(trichloroacetyl)-2,3,4,10-tetrahydrodibenzo[c,f]pyrido[1,2-a]azepine as a dark brown foam (1.34 g, 99%).

Methyl 7-chloro-2,3,4,10-tetrahydrodibenzo[c,f]pyrido[1,2-a]azepine-1-carboxylate This compound was prepared by General Method 6 to afford methyl 7-chloro-2,3,4,10-tetrahydrodibenzo[c,f]pyrido[1,2-a]azepine-1-carboxylate as a dark brown foam (1.01 g, 95%). Data: (m/z)=340 (M+H)⁺.

Methyl cis-7-chloro-1,2,3,4,10,14b-hexahydrodibenzo[c,f]pyrido[1,2-a]azepine-1-carboxylate This compound was prepared by General Method 7 to afford methyl cis-7-chloro-1,2,3,4,10,14b-hexahydrodibenzo[c,f]pyrido[1,2-a]azepine-1-carboxylate as a dark brown foam (1.00 g, 98%). Data: (m/z)=342 (M+H)⁺.

Methyl trans-7-chloro-1,2,3,4,10,14b-hexahydrodibenzo[c,f]pyrido[1,2-a]azepine-1-carboxylate This compound was prepared by General Method 8 to afford methyl trans-7-chloro-1,2,3,4,10,14b-hexahydrodibenzo[c,f]pyrido[1,2-a]azepine-1-carboxylate (0.93 g, 93%).

trans-7-Chloro-1,2,3,4,10,14b-hexahydrodibenzo[c,f]pyrido[1,2-a]azepine-1-carboxylic Acid This compound was prepared by General Method 9. Crystallisation from CH₂Cl₂/ether 1:3 gave trans-7-chloro-1,2,3,4,10,14b-hexahydrodibenzo[c,f]pyrido[1,2-a]azepine-1-carboxylic acid (3.89 g, 51%) Data: (m/z)=302 (M+H)⁺.

trans-7-Chloro-1,2,3,4,10,14b-hexahydrodibenzo[c,f]pyrido[1,2-a]azepine-1-amine (Structure 11 of Scheme I, where R1=H, R2=H, R3=Cl, R4=H, R5=H, R6=H, R7=H, X=CH2)

This compound was prepared by General Method 10 to afford trans-7-chloro-1,2,3,4,10,14b-hexahydrodibenzo[c,f]pyrido[1,2-a]azepine-1-amine (104 mg, 86%). Data: (m/z)=299 (M+H)$^+$.

Example 5 trans-2,2,2-Trifluoro-N-(7-fluoro-2,3,4,14b-tetrahydro-1H-dibenzo[b,f]pyrido[1,2-d][1,4]oxazepin-1-yl)acetamide (Structure 12 of Scheme II, where R1=H, R2=H, R3=F, R4=H, R5=H, R15=CF$_3$, X=O)

General Method 11: N-acylation of an Amine of Structure 11 to a Trifluoro Amide of Structure 12.

Trifluoroacetic anhydride (1 mL) was added to trans-7-fluoro-2,3,4,14b-tetrahydro-1H-dibenzo[b,f]pyrido[1,2-d][1,4]oxazepine-1-amine (0.6 g, 2.1 mmol) in 5 mL CH$_2$Cl$_2$ and 2 mL of pyridine. The resulting suspension was stirred for 18 h at room temperature. The brown solution was poured into 100 mL of ice-water and extracted with CH$_2$Cl$_2$. The organic layer was washed with water, dried (Na$_2$SO$_4$) and evaporated. Diethyl ether was added to the resulting solid and heated to reflux for 30 min. The residue was dissolved in CH$_2$Cl$_2$ and heated to reflux for 30 min. The precipitate was filtered off, washed with CH$_2$Cl$_2$ and dried to give trans-2,2,2-trifluoro-N-(7-fluoro-2,3,4,14b-tetrahydro-1H-dibenzo[b,f]pyrido[1,2-d][1,4]oxazepin-1-yl)acetamide as an off-white solid (0.2 g, 25.6%). Data: (m/z)=381 (M+H)$^+$.

Example 6 trans-2,2,2-Trifluoro-N-(7-chloro-2,3,4,14b-tetrahydro-1H-dibenzo[b,f]pyrido[1,2-d][1,4]thiazepin-1-yl)acetamide (Structure 13 of Scheme II, where R1=H, R2=H, R3=Cl, R4=H, R5=H, R15=CF$_3$, X=S)

This compound was prepared by General Method 11, followed by chromatography on silica. Elution with toluene→toluene/ethyl acetate 95:5 followed by crystallisation from ether, which gave trans-2,2,2-trifluoro-N-(7-chloro-2,3,4,14b-tetrahydro-1H-dibenzo[b,f]pyrido[1,2-d][1,4]thiazepin-1-yl)acetamide as an off-white solid (3.0 mg, 12%). Data: (m/z)=413 (M+H)$^+$.

Example 7 trans-N-(7-Chloro-2,3,4,14b-tetrahydro-1H-dibenzo[b,f]pyrido[1,2-d][1,4]oxazepin-1-yl)-2-2-2-trifluoroacetamide (Structure 12 of Scheme II, where R1=H, R2=H, R3=Cl, R4=H, R5=H, R15=CF$_3$, X=O)

Successively, ethyl trifluoroacetate (1.41 mL, 11.8 mmol) and triethylamine (628 µL, 4.5 mmol) were added to trans-7-chloro-2,3,4,14b-tetrahydro-1H-dibenzo[b,f]pyrido[1,2-d][1,4]oxazepine-1-amine (291 mg, 0.97 mmol) in 11.8 mL of methanol. The resulting mixture was heated to 50° C. for 18 h. A precipitate was formed. The mixture was evaporated under reduced pressure to remove volatile reagents and 5 mL of methanol was added. After 30 min. stirring the precipitate was filtered off, washed with diethyl ether and dried to give trans-N-(7-chloro-2,3,4,14b-tetrahydro-1H-dibenzo[b,f]pyrido[1,2-d][1,4]oxazepin-1-yl)-2,2,2-trifluoroacetamide as an off-white solid (330 mg, 86%). Data: $^1$H-NMR (400 MHz, CDCl$_3$) 1.85 (m, 2H), 2.26 (m, 1H), 3.12 (m, 1H), 3.20 (m, 1H), 3.62 (dt, J=12.0, 4.0, 1H), 4.38 (d, J=8.0, 1H), 4.68 (m, 1H), 6.76 (dd, J=8.0, 3.0, 1H), 6.93 (d, J=3.0, 1H), 7.04 (d, J=8.0, 1H), 7.08 (dt, J=8.0, 2.0, 1H), 7.17 (dd, J=8.0, 2.0, 2H), 7.29 (dt, J=8.0, 2.0, 1H). (m/z)=397 (M+H)$^+$.

Example 8 trans-N-(7-Chloro-1,2,3,4,10,14b-hexahydrodibenzo[c,f]pyrido[1,2-a]azepin-1-yl)-2,2,2-trifluoroacetamide (Structure 12 of Scheme II, where R1=H, R2=H, R3=Cl, R4=H, R5=H, R15=CF$_3$, X=CH$_2$)

This compound was prepared by General Method 11, followed by chromatography on silica. Elution with toluene→toluene/ethyl acetate 95:5 gave trans-N-(7-chloro-1,2,3,4,10,14b-hexahydrodibenzo[c,f]pyrido[1,2-a]azepin-1-yl)-2,2,2-trifluoroacetamide (34.0 mg, 12%). Data: (m/z)=395 (M+H)$^+$.

Example 9 trans-N-(1,2,3,4,10,14b-Hexahydrodibenzo[c,f]pyrido[1,2-a]azepin-1-yl)-2,2,2-trifluoroacetamide (Structure 12 of Scheme II, where R1=H, R2=H, R3=H, R4=H, R5=H, R15=CF$_3$, X=—(CH$_2$)

This compound was prepared by General Method 11 starting from trans-1,2,3,4,10,14b-hexahydrodibenzo[c,f]pyrido[1,2-a]azepine-1-amine maleate, followed by chromatography on silica. Elution with toluene→toluene/ethyl acetate 9:1 gave trans-N-(1,2,3,4,10,14b-hexahydrodibenzo[c,f]pyrido[1,2-a]azepin-1-yl)-2,2,2-trifluoroacetamide (3.6 mg, 76%). Data: (m/z)=359 (M+H)$^+$.

Example 10 trans-N-(7-Chloro-2,3,4,14b-tetrahydro-1H-dibenzo[b,f]pyrido[1,2-d][1,4]oxazepin1-yl)acetamide (Structure 12 of Scheme II, where R1=R2=H, R3=Cl, R4=R5=H, R15=CH$_3$, X=O)

trans-7-Chloro-2,3,4,14b-tetrahydro-1H-dibenzo[b,f]pyrido[1,2-d][1,4]oxazepine-1-amine maleate (10 mg, 0.02 mmol), 50 µL of pyridine, and 25 µL of acetic anhydride in 1 mL of CH$_2$Cl$_2$ were stirred for 18 h at room temperature. The mixture was washed with 5% aqueous sodium bicarbonate and H$_2$O, dried (Na$_2$SO$_4$) and evaporated to give trans-N-(7-chloro-2,3,4,14b-tetrahydro-1H-dibenzo[b,f]pyrido[1,2-d][1,4]oxazepin1-yl)acetamide (9.0 mg, 65%). Data: (m/z)=343 (M+H)$^+$.

Example 11 trans-N-(7-Chloro-2,3,4,14b-tetrahydro-1H-dibenzo[b,f]pyrido[1,2-d][1,4]oxazepin-1-yl)-2-fluoroacetamide (Structure 12 of Scheme II, where R1=R2=H, R3=Cl, R4=R5=H, R15=CH$_2$F, X=O)

trans-7-Chloro-2,3,4,14b-tetrahydro-1H-dibenzo[b,f]pyrido[1,2-d][1,4]oxazepine-1-amine (10 mg, 0.03 mmol) was dissolved in 1 mL of ethyl fluoroacetate. The resulting mixture was heated to reflux for 2 h. Evaporation followed by crystallisation from methanol gave trans-N-(7-chloro-2,3,4, 14b-tetrahydro-1H-dibenzo[b,f]pyrido[1,2-d][1,4]oxazepin-1-yl)-2-fluoroacetamide (4.7 mg, 39%). Data: (m/z)=361 (M+H)+.

Example 12 trans-N-(7-Chloro-2,3,4,14b-tetrahydro-1H-dibenzo [b,f]pyrido[1,2-d][1,4]oxazepin-1-yl)-4-phenylbenzamide (Structure 12 of Scheme II, where R1=R2=H, R3=Cl, R4=R5=H, R15=C6H4C6H5, X=O)

General Method 12: N-acylation of an Amine of Structure 11 to an Amide of Structure 12.

DIPEA (18.6 µL, 0.14 mmol) and 4-phenylbenzoyl chloride (15.2 mg, 0.07 mmol) were added to a solution of trans-7-chloro-2,3,4,14b-tetrahydro-1H-dibenzo[b,f]pyrido[1,2-d][1,4]oxazepine-1-amine maleate (9.6 mg, 0.02 mmol) in 1 mL of CH2Cl2. The resulting mixture was stirred for 18 h at room temperature. The organic layer was washed with 5% aqueous sodium bicarbonate and H2O, dried (Na2SO4) and evaporated. Additional chromatography on silica (elution with toluene/ethyl acetate 9:1→toluene/ethyl acetate 1:1) gave trans-N-(7-chloro-2,3,4,14b-tetrahydro-1H-dibenzo[b,f]pyrido[1,2-d][1,4]oxazepin-1-yl)-4-phenylbenzamide (4.6 mg, 44%). Data: (m/z)=350 (M+H)+.

The following amides listed in Table 1 were prepared essentially by General Method 12, using the appropriate starting materials. For Example 15 triethylamine was used instead of DIPEA and the compound was crystallised from diethyl ether.

TABLE 1

| Ex | R1 | R2 | R3 | R4 | R5 | R6 | R7 | R15 | X | (m/z) | yield (%) |
|----|----|----|----|----|----|-----|----|------|---|-------|-----------|
| 13 | H | H | Cl | H | H | C(O)R15 | H | CHF2 | O | 379 | 35 |
| 14 | H | H | Cl | H | H | C(O)R15 | H | CH2Cl | O | 377 | 52 |
| 15 | H | H | Cl | H | H | C(O)R15 | H | CH2Br | O | 422 | 50 |

Example 16 trans-2-Amino-N-(7-chloro-2,3,4,14b-tetrahydro-1H-dibenzo[b,f]pyrido[1,2-d][1,4]oxazepin-1-yl) acetamide (Structure 12 of Scheme II, where R1=R2=H, R3=Cl, R4=R5=H, R15=CH2NH2, X=O)

Trans-7-chloro-2,3,4,14b-tetrahydro-1H-dibenzo[b,f]pyrido[1,2-d][1,4]oxazepin-1-yl)amino]carbonyl]methyl]carbamic Acid 1,1-dimethylethyl Ester General Method 13: N-acylation of an Amine of Structure 11 to an Amide of Structure 12.

DIPEA was added (pH=9) to trans-7-chloro-2,3,4,14b-tetrahydro-1H-dibenzo[b,f]pyrido[1,2-d][1,4]oxazepine-1-amine (10 mg, 0.03 mmol) in 1 mL of CH2Cl2 with HATU (12.5 mg, 0.03 mmol) and Boc-Gly-OH (10.3 mg, 0.03 mmol). The resulting mixture was stirred for 3 h, washed with 5% aqueous sodium bicarbonate and H2O, dried (Na2SO4) and evaporated to give [[[(trans-7-chloro-2,3,4,14b-tetrahydro-1H-dibenzo[b,f]pyrido[1,2-d][1,4]oxazepin-1-yl)amino]carbonyl]methyl]carbamic Acid 1,1-dimethylethyl Ester (14.3 mg, 100%). Data: (m/z)=405 (M+H)+.

trans-2-Amino-N-(7-chloro-2,3,4,14b-tetrahydro-1H-dibenzo[b,f]pyrido[1,2-d][1,4]oxazepin-1-yl)acetamide (Structure 12 of Scheme II, where R1=R2=H, R3=Cl, R4=R5=H, R15=CH2NH2, X=O)

trans-7-Chloro-2,3,4,14b-tetrahydro-1H-dibenzo[b,f]pyrido[1,2-d][1,4]oxazepin-1-yl)amino]carbonyl]methyl]carbamic acid 1,1-dimethylethyl ester (10 mg, 0.02 mmol) in 2 mL of ethyl acetate was purged with HCl gas at 0° C. for 2 h. The mixture was evaporated under reduced pressure to give trans-2-amino-N-(7-chloro-2,3,4,14b-tetrahydro-1H-dibenzo[b,f]pyrido[1,2-d][1,4]oxazepin-1-yl)acetamide (9.2 mg, 100%). Data: (m/z)=358 (M+H)+.

Example 17 trans-4-[(7-Chloro-2,3,4,14b-tetrahydro-1H-dibenzo [b,f]pyrido[1,2-d][1,4]oxazepin-1-yl)amino]-2,2,3,3-tetrafluoro-4-oxobutanoic Acid (Structure 12 of Scheme II, where R1=R2=H, R3=Cl, R4=R5=H, R15=CF2CF2C(O)OH, X=O)

Tetrafluorosuccinic anhydride (5.35 µL, 0.05 mmol) was added to trans-7-chloro-2,3,4,14b-tetrahydro-1H-dibenzo[b,f]pyrido[1,2-d][1,4]oxazepine-1-amine (10 mg, 0.03 mmol) in 1 mL of dioxane. The resulting mixture was stirred at room temperature for 30 minutes. Dioxane was removed by evaporation under reduced pressure and ethyl acetate and 2% citric acid were added. The organic layer was washed with brine, dried (Na2SO4) and evaporated to give trans-4-[(7-chloro-2,3,4,14b-tetrahydro-1H-dibenzo[b,f]pyrido[1,2-d][1,4]oxazepin-1-yl)amino]-2,2,3,3-tetrafluoro-4-oxobutanoic acid (10.6 mg, 51%). Data: (m/z)=472 (M+H)+.

Example 18 trans-N-(7-Chloro-2,3,4,14b-tetrahydro-1H-dibenzo [b,f]pyrido[1,2-d][1,4]oxazepin-1-yl)methanethioamide (Structure 13 of Scheme II, where R1=R2=H, R3=Cl, R4=R5=H, R15=H, X=O)

trans-N-(7-Chloro-2,3,4,14b-tetrahydro-1H-dibenzo[b,f]pyrido[1,2-d][1,4]oxazepin-1-yl)formamide trans-7-chloro-2,3,4,14b-tetrahydro-1H-dibenzo[b,f]pyrido[1,2-d][1,4]oxazepine-1-amine (10 mg, 0.03 mmol) was dissolved in 1 mL of ethyl formate. The resulting mixture was heated to reflux for 18 h. The cooled mixture was evaporated to give trans-N-(7-chloro-2,3,4,14b-tetrahydro-1H-dibenzo [b,f]pyrido[1,2-d][1,4]oxazepin-1-yl)formamide (12.0 mg, 100%). Data: (m/z)=329 (M+H)+.

trans-N-(7-Chloro-2,3,4,14b-tetrahydro-1H-dibenzo[b,f]pyrido[1,2-d][1,4]oxazepin-1-yl)methanethioamide (Structure 13 of Scheme II, where R1=R2=H, R3=Cl, R4=R5=H, R15=H, X=O)

General Method 14: Sulfonylation of an Amide of Structure 12 to a Thioamide of Structure 13.

Phosphorus pentasulfide (5 mg, 0.01 mmol) was added to trans-N-(7-chloro-2,3,4,14b-tetrahydro-1H-dibenzo[b,f]pyrido[1,2-d][1,4]oxazepin-1-yl)formamide (5 mg, 0.015 mmol) in dioxane. The resulting mixture was heated to reflux for 3 h. After evaporation under reduced pressure the crude compound was chromatographed on silica. Elution with toluene/ethyl acetate 85:15 gave trans-N-(7-chloro-2,3,4,14b-tetrahydro-1H-dibenzo[b,f]pyrido[1,2-d][1,4]oxazepin-1-yl) methanethioamide (2.8 mg, 51%). Data: (m/z)=345 (M+H)+.

The following thioamides listed in Table 2 were prepared essentially by General Method 14, using the appropriate starting materials. They are referred to as examples 19 through 27.

TABLE 2

| Ex | R1 | R2 | R3 | R4 | R5 | R6 | R7 | R15 | X | (m/z) | Yield (%) |
|---|---|---|---|---|---|---|---|---|---|---|---|
| 19 | H | H | Cl | H | H | C(S)R15 | H | $CF_3$ | O | 413 | 98 |
| 20 | H | H | Cl | H | H | C(S)R15 | H | $CF_3$ | $CH_2$ | 411 | 62 |
| 21 | H | H | Cl | H | H | C(S)R15 | H | $CH_3$ | O | 359 | 11 |
| 22 | H | H | Cl | H | H | C(S)R15 | H | $CH_2F$ | O | 378 | 63 |
| 23 | H | H | Cl | H | H | C(S)R15 | H | $CHF_2$ | O | 395 | 80 |
| 24 | H | H | Cl | H | H | C(S)R15 | $CH_3$ | $CF_3$ | O | 428 | 49 |
| 25 | H | H | H | H | H | C(S)R15 | H | $CF_3$ | O | 379 | 24 |
| 26 | H | H | Cl | Cl | H | C(S)R15 | H | $CF_3$ | O | 448 | 47 |
| 27 | H | H | Cl | H | H | C(S)R15 | H | $CH_2NH_2$ | O | 374 | 75 |

Example 28 trans-N-(7-Chloro-2,3,4,14b-tetrahydro-1H-dibenzo[b,f]pyrido[1,2-d][1,4]oxazepin-1-yl)-2,2,2-trifluoro-N-methylacetamide (Structure 14 of Scheme II, where R1=R2=Cl, R4=R5=H, R7=$CH_3$, R15=$CF_3$, X=O)

Sodium hydride (1.6 mg, 60% in oil) was added to trans-N-(7-chloro-2,3,4,14b-tetrahydro-1H-dibenzo[b,f]pyrido[1,2-d][1,4]oxazepin-1-yl)-2,2,2-trifluoroacetamide (15 mg, 0.04 mmol) in 1 mL of DMF. After 10 minutes stirring methyl iodide (2.47 µL, 0.04 mmol) was added. The resulting mixture was stirred at room temperature for 18 h. After evaporation the crude compound was purified by chromatography on silica. Elution with toluene/ethyl acetate 7:3 gave trans-N-(7-chloro-2,3,4,14b-tetrahydro-1H-dibenzo[b,f]pyrido[1,2-d][1,4]oxazepin-1-yl)-2,2,2-trifluoro-N-methylacetamide (14 mg, 90%). Data: (m/z)=411 (M+H)$^+$.

Example 29 trans-N-(7-Chloro-2,3,4,14b-tetrahydro-1H-dibenzo[b,f]pyrido[1,2-d][1,4]oxazepin-1-yl)-2,2,2-trifluoroacetimidamide (Structure 15 of Scheme II, where R1=H, R2=H, R3=Cl, R4=H, R5=H, R15=$CF_3$, X=O Trifluoroacetonitrile was added to a solution of trans-N-(7-chloro-2,3,4,14b-tetrahydro-1H-dibenzo[b,f]pyrido[1,2-d][1,4]oxazepin-1-yl)-2,2,2-trifluoroacetamide (10 mg, 0.03 mmol) in 2 mL of THF for 2 h. The mixture was stirred at room temperature for 16 hr. After evaporation the crude compound was chromatographed on silica. Elution with toluene gave trans-N-(7-chloro-2,3,4,14b-tetrahydro-1H-dibenzo[b,f]pyrido[1,2-d][1,4]oxazepin-1-yl)-2,2,2-trifluoroacetimidamide (7.14 mg, 55%). Data: (m/z)=396 (M+H)$^+$.

Example 30

Trans-(7-Chloro-2,3,4,14b-tetrahydro-1H-dibenzo[b,f]pyrido[1,2-d][1,4]oxazepin-1-yl)carbamic Acid Chloromethyl Ester (Structure 16 of Scheme III, where R1=R2=H, R3=Cl, R4=R5=H, R16=$CH_2Cl$, X=O)

General Method 15: N-acylation of an Amine of Structure 11 to a Carbamate of Structure 16.

100 µL of saturated aq. sodium bicarbonate was added to trans-7-chloro-2,3,4,14b-tetrahydro-1H-dibenzo[b,f]pyrido[1,2-d][1,4]oxazepine-1-amine (9.5 mg, 0.03 mmol) and chloromethyl chloroformate (64.2 µL, 0.42 mmol) in 250 µL of $CH_2Cl_2$. The resulting mixture was stirred at room temperature for 18 h. Subsequently, ethyl acetate was added and the organic layer was washed with water, dried ($Na_2SO_4$) and evaporated to give trans-(7-chloro-2,3,4,14b-tetrahydro-1H-dibenzo[b,f]pyrido[1,2-d][1,4]oxazepin-1-yl)carbamic acid chloromethyl ester (9.9 mg, 88%). Data: (m/z)=393 (M+H)$^+$.

Example 31 trans-(7-Chloro,2,3,4,14b-tetrahydro-1H-dibenzo[b,f]pyrido[1,2-d][1,4]oxazepin-1-yl)carbamic Acid 2-bromoethyl Ester (Structure 16 of Scheme III, where R1=R2=H, R3=Cl, R4=R5=H, R16=$CH_2CH_2Br$, X=O)

This compound was prepared by General Method 15 to afford trans-(7-chloro,2,3,4,14b-tetrahydro-1H-dibenzo[b,f]pyrido[1,2-d][1,4]oxazepin-1-yl)carbamic acid 2-bromoethyl ester (yield 80%). Data: (m/z)=452 (M+H)$^+$.

Example 32 trans-N-(7-Chloro-2,3,4,14b-tetrahydro-1H-dibenzo[b,f]pyrido[1,2-d][1,4]oxazepin-1-yl)-N'-(2-methylpropyl)thiourea (Structure 17 of Scheme III, where R1=R2=H, R3=Cl, R4=R5=H, R17=$CH_2CH(Me)_2$, X=O)

General Method 16: Isobutyl isothiocyanate (3.35 mg, 0.03 mmol) was added to trans-7-chloro-2,3,4,14b-tetrahydro-1H-dibenzo[b,f]pyrido[1,2-d][1,4]oxazepine-1-amine (5 mg, 0.02 mmol) in 1 mL of THF. The resulting mixture was stirred at room temperature for 18 h. The mixture was evaporated under reduced pressure. Crystallisation from methanol gave trans-N-(7-chloro-2,3,4,14b-tetrahydro-1H-dibenzo[b,f]pyrido[1,2-d][1,4]oxazepin-1-yl)-N'-(2-methylpropyl)thiourea (1 mg, 12%). Data: (m/z)=416 (M+H)$^+$.

The following thioureas listed in Table 3 were prepared essentially by General Method 16, using the appropriate starting materials. They are referred to as examples 33 through 35.

TABLE 3

| Ex | R1 | R2 | R3 | R4 | R5 | R6 | R7 | X | R17 | (m/z) | Yield(%) |
|---|---|---|---|---|---|---|---|---|---|---|---|
| 33 | H | H | Cl | H | H | C(S)NR17 | H | O | $cC_6H_{11}$ | 442 | 20 |
| 34 | H | H | Cl | H | H | C(S)NR17 | H | O | $CH_2CH=CH_2$ | 400 | 26 |
| 35 | H | H | Cl | H | H | C(S)NR17 | H | O | $C(Me)_3$ | 416 | 12 |

Example 36 trans-N-(2-Methylpropyl)-7-chloro-2,3,4,14b-tetrahydro-1H-dibenzo[b,f]pyrido[1,2-d][1,4]oxazepine-1-amine (Structure 18 of Scheme III, where R1=R2=H, R3=Cl, R4=R5=H, R18=CH(CH$_3$)$_2$, X=O)

General Method 17: N-alkylation of an Amine of Structure 11 to an N-alkyl of Structure 18.

After 10 min. stirring sodium triacetoxyborohydride (11 mg, 0.05 mmol) was added to trans-7-chloro-2,3,4,14b-tetrahydro-1H-dibenzo[b,f]pyrido[1,2-d][1,4]oxazepine-1-amine (10 mg, 0.03 mmol) and isobutyraldehyde (3.45 mg, 0.03 mmol) in 1 mL of CH$_2$Cl$_2$ (pH=4). The resulting mixture was stirred at room temperature for 18 h. The mixture was evaporated and chromatographed on silica. Elution with CH$_2$Cl$_2$/methanol 8:2 gave trans-N-(2-methylpropyl)-7-chloro-2,3,4,14b-tetrahydro-1H-dibenzo[b,f]pyrido[1,2-d][1,4]oxazepine-1-amine (13 mg, 100%). Data: (m/z)=357 (M+H)$^+$.

Example 37 trans-N-Propyl-7-chloro-2,3,4,14b-tetrahydro-1H-dibenzo[b,f]pyrido[1,2-d][1,4]oxazepine-1-amine (Structure 18 of Scheme III, where R1=R2=H, R3=Cl, R4=R5=H, R18=CH$_2$CH$_3$, X=O)

This compound was prepared by General Method 17 to afford trans-N-propyl-7-chloro-2,3,4,14b-tetrahydro-1H-dibenzo[b,f]pyrido[1,2-d][1,4]oxazepine-1-amine (10 mg, 97%). Data: (m/z)=343 (M+H)$^+$.

Examples 38A and B trans-N-(7,8-Dichloro-2,3,4,14b-tetrahydro-1H-dibenzo[b,f]pyrido[1,2-d][1,4]oxazepin-1-yl)-2,2,2-trifluoroacetamide (Example 38A) (Structure 19A of Scheme IV, where R1=H, R4=R5=H, R15=CF$_3$, X=O)

trans-N-(6,7-Dichloro-2,3,4,14b-tetrahydro-1H-dibenzo[b,f]pyrido[1,2-d][1,4]oxazepin-1-yl)-2,2,2-trifluoroacetamide (Example 38B) (Structure 19B of Scheme IV, where R1=R2=H, R5=H, R15=CF$_3$, X=O)

N-chlorosuccinimide (6.87 mg, 0.05 mmol) and 0.5 μL 1N HCl was added to trans-N-(7-chloro-2,3,4,14b-tetrahydro-1H-dibenzo[b,f]pyrido[1,2-d][1,4]oxazepin-1-yl)-2,2,2-trifluoroacetamide (20 mg, 0.05 mmol) in 102 μL of acetone. The resulting mixture was stirred at room temperature for 18 h. No reaction was observed. The reaction was repeated under the same conditions. The resulting mixture was stirred at room temperature for 1.5 h. The organic layer was washed with saturated aq. sodium bicarbonate and water, dried (Na$_2$SO$_4$) and evaporated and the crude compound was purified by preparative HPLC to give trans-N-(6,7-dichloro-2,3,4,14b-tetrahydro-1H-dibenzo[b,f]pyrido[1,2-d][1,4]oxazepin-1-yl)-2,2,2-trifluoroacetamide (3.6 mg, 17%) and trans-N-(7,8-dichloro-2,3,4,14b-tetrahydro-1H-dibenzo[b,f]pyrido[1,2-d][1,4]oxazepin-1-yl)-2,2,2-trifluoroacetamide (1.6 mg, 7%). Data: (m/z)=431 (M+H)$^+$.

Example 39 trans-N-(8-Bromo-7-chloro-2,3,4,14b-tetrahydro-1H-dibenzo[b,f]pyrido[1,2-d][1,4]oxazepin-1-yl)-2,2,2-trifluoroacetamide (Structure 20 of Scheme IV, where R1=H, R4=H, R5=H, R15=CF$_3$, X=O)

N-bromosuccinimide (9.2 mg, 0.05 mmol) and 0.5 μL of 1N HCl were added to trans-N-(7-chloro-2,3,4,14b-tetrahydro-1H-dibenzo[b,f]pyrido[1,2-d][1,4]oxazepin-1-yl)-2,2,2-trifluoroacetamide (20 mg, 0.05 mmol) in 512 μL of acetone. The resulting mixture was stirred at room temperature for 30 min. The mixture was diluted with ethyl acetate, washed with saturated aq. sodium bicarbonate and water, dried (Na$_2$SO$_4$) and evaporated to give trans-N-(8-bromo-7-chloro-2,3,4,14b-tetrahydro-1H-dibenzo[b,f]pyrido[1,2-d][1,4]oxazepin-1-yl)-2,2,2-trifluoroacetamide as a white solid (31 mg, 100%). Data: $^1$H-NMR (400 MHz, CDCl$_3$) 1.85 (m, 4H), 2.27 (m, 2H), 3.20 (m, 1H), 3.64 (m, 1H), 4.44 (d, J=8.0, 1H), 4.65 (m, 1H), 6.26 (b, 1H), 7.02 (s, 1H), 7.10 (dt, J=8.0, 2.0, 1H), 7.16 (m, 2H), 7.30 (dt, J=8.0, 3.0, 1H), 7.35 (s, 1H). (m/z)=477 (M+H)$^+$.

Example 40 trans-N-(2,3,4,14b-Tetrahydro-1H-dibenzo[b,f]pyrido[1,2-d][1,4]oxazepin-1-yl)-2,2,2-trifluoroacetamide (Structure 21 of Scheme IV, where R1=R2=R4=R5=H, R15=CF$_3$, X=O)

10 mg Pd/C 10% was added to a solution of trans-N-(7-chloro-2,3,4,14b-tetrahydro-1H-dibenzo[b,f]pyrido[1,2-d][1,4]oxazepin-1-yl)-2,2,2-trifluoroacetamide (100 mg, 0.25 mmol) in 5 mL of DMF. The suspension was shaken under H$_2$ atmosphere for 2 days. The mixture was filtered, poured into water and extracted with diethyl ether. The organic layer was washed with water, dried (Na$_2$SO$_4$) and evaporated to give trans-N-(2,3,4,14b-tetrahydro-1H-dibenzo[b,f]pyrido[1,2-d][1,4]oxazepin-1-yl)-2,2,2-trifluoroacetamide (89 mg, 98%). Data: $^1$H-NMR (400 MHz, CDCl$_3$) 1.85 (m, 3H), 2.99 (m, 1H), 3.18 (m, 1H), 3.75 (m, 1H), 4.50 (d, J=8,1H), 4.72 (m, 1H), 6.62 (br, 1H), 6.84-7.30 (8 arH). (m/z)=362 (M+H)$^+$.

Example 41 trans-N-(7-Chloro-8-nitro-2,3,4,14b-tetrahydro-1H-dibenzo[b,f]pyrido[1,2-d][1,4]oxazepin-1-yl)-2,2,2-trifluoroacetamide (Structure 22 of Scheme IV, where R1=H, R4=H, R5=H, R15=CF$_3$, X=O)

Nitric acid (50 μL, 1.10 mmol) was added at 0° C. to a suspension of trans-N-(7-chloro-2,3,4,14b-tetrahydro-1H- dibenzo[b,f]pyrido[1,2-d][1,4]oxazepin-1-yl)-2,2,2-trifluoroacetamide (210 mg, 0.53 mmol) in 4 mL of $CH_2Cl_2$. After stirring the mixture was extracted with ethyl acetate and the organic layer was washed with 5% aq. sodium bicarbonate, dried ($Na_2SO_4$) and evaporated to give trans-N-(7-chloro-8-nitro-2,3,4,14b-tetrahydro-1H-dibenzo[b,f]pyrido[1,2-d][1,4]oxazepin-1-yl)-2,2,2-trifluoroacetamide (219 mg, 90%). Data: $^1$H-NMR (400 MHz, DMSO) 1.64-1.94 (m, 3H), 2.05 (br, 1H), 3.26 (t, J=8.0, 1H), 4.20 (d, J=8.0, 1H), 4.35 (d, J=8.0, 1H), 4.60 (dq, J=8.0, 3.0, 1H) 7.15 (m, 1H), 7.11-9.21 (6 ArH). (m/z)=443 (M+H)$^+$.

Examples 42A and B trans-N-(6-Chloro-2,3,4,14b-tetrahydro-1H-dibenzo[b,f]pyrido[1,2-d][1,4]oxazepin-1-yl)-2,2,2-trifluoroacetamide (Example 42A) (Structure 23A of Scheme V, where R1=H, R4=R5=H, R15=$CF_3$, X=O)

trans-N-(8-Chloro-2,3,4,14b-tetrahydro-1H-dibenzo[b,f]pyrido[1,2-d][1,4]oxazepin-1-yl)-2,2,2-trifluoroacetamide (Example 42B) (Structure 23B of Scheme V, where R1=R2=R5=H, R15=$CF_3$, X=O)

N-chlorosuccinimide (8.52 mg, 0.06 mmol) and 0.67 µL of 1N HCl were added to trans-N-(2,3,4,14b-tetrahydro-1H-dibenzo[b,f]pyrido[1,2-d][1,4]oxazepin-1-yl)-2,2,2-trifluoroacetamide (21 mg, 0.06 mmol) in 1 mL of acetone. The resulting mixture was stirred at room temperature for 2 h. The mixture was poured into water and extracted with ethyl acetate. The organic layer was washed with saturated aq. sodium bicarbonate and evaporated. The crude compound was chromatographed on silica. Elution with heptane/ethyl acetate 8:2 gave the two compounds, one of which was trans-N-(6-chloro-2,3,4,14b-tetrahydro-1H-dibenzo[b,f]pyrido[1,2-d][1,4]oxazepin-1-yl)-2,2,2-trifluoroacetamide (9.8 mg, 41%). Data: $^1$H-NMR (400 MHz, $CDCl_3$) 1.84 (m, 3H), 2.22 (m, 1H), 3.17 (m, 1H), 3.52 (m, 1H), 4.44 (d, J=8.0, 1H), 4.69 (m, 1H), 6.48 (br, 1H), 6.90 (d, J=8.0, 1H), 6.97 (dd, J=8.0, 3.0, 1H), 7.10 (dt, J=8.0, 2.0, 1H), 7.13 (d, J=3.0, 1H), 7.19 (d, J=8.0, 2H), 7.29 (dt, J=8.0, 2.0, 1H). (m/z)=397 (M+H)$^+$.

The 8-chloro substituted compound containing 6,8-dichloro-substituted compound was purified by preparative HPLC to give trans-N-(8-chloro-2,3,4,14b-tetrahydro-1H-dibenzo[b,f]pyrido[1,2-d][1,4]oxazepin-1-yl)-2,2,2-trifluoroacetamide (1.2 mg, 5%). Data: $^1$H-NMR (400 MHz, $CDCl_3$) 1.84 (m, 3H), 2.00 (m, 1H), 2.93 (dd, J=8.0, 3.0, 1H), 3.28 (dt, J=8.0, 3.0, 1H), 4.39 (s, 1H), 4.89 (m, 1H), 7.07-7.33 (7 arH), 8.07 (br, 1H). (m/z)=397 (M+H)$^+$.

Example 43 trans-N-(7-Chloro-2,3,4,14b-tetrahydro-8-[bis(phenylsulfonyl)amino]-1H-dibenzo[b,f]pyrido[1,2-d][1,4]oxazepin-1-yl)-2,2,2-trifluoroacetamide (Structure 25 of Scheme VI, where R1=H, R4=H, R5=H, R11=R12=$S(O)_2Ph$, R15=$CF_3$, X=O)

trans-N-(8-Amino-7-chloro-2,3,4,14b-tetrahydro-1H-dibenzo[b,f]pyrido[1,2-d][1,4]oxazepin-1-yl)-2,2,2-trifluoroacetamide 80 µL 36% HCl and $SnCl_2.2H_2O$ (600 mg, 2.66 mmol) were added trans-N-(7-chloro-8-nitro-2,3,4,14b-tetrahydro-1H-dibenzo[b,f]pyrido[1,2-d][1,4]oxazepin-1-yl)-2,2,2-trifluoroacetamide (215 mg, 0.49 mmol) in 10 mL of ethanol. The resulting mixture was stirred at 60° C. for 18 h. After cooling the mixture was evaporated and dissolved in ethyl acetate. Aq. sodium bicarbonate was added to the solution (Sn salts were formed) followed by decalite and the mixture was filtered. The filtrate was extracted with ethyl acetate and the organic layer was washed with brine, dried ($Na_2SO_4$) and evaporated to give the title compound (194 mg, 82%). Data: (m/z)=413 (M+H)$^+$.

trans-2,2,2-Trifluoro-N-(7-chloro-2,3,4,14b-tetrahydro-8-[bis(phenylsulfonyl)amino]-1H-dibenzo[b,f]pyrido[1,2-d][1,4]oxazepin-1-yl)acetamide (Structure 25 of Scheme VI, where R1=H, R4=H, R5=H, R11=R12=$S(O)_2Ph$, R15=$CF_3$, X=O)

General Method 18: N-acylation of an amine of Structure 25 to an amide of Structure 26 Benzenesulfonyl chloride (5 µL, 0.04 mmol) was added under $N_2$ to trans-N-(8-amino-7-chloro-2,3,4,14b-tetrahydro-1H-dibenzo[b,f]pyrido[1,2-d][1,4]oxazepin-1-yl)-2,2,2,-trifluoroacetamide (5.0 mg, 0.01 mmol) in a mixture of 1 mL of $CH_2Cl_2$ and 25 µL of triethylamine. The resulting mixture was stirred at 40° C. for 4 h. After cooling the mixture was evaporated and the crude compound was purified by chromatography on silica. Elution with toluene/ethyl acetate 1:0→0:1 (gradient) gave trans-N-(7-chloro-2,3,4,14b-tetrahydro-8-[bis(phenylsulfonyl)amino]-1H-dibenzo[b,f]pyrido[1,2-d][1,4]oxazepin-1-yl)-2,2,2-trifluoroacetamide (7.3 mg, 83%). Data: (m/z)=692 (M+H)$^+$.

Example 44 trans-N-(7-Chloro-2,3,4,14b-tetrahydro-8-[bis(methylsulfonyl)amino]-1H-dibenzo[b,f]pyrido[1,2-d][1,4]oxazepin-1-yl)-2,2,2-trifluoroacetamide (Structure 25 of Scheme VI, where R1=H, R4=H, R5=H, R11=R12=$S(O)_2CH_3$, R15=$CF_3$, X=O)

This compound was prepared by General Method 18 using the appropriate starting material to afford trans-N-(7-chloro-2,3,4,14b-tetrahydro-8-[bis(methylsulfonyl)amino]-1H-dibenzo[b,f]pyrido[1,2-d][1,4]oxazepin-1-yl)-2,2,2-trifluoroacetamide (6.8 mg, 92%). Data: (m/z)=568 (M+H)$^+$.

Example 45 trans-N-(7-Chloro-2,3,4,14b-tetrahydro-8-[(phenylsulfonyl)amino]-1H-dibenzo[b,f]pyrido[1,2-d][1,4]oxazepin-1-yl)-2,2,2-trifluoroacetamide (Structure 25 of Scheme VI, where R1=H, R4=H, R5=H, R11=H, R12=$S(O)_2Ph$, R15=$CF_3$, X=O)

Benzenesulfonyl chloride (10 µL, 0.08 mmol) was added under $N_2$ to trans-N-(8-amino-7-chloro-2,3,4,14b-tetrahydro-1H-dibenzo[b,f]pyrido[1,2-d][1,4]oxazepin-1-yl)-2,2,2-trifluoroacetamide (5.0 mg, 0.01 mmol) in 1 mL of $CH_2Cl_2$ and 2 µL (1.1 eq) of triethylamine. The resulting mixture was stirred at 35° C. for 4 h. After cooling the mixture was evaporated and the crude compound was purified by chromatography on silica. Elution with toluene/ethyl acetate 1:0→0:1 (gradient) gave trans-N-(7-chloro-2,3,4,14b-tetrahydro-8-[(phenylsulfonyl)amino]-1H-dibenzo[b,f]pyrido[1,2-d][1,4]oxazepin-1-yl)-2,2,2-trifluoroacetamide (2.4 mg, 32%). Data: (m/z)=552 (M+H)$^+$.

Example 46 trans-N-(7-Chloro-2,3,4,14b-tetrahydro-1-(2,2,2-trifluoroacetylamino)1H-dibenzo[b,f]pyrido[1,2-d][1,4]oxazepin-8-yl)carbamic Acid 1,1-dimethylethyl Ester (Structure 25 of Scheme VI, where R1=H, R4=H, R5=H, R11=H, R12=C(O)OC(CH$_3$)$_3$, R15=CF$_3$, X=O)

Di-tert-butyl dicarbonate (20.55 mg, 0.09 mmol) was added at 5° C. under N$_2$ to trans-N-(8-amino-7-chloro-2,3,4,14b-tetrahydro-1H-dibenzo[b,f]pyrido[1,2-d][1,4]oxazepin-1-yl)-2,2,2-trifluoroacetamide (10.8 mg, 0.03 mmol) in 1 mL of THF and 6 µL (1.1 eq) of triethylamine. The resulting mixture was stirred at 50° C. for 72 h. After cooling the mixture was evaporated and chromatographed on silica. Elution with heptane/ethyl acetate 1:0→0:1 (gradient) gave the title compound (2.7 mg, 15%). Data: (m/z)=512 (M+H)$^+$.

Example 47 trans-N-(6,7-Dichloro-2,3,4,14b-tetrahydro-1H-dibenzo[b,f]pyrido[1,2-d][1,4]oxazepin-1-yl)acetamide (Structure 19B of scheme IV, where X=O, R1=H, R2=H, R5=H, R15=CH$_3$)

To a solution of trans-N-(7-chloro-2,3,4,14b-tetrahydro-1H-dibenzo[b,f]-pyrido[1,2-d][1,4]oxazepin1-yl)acetamide (Structure 12 of Scheme II, where R1=H, R2=H, R3=Cl, R4=R5=H, R15=CH$_3$, X=O) (0.63 g, 1.84 mmol) in acetone (15 mL) were added N-chlorosuccinimide (246 mg, 1.84 mmol) and 6N (aq) HCl (3.1 mL). The resulting suspension was stirred at room temperature for 20 h. A second amount of N-chlorosuccinimide (246 mg, 1.84 mmol) was added and subsequently the reaction mixture was stirred at room temperature for 4 h. The reaction mixture was extracted with ethyl acetate (3×), washed with sat. (aq) NaHCO$_3$ (3×), 10% (aq) NaCl (2×) and dried (Na$_2$SO$_4$). The solvents were removed under reduced pressure. The solid was purified by column chromatography (silicagel, toluene/ethanol=9/1). Subsequent purification by HPLC resulted in the title compound (137 mg, 36.4%). Data: $^1$H-NMR (400 MHz, CDCl$_3$) 1.55 (m, 1H), 1.82 (m, 2H), 1.94-2.20 (m, 1H), 2.10 (s, 3H), 2.92 (m, 1H), 3.11 (td, J=12.6, 4.2, 1H), 4.39 (d, J=1.9, 1H), 4.86 (m, 1H), 7.02-7.36 (m, 6 ArH).

Example 48 trans-7-Chloro-2,3,4,14b-tetrahydro-N-(2-methoxyethyl)-1H-dibenzo[b,f]pyrido[1,2-d][1,4]oxazepine-1-amine (Structure 26 of Scheme III, where R1=H, R2=H, R3=Cl, R4=H, R5=H)

To a solution of trans-7-chloro-2,3,4,14b-tetrahydro-1H-dibenzo[b,f]pyrido[1,2-d][1,4]oxazepine-1-amine (84 mg, 0.28 mmol) in DMF (400 µl) were added 2-methoxyethyl bromide (37 µl, 0.39 mmol) and triethylamine (47 µl, 0.36 mmol). The resulting reaction mixture was stirred at 60° C. for 18 h. After cooling down, ethyl acetate was added. The mixture was washed with sat. (aq) NaHCO$_3$ and water. The organic layer was dried and evaporated. The crude compound was purified with HPLC and freeze-dried to afford the title compound (32 mg, 32%). Data (m/z)=359 (M+H)$^+$.

Example 49

1,1-Dimetylethyl trans-2-[(7-chloro-2,3,4,14b-tetrahydro-1H-dibenzo[b,f]pyrido[1,2-d][1,4]thiazepin-1-yl)amino]acetate (Structure 27 of Scheme III, where R1=H, R2=H, R3=Cl, R4=H, R5=H)

To a solution of the HBr salt of trans-7-chloro-2,3,4,14b-tetrahydro-1H-dibenzo[b,f]pyrido[1,2-d][1,4]thiazepine-1-amine (200 mg, 0.5 mmol) in DMF (10 mL) was added DIPEA (219 µl, 1.3 mmol) and t-butyl bromoacetate (89 µl, 0.6 mmol). The reaction mixture was stirred at room temperature for 5.5 h. After pouring the reaction mixture into water it was extracted with ethyl acetate (3×). The combined organic layers were washed with brine, dried (Na$_2$SO$_4$) and evaporated. The crude product was purified on silica with heptane/ethyl acetate 8:2 to give the pure product (90 mg, 41%). Data: (m/z)=431 (M+H)$^+$.

Example 50 trans-N-(6,7-Dichloro-2,3,4,14b-tetrahydro-1H-dibenzo[b,f]pyrido[1,2-d][1,4]oxazepin-1-yl)formamide (Structure 29 of scheme VII)

trans-6,7-Dichloro-2,3,4,14b-tetrahydro-N-(2-methoxyethyl)-1H-dibenzo[b,f]pyrido[1,2-d][1,4]oxazepine-1-amine (Structure 28 of Scheme VII)

K$_2$CO$_3$ (537 mg, 3.9 mmol) was added to a solution of trans-N-(6,7-dichloro-2,3,4,14b-tetrahydro-1H-dibenzo[b,f]pyrido[1,2-d][1,4]oxazepin-1-yl)-2,2,2-trifluoroacetamide (322 mg, 0.75 mmol) in methanol (28 mL) and water (1.7 mL). The reaction mixture was stirred at reflux temperature for 2 h whereafter the methanol was removed under reduced pressure. Water was added to the remaining product and the water layer was extracted with CH$_2$Cl$_2$ (3×). The combined organic layers were washed with brine, dried (Na$_2$SO$_4$) and evaporated to give the crude title compound (266 mg, 100%).

trans-N-(6,7-Dichloro-2,3,4,14b-tetrahydro-1H-dibenzo[b,f]pyrido[1,2-d][1,4]oxazepin-1-yl)formamide (Structure 29 of scheme VII)

A solution of trans-6,7-dichloro-2,3,4,14b-tetrahydro-N-(2-methoxyethyl)-1H-dibenzo[b,f]pyrido[1,2-d][1,4]oxazepine-1-amine (122 mg, 0.36 mmol) in ethyl formate was stirred overnight at reflux temperature. After removal of the solvent under reduced pressure, the remaining product was purified with preparative LC-MS to give the title compound (40 mg, 30%). Data (m/z)=397 (M+H)$^+$.

Example 51 trans-N-(6-Bromo-2,3,4,14b-tetrahydro-1H-dibenzo[b,f]pyrido[1,2-d][1,4]oxazepin-1-yl)-2,2,2-trifluoroacetamide (Structure 36 of Scheme IX where X=O, R1=H, R2=H, R3=H, R4=Br, R5=H, R10=H)

2-[(2,6-Dibromophenyl)iminomethyl]phenol (Structure 30 of Scheme VIII where R2=H)

General Method 19: Formation of an Imine of Structure 30 Out of an Amine and an Aldehyde.

A solution of 2,6-dibromoaniline (9 g, 35.9 mmol), salicylaldehyde (2.79 mL, 35.9 mmol) and p-toluenesulfonic acid (20 mg, 0.1 mmol) in toluene (180 mL) was heated to reflux in a Dean-Stark apparatus for 2 h. After adding some triethylamine the reaction mixture was evaporated resulting in crude compound 2-[(2,6-dibromophenyl)iminomethyl]phenol (14 g, 100%).

9-Bromodibenzo[b,f][1,4]oxazepine (Structure 31 of Scheme VIII where X=O, R1=H, R2=H, R3=H, R4=Br, R5=H, R10=H)

General Method 20: Ring Closure by Etherification to Structure 31.

To a solution of 2-[(2,6-dibromophenyl)iminomethyl]phenol (14.1 g, 35.9 mmol) in 350 mL of DMSO, $K_2CO_3$ (9.9 g, 71.8 mmol) and 18-Crown-6 (95 mg, 0.36 mmol) were added. The resulting mixture was stirred at 140° C. for 1.5 h and was then allowed to cool to ambient temperature overnight. The mixture was poured into ice-water and extracted with ethyl acetate (3×). The organic solution was washed with water and brine, and subsequently dried ($MgSO_4$). Removal of the solvent in vacuo resulted in crude 9-bromodibenzo[b,f][1,4]oxazepine (9.79 g 99%). Data: (m/z)=274+276 $(M+H)^+$.

trans-6-Bromo-2,3,4,14b-tetrahydro-4-oxo-1H-dibenzo[b,f]pyrido[1,2-d][1,4]oxazepine-1-carboxylic Acid (Structure 32 of Scheme IX where X=O, R1=H, R2=H, R3=H, R4=Br, R5=H, R10=H)

General Method 21: Addition of Glutaric Anhydride to a Cyclic Amine, Resulting in the Formation of a Tetracycle of Structure 32.

Glutaric anhydride (5.22 g, 45.8 mmol) was added to a stirred solution of 9-bromo-dibenzo[b,f][1,4]oxazepine (9.29 g, 33.9 mmol) in xylene (9 mL). The mixture was heated to 140° C. for 72 h. Equal parts of ether and of ethyl acetate were added whereafter the product was collected by filtration. The crystals were dried at 50° C. under reduced pressure to yield the title compound as one isomer (5.5 g, 39%, trans). The eluent was extracted with 2N NaOH (aq.). By adding 3N HCl (aq.) to the aqueous layer the pH was adjusted to pH 2. The aqueous layer was extracted with ethyl acetate, washed with brine and dried. After removal of ethyl acetate under reduced pressure a mixture of isomers was obtained (6.1 g, 47%). Data: (m/z)=388+390 $(M+H)^+$.

(trans-6-Bromo-2,3,4,14b-tetrahydro-4-oxo-1H-dibenzo[b,f]pyrido[1,2-d][1,4]oxazepin-1-yl)carbamic Acid 1-ethylpropyl Ester (Structure 33 of Scheme IX where X=O, R1=H, R2=H, R3=H, R4=Br, R5=H, R10=H, R22=$CH(C_2H_5)_2$ General Method 22: Curtius Rearrangement and Subsequent Formation of a Carbamate of Structure 33.

To a solution of trans-6-bromo-2,3,4,14b-tetrahydro-4-oxo-1H-dibenzo[b,f]pyrido[1,2-d][1,4]oxazepine-1-carboxylic acid (5.1 g, 13.1 mmol) in toluene (185 mL), triethylamine (3.3 mL, 23.6 mmol) and DPPA (3.67 mL, 17.0 mmol) were added. The reaction mixture was heated to reflux for 1 h. Subsequently, 3-pentanol (2.8 mL, 26.2 mmol) was added and stirring was continued for 1.5 h at 110° C. After cooling down the reaction mixture was poured into ice-water, extracted with ethyl acetate, washed with water and brine, dried ($MgSO_4$) and evaporated, which resulted in the crude title compound (7.4 g, 100%). Data: (m/z)=473+475 $(M+H)^+$.

(trans-6-Bromo-2,3,4,14b-tetrahydro-1H-dibenzo[b,f]pyrido[1,2-d][1,4]oxazepin-1-yl)carbamic Acid 1-ethylpropyl Ester (Structure 34 of Scheme IX where X=O, R1=H, R2=H, R3=H, R4=Br, R5=H, R10=H, and R22=$CH(C_2H_5)_2$)

General Method 23: Formation of Structure 34 by Borane Reduction of an Amide Functionality.

Borane (1.0 M in THF, 60 mL, 60 mmol) was added dropwise to a stirred solution of trans-(6-bromo-2,3,4,14b-tetrahydro-4-oxo-1H-dibenzo[b,f]pyrido[1,2-d][1,4]oxazepin-1-yl)carbamic acid 1-ethylpropyl ester (7.4 g, 13.1 mmol) in THF (90 mL). The resulting mixture was stirred at ambient temperature for 1 h. Subsequently, hydrochloric acid (1N aq) was added dropwise until evolution of gas ceased. A solution of sodium hydroxide (2N aq) was added to the mixture to adjust the pH to 8. The resulting reaction mixture was extracted with ethyl acetate, and the extract was subsequently washed with water and brine. After drying ($MgSO_4$) the solvent was evaporated under reduced pressure to yield the crude title compound (7 g, 100%). Data: (m/z)=459+461 $(M+H)^+$.

trans-6-Bromo-2,3,4,14b-tetrahydro-1H-dibenzo[b,f]pyrido[1,2-d][1,4]oxazepin-1-ylamine (Structure 35 of Scheme IX, where X=O, R1=H, R2=H, R3=H, R4=Br, R5=H, R10=H)

General Method 24: Hydrolysis of an Amide Functionality, Resulting in an Amine of Structure 35.

A mixture of acetic acid (100 mL) and hydrogen bromide (48%, 50 mL) was added to trans-(6-bromo-2,3,4,14b-tetrahydro-1H-dibenzo[b,f]pyrido[1,2-d][1,4]-oxazepin-1-yl)carbamic acid 1-ethylpropyl ester and stirred for 1 h at 100° C. After cooling down the reaction mixture was poured into a cold 1N NaOH (aq) solution. It was extracted with ethyl acetate and the organic layer was washed with 1N NaOH (aq) 4×, sat. $NaHCO_3$ (aq), dried ($MgSO_4$) and the solvent was evaporated. The crude compound was purified on silica with toluene/acetone 9:1 to yield the title compound (2.4 g, 53%). Data: (m/z)=345+347 $(M+H)^+$.

trans-N-(6-Bromo-2,3,4,14b-tetrahydro-1H-dibenzo[b,f]pyrido[1,2-d][1,4]oxazepin-1-yl)-2,2,2-trifluoroacetamide (Structure 36 of Scheme IX, where X=O, R1=H, R2=H, R3=H, R4=Br, R5=H, R10=H)

General Method 25: Addition of Trifluoroacetic Anhydride to an Amine Yielding a Trifluoroacetamide of Structure 36.

To a solution of trans-6-bromo-2,3,4,14b-tetrahydro-1H-dibenzo[b,f]pyrido[1,2-d][1,4]oxazepin-1-ylamine (2.4 g, 6.95 mmol) in a mixture of $CH_2Cl_2$ (10 mL) and pyridine (10 mL), trifluoroacetic anhydride (5 mL, 35.4 mmol) was added. The resulting reaction mixture was stirred at ambient temperature for 0.5 h. Subsequently, water was added under cooling in an ice bath. The mixture was extracted with $CH_2Cl_2$ (2×). The combined organic layers were washed with brine, dried ($MgSO_4$), evaporated and stripped with toluene (2×) to give the title compound (1.54 g, 50%). Data: $^1$H-NMR (400 MHz, DMSO) 1.59-2.05 (m, 4H), 3.09-3.17 (m, 1H), 3.87 (d, J=14.0, 1H), 4.14 (d, J=10, 1H), 4.40-4.49 (m, 1H), 6.70-7.28 (m, 7 ArH), 9.13 (d, J=10, 1NH). (m/z)=441+443 $(M+H)^+$.

Example 52 trans-N-(6-Acetyl-2,3,4,14b-tetrahydro-1H-dibenzo[b,f]pyrido[1,2-d][1,4]oxazepin-1-yl)-2,2,2-trifluoroacetamide (Structure 37 of Scheme X, where R2=H)

General Method 26: Conversion of Bromide into an Acetyl of Structure 37.

(1-Ethoxyvinyl)-tributyl tin (182 µl, 0.54 mmol) was added to a solution of trans-N-(6-bromo-2,3,4,14b-tetrahydro-1H-dibenzo[b,f]pyrido[1,2-d][1,4]oxazepin-1-yl)-2,2,2-trifluoroacetamide (200 mg, 0.45 mmol) and $PdCl_2(PPh_3)_2$ (6 mg, 9 µmol) in toluene (12 mL) under $N_2$. The reaction mixture was heated to reflux and stirred for 3 h. 3 N (aq) HCl was added slowly at room temperature and the reacion mixture was stirred for a further ten minutes. It was then poured into water and extracted with ethyl acetate. The organic layer was washed with sat. $NaHCO_3$ (aq) and brine, dried ($MgSO_4$) and the solvents were evaporated. The crude product was purified, dissolved in THF (10 mL) and subsequently 3N HCl (aq) (4 mL) was added. The mixture was stirred at room temperature for 1 h, poured into water and extracted with ethyl acetate. The organic layer was washed with sat. NaHCO$_3$ and brine, dried and evaporated. After purification on HPLC the title compound was obtained (49 mg, 27%). Data: $^1$NMR (400 MHz, CDCl$_3$) 1.50 (m, 1H), 1.65-1.75 (m, 1H), 1.79-1.93 (m, 2H), 2.50 (d, J=3, 3H), 2.82 (m, 1H), 3.38 (dt, J=12, 4, 1H), 4.5 (d, J=3, 1H), 4.83 (m, 1H), 7.09-7.34 (7 ArH).

Example 53 trans-2,3,4,14b-Tetrahydro-1-[(trifluoroacetyl) amino]-1H-dibenzo[b,f]pyrido[1,2-d][1,4]oxazepine-6-carbonitrile (Structure 38 of Scheme X, where R2=H)

General Method 27: Conversion of a Bromide into a Cyano Derivative of Structure 38.

Copper(I) cyanide (142 mg, 1.6 mmol) was added to a solution of trans-N-(6-bromo-2,3,4,14b-tetrahydro-1H-dibenzo[b,f]pyrido[1,2-d][1,4]oxazepin-1-yl)-2,2,2-trifluoroacetamide (700 mg, 1.6 mmol) in 1-methyl-2-pyrrolidinone (28 mL) and heated to 200° C. and stirred for 24 h at 190° C. Water was added at room temperature and the mixture was extracted with ethyl acetate. The organic layer was washed with brine, dried (MgSO$_4$) and concentrated under reduced pressure. Purification on silica with heptane/ethyl acetate 1:1 gave the title compound (450 mg, 75%). Data: $^1$NMR (400 MHz, CDCl$_3$) 1.69-1.75 (m, 1H), 1.87-1.93 (m, 1H), 2.01-2.16 (m, 2H), 3.14-3.29 (m, 2H), 4.61 (d, J=3.2, 1H), 4.91 (m, 1H), 7.11-7.37 (7 ArH).

Example 54 trans-N-(6-Ethenyl-2,3,4,14b-tetrahydro-1H-dibenzo[b,f]pyrido[1,2-d][1,4]oxazepin-1-yl)-2,2,2-trifluoroacetamide (Structure 39 of Scheme X, where R2=H)

General Method 28: Conversion of a Bromide into a Vinyl Derivative of Structure 39.

To a solution of trans-N-(6-bromo-2,3,4,14b-tetrahydro-1H-dibenzo[b,f]pyrido-[1,2-d][1,4]oxazepin-1-yl)-2,2,2-trifluoroacetamide (50 mg, 0.11 mmol) in toluene (3 mL) was added PdCl$_2$(PPh$_3$)$_2$ and vinyltributyl tin (38 μl, 0.13 mmol). The resulting reaction mixture was heated to 110° C. and stirred for 2 h at 110° C. After cooling to room temperature, water was added and the mixture was extracted with ethyl acetate. The organic layer was washed with water and brine, dried (MgSO$_4$) and the solvent was evaporated. After purification by HPLC the title compound was obtained (23 mg, 52%). Data: $^1$NMR (400 MHz, CDCl$_3$) 1.60 (m, 1H), 1.78 (m, 1H), 1.83-1.96 (m, 2H), 2.93 (m, 1H), 3.43 (dt, J=12, 4, 1H), 4.35 (d, J=2.5, 1H), 4.84 (m, 1H), 5.40 (d, J=11, 1H), 5.67 (dd, J=18, 1.8, 1H), 7.07-7.31 (7 ArH), 7.55 (NH, 1H).

Example 55 trans-N-(2,3,4,14b-Tetrahydro-6-methoxy-1H-dibenzo[b,f]pyrido[1,2-d][1,4]oxazepin-1-yl)-2,2,2-trifluoroacetamide (Structure 41 of Scheme X, where R2=H)

Copper(I) iodide (21 mg, 0.11 mmol) was added to a stirring solution of trans-N-(6-bromo-2,3,4,14b-tetrahydro-1H-dibenzo[b,f]pyrido[1,2-d][1,4]oxazepin-1-yl)-2,2,2-trifluoroacetamide (100 mg, 0.22 mmol) in DMF (1.5 mL) in a Dean-Stark apparatus. Subsequently a solution of NaOMe (1.2 mL, 1.2 mmol) in methanol was added and stirring was continued at 135° C. for 4 h. After cooling down, the reaction mixture was poured into sat (aq) NH$_4$Cl and extracted with ethyl acetate. The organic layer was washed with brine, dried (MgSO$_4$) and evaporated. After purification on a SPE-column and by HPLC the title compound (11 mg, 13%) was obtained. Data: $^1$H-NMR (400 MHz, CDCl$_3$) 1.50 (m, 1H), 1.76 (m, 1H), 1.87 (m, 1H), 1.94 (m, 1H), 2.87 (m, 1H), 3.29 (dt, J=12, 3.2, 1H), 3.86 (s, 3H), 4.28 (d, J=3.2, 1H), 4.81 (m, 1H), (Ar) 6.66 (d, J=12, 1H), 6.78 (d, J=12, 1H), 7.10 (m, 1H), 7.20-7.31 (m, 4H), 8.18 (m, 1H, NH).

Example 56 trans-N-(6-Bromo-8-fluoro-2,3,4,14b-tetrahydro-1H-dibenzo[b,f]pyrido[1,2-d][1,4]oxazepin-1-yl)-2,2,2-trifluoroacetamide (Structure 36 of Scheme IX where X=O, R1=H, R2=F, R3=H, R4=Br, R5=H, R10=H)

2-[(2,6-Dibromo-4-fluorophenyl)iminomethyl]phenol (Structure 30 of Scheme VIII where R2=F)

This compound was prepared by general method 19 to afford the crude title compound (15.2 g, 100%). Data: (m/z)= 372+374+376 (M+H)$^+$.

9-bromo-7-fluorodibenzo[b,f][1,4]oxazepine (Structure 31 of Scheme VIII where X=O, R1=H, R2=F, R3=H, R4=Br, R5=H, R10=H)

This compound was prepared by general method 20. 9-Bromo-7-fluorodibenzo[b,f][1,4]oxazepine (6.7 g, 64%) was collected by filtration after pouring the reaction mixture into ice-water. Data: (m/z)=292+294 (M+H)$^+$.

trans-6-Bromo-8-fluoro-2,3,4,14b-tetrahydro-4-oxo-1H-dibenzo[b,f]pyrido[1,2-d][1,4]oxazepine-1-carboxylic Acid (Structure 32 of Scheme IX where X=O, R1=H, R2=F, R3=H, R4=Br, R5=H, R10=H)

This compound was prepared by general method 21 to afford the title compound as crystals of only one isomer (4.2 g, 45%). Data: (m/z)=406+408 (M+H)$^+$.

(trans-6-Bromo-8-fluoro-2,3,4,14b-tetrahydro-4-oxo-1H-dibenzo[b,f]pyrido[1,2-d][1,4]oxazepin-1-yl)carbamic Acid 1-ethylpropyl Ester (Structure 33 of Scheme IX where X=O, R1=H, R2=F, R3=H, R4=Br, R5=H, R10=H) This compound was prepared by general method 22 to afford the title compound (4.6 g, 100%). Data: (m/z)=435+437 (M+H)$^+$.

(trans-6-Bromo-8-fluoro-2,3,4,14b-tetrahydro-1H-dibenzo[b,f]pyrido[1,2-d][1,4]oxazepin-1-yl)carbamic Acid 1-ethylpropyl Ester (Structure 34 of Scheme IX where X=O, R1=H, R2=F, R3=H, R4=Br, R5=H, R10=H)

This compound was prepared by general method 23. The product (1.2 g, 30%) was obtained by crystallisation from diethyl ether. Data: (m/z)=421+423 (M+H)$^+$.

trans-6-Bromo-8-fluoro-2,3,4,14b-tetrahydro-1H-dibenzo[b,f]pyrido[1,2-d][1,4]oxazepine-1-amine (Structure 35 of Scheme IX, where X=O, R1=H, R2=F, R3=H, R4=Br, R5=H, R10=H)

This compound was prepared by general method 24 to afford the pure title compound (2.1 g, 72%) after purification on a SPE column. Data: (m/z)=363+365 (M+H)$^+$.

trans-N-(6-Bromo-8-fluoro-2,3,4,14b-tetrahydro-1H-dibenzo[b,f]pyrido[1,2-d][1,4]oxazepin-1-yl)-2,2,2-trifluoroacetamide (Structure 36 of Scheme IX, where X=O, R1=H, R2=F, R3=H, R4=Br, R5=H, R10=H)

This compound was prepared by general method 25 to afford the title compound. After purification with HPLC 79 mg (91%) was obtained. Data: $^1$H-NMR (400 MHz, CDCl$_3$) 1.54-1.61 (m, 1H), 1.67-1.77 (m, 1H), 1.82-1.90 (m, 1H), 1.93-2.06 (m, 1H), 2.85-2.92 (dd, J=12.2, J=5.0, 1H), 3.27-3.35 (td, J=12.0, J=3.0, 1H), 4.33-4.35 (d, J=2.2, 1H), 4.87-4.92 (m, 1H), 6.88-7.34 (6 ArH), (br, 1H). (m/z)=459+461 (M+H)$^+$.

Example 57 trans-N-(6-Acetyl-8-fluoro-2,3,4,14b-tetrahydro-1H-dibenzo[b,f]pyrido[1,2-d][1,4]oxazepin-1-yl)-2,2,2-trifluoroacetamide (Structure 37 of Scheme X, where R2=F)

This compound was prepared by general method 26 to afford the title compound (103 mg, 42.9%) after purification by HPLC. Data: $^1$H-NMR (400 MHz, CDCl$_3$) 1.46-1.69 (m, 2H), 1.76-1.93 (m, 2H), 2.58 (s, 3H), 2.76-2.82 (m, 1H), 3.34-3.43 (td, J=12.0, 3.2, 1H), 4.44-4.47 (d, J=2.2, 1H), 4.80-4.86 (m, 1H), 6.99-7.32 (6 ArH), 8.5-8.58 (br, 1H). (m/z)=423 (M+H)$^+$.

Example 58 trans-8-Fluoro-2,3,4,14b-tetrahydro-1-[(trifluoroacetyl)amino]-1H-dibenzo[b,f]pyrido-[1,2-d][1,4]oxazepine-6-carbonitrile (Structure 38 of Scheme X, where R2=F)

This compound was prepared by general method 27. After purification by HPLC the title compound (78 mg, 55.7%, trans) was obtained. Data: $^1$H-NMR (400 MHz, CDCl$_3$) 1.65-1.72 (m, 1H), 1.85-1.92 (m, 1H), 1.95-2.02 (m, 1H), 2.05-2.14 (m, 1H), 3.06-3.11 (m, 1H), 3.17-3.23 (td, J=8.0, J=2.0, 1H), 4.55-4.57 (d, J=1.7, 1H), 4.90-4.94 (m, 1H), 7.06-7.36 (6 ArH), 7.47-7.56 (br, 1H). (m/z)=406 (M+H)$^+$.

Example 59 trans-N-(6-Ethenyl-8-fluoro-2,3,4,14b-tetrahydro-1H-dibenzo[b,f]pyrido[1,2-d][1,4]-oxazepin-1-yl)-2,2,2-trifluoroacetamide (Structure 39 of scheme X, where R2=F)

This compound was prepared by general method 28 to afford the title compound (141 mg, 53%) after purification on HPLC. Data: $^1$H-NMR (400 MHz, CDCl$_3$) 1.57-1.77 (m, 2H), 1.82-1.95 (m, 2H), 2.86-2.92 (m, 1H), 3.40-3.48 (td, J=12.0, J=3.0, 1H), 4.27-4.30 (d, J=2.5, 1H), 4.82-4.87 (m, 1H), 5.43-5.47 (d, J=11.4, 1H), 5.64-5.70 (dd, J=18.0, 1.1, 1H), 6.81-7.32 (6 ArH+1H), 7.49-7.57 (br, 1H). (m/z)=407 (M+H)$^+$.

Example 60 trans-2,2,2-Trifluoro-N-(8-fluoro-2,3,4,14b-tetrahydro-6-methyl-1H-dibenzo[b,f]pyrido-[1,2-d][1,4]oxazepin-1-yl)acetamide (Structure 40 of Scheme X, where R2=F)

To a solution of trans-N-(6-bromo-8-fluoro-2,3,4,14b-tetrahydro-1H-dibenzo[b,f]pyrido[1,2-d][1,4]oxazepin-1-yl)-2,2,2-trifluoroacetamide (300 mg, 0.65 mmol) in THF (7 mL) was added ferrocene PdCl$_2$ (10 mg, 14 mmol) and the reaction mixture was stirred for 10 min. Methylzinc chloride (0.81 mL) was added dropwise whereafter the reaction mixture was heated to 60° C. After 3 h ferrocene PdCl$_2$ (20 mg, 28 μmol) and methylzinc chloride (0.3 mL) were added and the reaction mixture was heated at 80° C. for another hour. Water was added at room temperature, and the reaction mixture was extracted with ether and water. The ether solution was washed with brine, dried (Na$_2$SO$_4$) and the volatiles were removed under reduced pressure. After purification by HPLC the title compound was obtained (108 mg, 39%). Data: $^1$H-NMR (400 MHz, CDCl$_3$) 1.56-1.72 (m, 2H), 1.79-1.93 (m, 2H), 2.37 (s, 3H), 2.79-2.86 (m, 1H), 3.44-3.52 (td, J=12.0, J=3.0, 1H), 4.27-4.29 (d, J=2.5, 1H), 4.85-4.91 (m, 1H), 6.70-7.32 (6 ArH), 7.63-7.70 (br, 1H). (m/z)=395 (M+H)$^+$.

Example 61 trans-N-(7-Bromo-2,3,4,14b-tetrahydro-1H-dibenzo[b,f]pyrido[1,2-d][1,4]oxazepin-1-yl)-2,2,2-trifluoroacetamide (Structure 46 of Scheme XI)

4-Bromo-2-nitro-1-phenoxybenzene (Structure 42 of Scheme XI)

Cs$_2$CO$_3$ (4 g, 12.3 mmol) was added to a solution of phenol (1 g, 10.6 mmol) in 50 mL of THF under N$_2$ atmosphere. After stirring for 15 min. 1,4-dibromo-2-nitrobenzene (2.81 g, 10 mmol) was added. The resulting mixture was heated to reflux and stirred overnight at reflux. Water and ethyl acetate were added, followed by extraction with ethyl acetate (3×). The combined organic layers were washed with water and brine, dried (Na$_2$SO$_4$) and evaporated to give the crude compound (3.2 g, 75%).

5-Bromo-2-phenoxybenzeneamine (Structure 43 of Scheme XI)

Iron powder (3 g, 53.4 mmol) and acetic acid (10 mL) were added to a stirred suspension of 4-bromo-2-nitro-1-phenoxybenzene (3.1 g, 9.5 mmol) in water (25 mL) of 60° C. The reaction mixture was heated to 80° C. and stirred for 30 min. After cooling to room temperature the reaction mixture was filtered and extracted with toluene. The toluene solution was washed with water (3×) and brine, dried (Na$_2$SO$_4$) and evaporated to give the crude compound (2.3 g, 87%). Data: (m/z)= 264+266 (M+H)$^+$.

N-(5-Bromo-2-phenoxyphenyl)formamide (Structure 44 of Scheme XI)

General Method 29: Addition of Formic Acid to an Amine Yielding Formamides of Structure 44.

A mixture of 5-bromo-2-phenoxybenzeneamine (68.4 g, 260 mmol) and formic acid (180 mL) was heated to reflux and stirred for 2 h. The product was collected by filtration and dried at 50° C. under reduced pressure to give the compound as off-white crystals (60 g, 79%). Data: (m/z)=292+294 (M+H)$^+$.

8-Bromodibenzo[b,f][1,4]oxazepine (Structure 45 of Scheme XI)

General Method 30: Ring Closure with PPA Resulting in Derivatives of Structure 45.

PPA (207.5 g) was added to N-(5-bromo-2-phenoxyphenyl)formamide (20 g, 68.7 mmol) and the reaction mixture was heated to 140° C. with vigorous stirring for 2 h. After cooling to room temperature the reaction mixture was poured into ice-water. The mixture was filtered and the solid was washed with water and with 25% ammonia and dried at 50° C. under reduced pressure to yield the title compound (9.9 g, 52%). Data: (m/z)=274+276 (M+H)$^+$.

trans-7-Bromo-2,3,4,14b-tetrahydro-4-oxo-1H-dibenzo[b,f]pyrido[1,2-d][1,4]oxazepine-1-carboxylic Acid (Structure 32 of Scheme IX where X=O, R1=H, R2=H, R3=Br, R4=H, R5=H, R10=H)

Glutaric anhydride (5.48 g, 48.1 mmol) was added to a stirred solution of 8-bromodibenzo[b,f][1,4]oxazepine (8.1 g, 29.6 mmol) in xylene (20 mL). $CH_2Cl_2$ was added to the reaction mixture and this was extracted with 2N (aq) NaOH (3x). All aqueous layers were neutralized by adding 2N (aq) HCl and extracted with $CH_2Cl_2$. The combined organic layers were dried ($Na_2SO_4$) and evaporated resulting in the title compound (9.7 g, 85%) as a mixture of trans and cis. Data: (m/z)=388+390 $(M+H)^+$.

trans-(7-Bromo-2,3,4,14b-tetrahydro-4-oxo-1H-dibenzo[b,f]pyrido[1,2-d][1,4]oxazepin-1-yl)carbamic Acid 1-ethylpropyl Ester (Structure 33 of Scheme IX where X=O, R1=H, R2=H, R3=Br, R4=H, R5=H, R10=H, R22=$CH(C_2H_5)_2$)

By applying general method 22 and by using 3-pentanol as alcohol, the title compound was obtained (6.0 g, 99%). Data: (m/z)=470+472 $(M+H)^+$.

trans-(7-Bromo-2,3,4,14b-tetrahydro-1H-dibenzo[b,f]pyrido[1,2-d][1,4]oxazepin-1-yl)carbamic Acid 1-ethylpropyl Ester (Structure 34 of Scheme IX where X=O, R1=H, R2=H, R3=Br, R4=H, R5=H, R10=H, R22=$CH(C_2H_5)_2$)

Borane (1.0 M in THF, 55 mL, 55 mmol) was added dropwise to a stirred solution of trans-(7-bromo-2,3,4,14b-tetrahydro-4-oxo-1H-dibenzo[b,f]pyrido[1,2-d][1,4]oxazepin-1-yl)carbamic acid 1-ethylpropyl ester (6.01 g, 12.7 mmol) in THF (63 mL). The resulting mixture was stirred at ambient temperature for 1 h. Subsequently, water was added and the resulting mixture was extracted with ethyl acetate. The organic layers were washed with water and brine, dried ($Na_2SO_4$) and evaporated. The crude product was chromatographed on silica with heptane/ethyl acetate 1:1 which gave the title product as a mixture of cis and trans. After adding ethyl acetate to this mixture, pure trans product (1.41 g, 24.2%) could be collected through filtration. Data: (m/z)= 459+461 $(M+H)^+$.

trans-7-Bromo-2,3,4,14b-tetrahydro-1H-dibenzo[b,f]pyrido[1,2-d][1,4]oxazepine-1-amine (Structure 35 of Scheme IX where X=O, R1=H, R2=H, R3=Br, R4=H, R5=H, R10=H)

This compound was prepared by general method 24 to afford the title compound (1.05 g, 99%). Data: (m/z)=345+ 347 $(M+H)^+$.

trans-N-(7-Bromo-2,3,4,14b-tetrahydro-1H-dibenzo[b,f]pyrido[1,2-d][1,4]oxazepin-1-yl)-2,2,2-trifluoroacetamide (Structure 46 of Scheme XI)

This compound was prepared by general method 25 to afford the title compound (76 mg, 92%). Data: $^1$H-NMR (400 MHz, DMSO) 1.58-2.09 (m, 4H), 3.08 (t, J=12.8, 1H), 3.81 (d, J=14.0, 1H), 4.11 (d, J=10.4, 1H), 4.38 (m, 1H), 6.83-7.28 (7 ArH), 9.13 (d, J=10.0, 1H), (m/z)=441+443 $(M+H)^+$.

Example 62 trans-N-(7-Acetyl-2,3,4,14b-tetrahydro-1H-dibenzo[b,f]pyrido[1,2-d][1,4]oxazepin-1-yl)-2,2,2-trifluoroacetamide (Structure 47 of Scheme XII)

(1-Ethoxyvinyl)tributyl tin (90 μl, 0.23 mmol) was added to a solution of trans-N-(7-bromo-2,3,4,14b-tetrahydro-1H-dibenzo[b,f]pyrido[1,2-d][1,4]oxazepin-1-yl)-2,2,2-trifluoroacetamide (100 mg, 0.23 mmol) and $PdCl_2(PPh_3)_2$ (3 mg, 4.3 μmol) in toluene (6 mL) under $N_2$. The reaction mixture was heated to 140° C. and stirred for 3 h. After cooling to room temperature, 2N (aq) HCl (450 ul) was added and the reaction mixture was stirred for 1 h. The reaction was quenched with sat $NaHCO_3$ (aq) and extracted with ethyl acetate. The organic layer was washed with brine, dried ($Na_2SO_4$) and evaporated. The crude compound was chromatographed with heptane/ethyl acetate 1:1. Purifcation by HPLC gave the title compound (43 mg, 47%). Data: $^1$H-NMR (400 MHz, DMSO) 1.60-2.09 (m, 4H), 3.21 (t, J=11.2, 1H), 3.90 (d, J=14.0, 1H), 4.16 (d, J=10.4, 1H), 4.44 (m, 1H), 7.04-7.54 (m, 10H), 9.20 (d, J=10.0, 1H). (m/z)=405 $(M+H)^+$.

Example 63 trans-2,3,4,14b-Tetrahydro-1-[(trifluoroacetyl)amino]-1H-dibenzo[b,f]pyrido[1,2-d][1,4]oxazepine-7-carbonitrile (Structure 48 of Scheme XII)

This compound was generated by general method 27 to afford the title compound (491 mg, 50%). Data: $^1$H-NMR (400 MHz, DMSO) 1.58-2.09 (m, 4H), 3.16 (t, J=13.2, 1H), 3.96 (d, J=13.6, 1H), 4.18 (d, J=10.4, 1H), 4.47 (m, 1H), 7.06-7.53 (m, 7 ArH), 9.18 (d, J=9.6, 1H). (m/z)=388 $(M+H)^+$.

Example 64 trans-N-(7-Ethenyl-2,3,4,14b-tetrahydro-1H-dibenzo[b,f]pyrido[1,2-d][1,4]oxazepin-1-yl)-2,2,2-trifluoroacetamide (Structure 49 of Scheme XII)

This compound was generated by general method 28 to afford the title compound (15 mg, 34%). Data: $^1$H-NMR (400 MHz, DMSO) 1.59-2.07 (m, 4H), 3.14 (t, J=12, 1H), 3.90 (d, J=13.6, 1H), 4.23 (d, J=10.0, 1H), 4.44 (m, 1H), 5.15 (d, J=12.0, 1H) 5.50 (d, J=18.4, 1H) 6.60 (q, 1H) 6.84-7.26 (m, 7 ArH), 9.17 (d, J=9.6, 1H). (m/z)=389 $(M+H)^+$.

Example 65 trans-2,2,2-trifluoro-N-[2,3,4,14b-tetrahydro-7-[(phenylmethyl)amino]-1H-dibenzo[b,f]pyrido[1,2-d][1,4]oxazepin-1-yl]acetamide (Structure 50 of Scheme XII)

To a solution of trans-N-(7-bromo-2,3,4,14b-tetrahydro-1H-dibenzo[b,f]pyrido[1,2-d][1,4]-oxazepin-1-yl)-2,2,2-trifluoroacetamide (0.5 g, 1.1 mmol) in DME (16 mL), $Pd_2(dba)_3$ (12.5 mg, 13.5 μmol), 2-(di-t-butyl-phosphino)biphenyl (25 mg, 80 μmol), sodium-tert-butoxide (218 mg, 2.3 mmol) and benzylamine (243 mg, 2.3 mmol) were added. The resulting reaction mixture was heated to 75° C. and stirred at this temperature for 48 h. The reaction mixture was quenched with sat $NaHCO_3$ (aq) and extracted with ethyl acetate. The organic layer was washed with water and brine, dried ($Na_2SO_4$) and evaporated. The crude product was chromatographed with heptane/ethyl acetate 8:2 and purified with HPLC to afford the title compound (21 mg, 32%). Data: $^1$H-NMR (400 MHz, DMSO) 1.54-2.02 (m, 4H), 2.95 (t, J=9.2, 1H), 3.68 (d, J=14.0, 1H), 4.02 (d, J=10.0, 1H), 4.17 (d, J=6.0, 2H), 4.37 (m, 1H), 5.90-7.33 (12 ArH, 1 NH), 9.11 (d, J=10.0, 1H). (m/z)=468 $(M+H)^+$.

Example 66 trans-N-(7-Amino-2,3,4,14b-tetrahydro-1H-dibenzo[b,f]pyrido[1,2-d][1,4]oxazepin-1-yl)-2,2,2-trifluoroacetamide (Structure 51 of Scheme XII)

To a solution of trans-2,2,2-trifluoro-N-[2,3,4,14b-tetrahydro-7-[(phenylmethyl)amino]-1H-dibenzo[b,f]pyrido[1,2-d][1,4]oxazepin-1-yl]acetamide (944 mg, 2.0 mmol) in ethanol (16 mL) were added Pd/C 10% (111 mg) and a solution of 4M HCl in dioxane (778 µl, 3.11 mmol). The resulting reaction mixture was hydrogenated at 3 bar for 6 h. The reaction mixture was quenched with sat. NaHCO$_3$ (aq) and diluted with ethanol. After filtration through dicalite and thorough washing with ethyl acetate, the volatiles were removed in vacuo. A part of the crude product was purified with HPLC to afford the title compound (29 mg, 53%). Data (m/z)=378 (M+H)$^+$.

Example 67 trans-N-[2,3,4,14b-Tetrahydro-7-[(1-oxopropyl)amino]-1H-dibenzo[b,f]pyrido[1,2-d][1,4]oxazepin-1-yl]-2,2,2-trifluoroacetamide (Structure 52 of Scheme XII)

To a solution of trans-N-(7-amino-2,3,4,14b-tetrahydro-1H-dibenzo[b,f]pyrido-[1,2-d][1,4]oxazepin-1-yl)-2,2,2-trifluoroacetamide (50 mg, 0.13 mmol) in CH$_2$Cl$_2$ (2 mL) was added propionyl chloride (11 µl, 0.13 mmol) and triethylamine (20 µl, 0.14 mmol). The reaction mixture was stirred for 1.5 h at room temperature. The reaction mixture was quenched with sat. NaHCO$_3$ (aq) and extracted with CH$_2$Cl$_2$. The organic layer was dried and evaporated. The crude product was purified on silica and by HPLC to afford the title compound (27 mg, 48%). Data (m/z)=434 (M+H)$^+$.

Example 68 trans-N-(12-Bromo-7-chloro-2,3,4,14b-tetrahydro-1H-dibenzo[b,f]pyrido[1,2-d][1,4]oxazepin-1-yl)-2,2,2-trifluoroacetamide (Structure 55 of Scheme XIII)

4-Bromo-2-[(4-bromo-2-fluorophenyl)methyleneamino]phenol (Structure 53 of Scheme XIII)

5-Chloro-2-hydroxyaniline (9.8 g, 48 mmol) and 4-bromo-2-fluorobenzaldehyde (7.0 g, 48 mmol) were dissolved in ethanol (400 mL). The reaction mixture was heated to 60° C. and stirred for 1 h. Subsequently the ethanol was evaporated and the title compound was obtained (17.4 g, 100%).

3-Bromo-8-chlorodibenzo[b,f][1,4]oxazepine (Structure 54 of Scheme XIII)

To a solution of 4-bromo-2-[(4-bromo-2-fluorophenyl)methyleneamino]phenol (17.4 g, 48.5 mmol) in DMSO (200 mL) was added K$_2$CO$_3$ (13.4 g, 97.1 mmol). The resulting reaction mixture was stirred at 140° C. for 1 h. Water was added at 45° C. The product was collected by filtration as an off-white solid. The solid was washed with water, dissolved in ethyl acetate and washed with sat. (aq) NaCl and dried (Na$_2$SO$_4$). The volatiles were evaporated to give the title compound (14.3 g, 95.5%).

trans-12-Bromo-7-chloro-2,3,4,14b-tetrahydro-4-oxo-1H-dibenzo[b,f]pyrido[1,2-d][1,4]oxazepine-1-carboxylic Acid (Structure 32 of Scheme IX where X=O, R1=H, R2=H, R3=Cl, R4=H, R5=12-Br, R10=H)

This compound was prepared by general method 21 to afford crystals as a mixture of cis and trans 1/1 (16.4 g, 83.6%) and, after extraction of the eluent, also as a mixture of cis and trans 1/1 (1.91 g, 9.7%).

trans-(12-Bromo-7-chloro-2,3,4,14b-tetrahydro-4-oxo-1H-dibenzo[b,f]pyrido[1,2-d][1,4]oxazepin-1-yl)carbamic Acid 1-methylethyl Ester (Structure 33 of Scheme IX where X=O, R1=H, R2=H, R3=Cl, R4=H, R5=12-Br, R10=H, R22=CH(CH$_3$)$_2$)

To a solution of trans-12-bromo-7-chloro-2,3,4,14b-tetrahydro-4-oxo-1H-dibenzo[b,f]pyrido[1,2-d][1,4]oxazepine-1-carboxylic acid (18.3 g, 43.3 mmol) in toluene, triethylamine (10.8 mL, 77.9 mmol) and DPPA (12.2 mL, 56.3 mmol) were added. The reaction mixture was heated to reflux for 3 h. At 100° C., 2-propanol (6.6 mL, 86.5 mmol) was added and stirring was continued for 3 h at 110° C. The reaction mixture was poured into water, and extracted with ethyl acetate. The organic layer was washed with water and brine, dried (Na$_2$SO$_4$) and evaporated, which resulted in the crude title compound (25.4 g, 100%) as a mixture of isomers cis and trans 20:80. Data: (m/z)=479+481 (M+H)$^+$.

trans-(12-Bromo-7-chloro-2,3,4,14b-tetrahydro-1H-dibenzo[b,f]pyrido[1,2-d][1,4]oxazepin-1-yl)carbamic Acid 1-methylethyl Ester (Structure 34 of Scheme IX where X=O, R1=H, R2=H, R3=Cl, R4=H, R5=12-Br, R10=H, R22=CH(CH$_3$)$_2$)

Borane (1.0 M in THF, 216.5 mL, 216.5 mmol) was added dropwise to a stirred solution of trans-(12-bromo-7-chloro-2,3,4,14b-tetrahydro-4-oxo-1H-dibenzo[b,f]pyrido[1,2-d][1,4]oxazepin-1-yl)carbamic acid 1-methylethyl ester (25.4 g, 43.3 mmol) in THF. The resulting mixture was stirred at ambient temperature for 1 h. Water was added to the mixture until evolution of gas ceased. More water was added and the product was collected by filtration. The solid was dried at 40° C. under reduced pressure for 48 h to give crystals as a mixture of trans (86%) and cis (14%). The filtrate was extracted with CH$_2$Cl$_2$. The organic layer was washed with brine, dried (Na$_2$SO$_4$) and evaporated to give the crude product (9.5 g, 47.2%) as a mixture of isomers, cis/trans=1/2. CH$_2$Cl$_2$ was added to the crystals mentioned above and the pure trans isomer (5.9 g, 29.3%) was collected by filtration and dried under reduced pressure. The eluent was concentrated to give a mixture of cis and trans products (7.9 g, 39.2%). Data: (m/z)=465+467 (M+H)$^+$.

trans-12-Bromo-7-chloro-2,3,4,14b-tetrahydro-4-oxo-1H-dibenzo[b,f]pyrido[1,2-d][1,4]oxazepine-1-amine (Structure 35 of Scheme VIII where X=O, R1=H, R2=H, R3=Cl, R4=H, R5=12-Br, R10=H)

A mixture of acetic acid (30 mL) and hydrogen bromide (48%, 15 mL) was added to trans-(12-bromo-7-chloro-2,3,4,14b-tetrahydro-1H-dibenzo[b,f]pyrido[1,2-d][1,4]oxazepin-1-yl)carbamic acid 1-methylethyl ester (5.9 g, 12.7 mmol, pure trans isomer) and stirred for 1 h at 100° C. under nitrogen. After cooling down the product was collected by filtration and dissolved in CH$_2$Cl$_2$. The organic layer was washed with 2N NaOH (aq), sat. NaHCO$_3$ (aq), brine, dried (Na$_2$SO$_4$) and evaporated to give the title compound (4.0 g, 83%).

trans-N-(12-Bromo-7-chloro-2,3,4,14b-tetrahydro-1H-dibenzo[b,f]pyrido[1,2-d][1,4]oxazepin-1-yl)-2,2,2-trifluoroacetamide (Structure 55 of Scheme XIII)

This compound was prepared by general method 25 to afford the title compound (2.45 g, 90%). Data: $^1$H-NMR (400 MHz, DMSO) 1.6-1.86 (m, 4H), 2.1 (m, 1H), 3.12 (td, J=2.8, 13.4, 1H), 3.86 (d, J=14, 1H), 4.12 (d, J=10.4, 1H), 4.4 (m, 1H), 6.73-7.49 (6 ArH), 9.21 (d, J=10, 1NH). (m/z)=475+477 (M+H)$^+$.

Example 69 trans-7-Chloro-2,3,4,14b-tetrahydro-1-[(trifluoro-acetyl)amino]-1H-dibenzo[b,f]pyrido[1,2-d][1,4] oxazepine-12-carbonitrile (Structure 56 of Scheme XIV)

This compound was prepared by general method 27 to afford the title compound (4.7 mg, 3.5%). Data: $^1$H-NMR (400 MHz, DMSO) 1.60-1.88 (m, 4H), 2.03 (m, 1H), 3.14 (td, J=3.2, 13.2, 1H), 3.85 (d, J=13.6, 1H), 4.21 (d, J=10, 1H), 4.4 (m, 1H), 6.77-7.70 (7 ArH), 9.26 (d, J=9.6, 1 NH).

Example 70 trans-N-(7-Chloro-2,3,4,14b-tetrahydro12-methyl-1H-dibenzo[b,f]pyrido[1,2-d][1,4]oxazepin-1-yl)-2, 2,2-trifluoroacetamide (Structure 57 of Scheme XIV)

To a solution of trans-N-(12-bromo-7-chloro-2,3,4,14b-tetrahydro-1H-dibenzo[b,f]pyrido-[1,2-d][1,4]oxazepin-1-yl)-2,2,2-trifluoroacetamide (80 mg, 0.17 mmol) in THF (2 mL) was added ferrocene $PdCl_2$ (5 mg, 7 μmol), and the reaction mixture was stirred for 5 min. Methylzinc chloride was added dropwise whereafter the reaction mixture was heated to 60° C. and stirred overnight at 60° C. The mixture was poured into sat (aq) $NH_4Cl$ and extracted with ethyl acetate (3×). The combined organic layers were washed with brine, dried ($Na_2SO_4$) and evaporated. After purification on silica and with HPLC the title compound was obtained (13.2 mg, 19%). Data: $^1$H-NMR (400 MHz, DMSO) 1.60-1.85 (m, 3H), 2.0 (m, 1H), 2.23 (s, 3H), 3.11 (td, J=2.8, 13.2, 1H), 3.85 (d, J=14, 1H), 4.10 (d, J=10, 1H), 4.40 (m, 1H), 6.69-7.10 (6 ArH), 9.16 (d, J=10, 1H).

Example 71 trans-N-(12-Bromo-6,7-dichloro-2,3,4,14b-tetrahydro-1H-dibenzo[b,f]pyrido[1,2-d][1,4]oxazepin-1-yl)-2,2,2-trifluoroacetamide (Structure 58 of Scheme XIV)

To a suspension of trans-N-(12-bromo-7-chloro-2,3,4, 14b-tetrahydro-1H-dibenzo[b,f]pyrido[1,2-d][1,4]oxazepin-1-yl)-2,2,2-trifluoroacetamide (100 mg, 0.21 mmol) in acetone was added NCS (28.7 mg, 0.21 mmol) and 6N (aq) HCl (0.4 mL, 2.4 mmol). The resulting reaction mixture was stirred overnight. A second portion of NCS (28.7 mg, 0.21 mmol) was added and stirring was continued overnight. A further amount of NCS (28.7 mg, 0.21 mmol) was added and stirring was continued for 5 h. The reaction mixture was poured into sat. (aq) $NaHCO_3$ and extracted with ethyl acetate (2×). The combined organic layers were washed with brine, dried ($Na_2SO_4$) and evaporated. After purification of the crude product with HPLC three products were obtained: trans-N-(12-bromo-6,7-dichloro-2,3,4,14b-tetrahydro-1H-dibenzo[b,f]pyrido[1,2-d][1,4]oxazepin-1-yl)-2,2,2-trifluoroacetamide (structure 53 of scheme XIII) (13.9 mg, 13%), trans-N-(12-bromo-7,8-dichloro-2,3,4,14b-tetrahydro-1H-dibenzo[b,f]pyrido[1,2-d][1,4]oxazepin-1-yl)-2,2,2-trifluoroacetamide (15.7 mg, 14.1%) and trans-N-(12-bromo-6,7,8-trichloro-2,3,4,14b-tetrahydro-1H-dibenzo[b,f]pyrido[1,2-d][1,4]oxazepin-1-yl)-2,2,2-trifluoroacetamide (20.4 mg, 17.8%). Data (Structure 53): $^1$H-NMR (400 MHz, DMSO) 1.55 (m, 1H), 1.78 (m, 2H), 1.99 (m, 1H), 3.20 (t, J=12, 1H), 3.46 (d, J=14, 1H), 4.30 (d, J=8.8, 1H), 4.45 (br.s, 1H), 7.16-7.55 (6 ArH), 9.26 (d, J=6, 1NH).

Example 72 trans-N-(7-Chloro-11-fluoro-2,3,4,14b-tetrahydro-1H-dibenzo[b,f]pyrido[1,2-d][1,4]oxazepin-1-yl)-2, 2,2-trifluoroacetamide (Structure 61 of Scheme XV where R5=11-F, R10=H)

4-Bromo-2-[(2,3-difluorophenyl)methyleneamino]phenol (Structure 59 of Scheme XV where R5=3-F and R10=H)

2,3-Difluorobenzaldehyde (0.55 mL, 5 mmol) was added to a stirred solution of 5-chloro-2-hydroxyaniline (0.72 g, 5 mmol) in ethanol (5 mL). Within a few minutes a solid was formed and an additional amount of ethanol (10 mL) was added. The solid was isolated by filtration and dried to give the title compound (1.09 g, 81%).

8-Chloro-4-fluorodibenzo[b,f][1,4]oxazepine (Structure 60 from Scheme XV where R5=4-F, R10=H)

A solution of 4-bromo-2-[(2,3-difluorophenyl)methyleneamino]phenol (1.09 g, 4.1 mmol) in DMSO (2.4 mL) and diethylamine (1.2 mL) was heated in a microwave oven at 160° C. After 5 minutes the reaction mixture was allowed to cool and water was added. Filtration and drying gave the title compound (0.59 g, 57%).

trans-7-Chloro-11-fluoro-2,3,4,14b-tetrahydro-4-oxo-1H-dibenzo[b,f]pyrido[1,2-d][1,4]oxazepine-1-carboxylic Acid (Structure 32 of Scheme IX where X=O, R1=H, R2=H, R3=Cl, R4=H, R5=11-F, R10=H)

A solution of 8-chloro-4-fluorodibenzo[b,f][1,4]oxazepine (0.59 g, 2.4 mmol) and glutaric anhydride (0.36 g, 3.2 mmol) in xylene (1.3 mL) was stirred at 140° C. After 72 hours the reaction mixture was allowed to cool to room temperature and ether was added. Filtration gave a solid material. This solid was dissolved in ethyl acetate and extracted with aqueous 2N sodium hydroxide. 3 N Hydrochloric acid was added to the aqueous extract until pH 3 and subsequently extracted with ethyl acetate. The organic extract was washed with water and brine, dried ($Na_2SO_4$) and concentrated to give the title compound (0.44 g, 50%).

trans-(7-Chloro-11-fluoro-2,3,4,14b-tetrahydro-4-oxo-1H-dibenzo[b,f]pyrido[1,2-d][1,4]oxazepin-1-yl)carbamic Acid 1-methylethyl Ester (Structure 33 of Scheme IX where X=O, R1=H, R2=H, R3=Cl, R4=H, R5=11-F, R10=H, R22=CH(CH$_3$)$_2$)

General Method 22 was applied to trans-7-chloro-11-fluoro-2,3,4,14b-tetrahydro-4-oxo-1H-dibenzo[b,f]pyrido[1,2-d][1,4]oxazepine-1-carboxylic acid (0.44 g, 1.2 mmol) and using 2-propanol instead of 3-pentanol afforded trans-(7-chloro-11-fluoro-2,3,4,14b-tetrahydro-4-oxo-1H-dibenzo[b,f]pyrido[1,2-d][1,4]oxazepin-1-yl)carbamic acid 1-methylethyl ester (0.63 g, 82%).

trans-(7-Chloro-11-fluoro-2,3,4,14b-tetrahydro-1H-dibenzo[b,f]pyrido[1,2-d][1,4]oxazepin-1-yl)carbamic Acid 1-methylethyl Ester (Structure 34 of Scheme IX where X=O, R1=H, R2=H, R3=Cl, R4=H, R5=11-F, R10=H, R22=CH(CH$_3$)$_2$)

General method 23 was applied to trans-(7-chloro-11-fluoro-2,3,4,14b-tetrahydro-4-oxo-1H-dibenzo[b,f]pyrido[1,2-d][1,4]oxazepin-1-yl)carbamic acid 1-methylethyl ester (0.63 g, 0.98 mmol) to give the crude title compound. Purification by column chromatography on silica gel with heptanes/ethyl acetate=4/1 yielded the title compound (0.14 g, 35%).

trans-7-Chloro-11-fluoro-2,3,4,14b-tetrahydro-4-oxo-1H-dibenzo[b,f]pyrido[1,2-d][1,4]oxazepine-1-amine (Structure 35 of Scheme VIII where X=O, R1=H, R2=H. R3=Cl, R4=H, R5=11-F, R10=H)

General method 24 was applied to trans-(7-chloro-11-fluoro-2,3,4,14b-tetrahydro-1H-dibenzo[b,f]pyrido[1,2-d][1,4]oxazepin-1-yl)carbamic acid 1-methylethyl ester (0.14 g, 0.35 mmol) to give the crude title compound. Purification by column chromatography on silica gel with heptanes/ethyl acetate yielded trans-7-chloro-11-fluoro-2,3,4,14b-tetrahydro-4-oxo-1H-dibenzo[b,f]pyrido[1,2-d][1,4]oxazepine-1-amine (0.14 g, 35%).

trans-N-(7-Chloro-11-fluoro-2,3,4,14b-tetrahydro-1H-dibenzo[b,f]pyrido[1,2-d][1,4]oxazepin-1-yl)-2,2,2-trifluoroacetamide (Structure 61 of Scheme XV where R5=11-F and R10=H)

Preparation according to general method 25 using trans-7-chloro-11-fluoro-2,3,4,14b-tetrahydro-4-oxo-1H-dibenzo[b,f]pyrido[1,2-d][1,4]oxazepine-1-amine (94 mg, 0.29 mmol) delivered the crude title compound. This compound was purified by column chromatography on silica gel with heptanes/ethyl acetate followed by column chromatography on silica gel with toluene/ethyl acetate=9/1 to yield the title compound (58 mg, 48%). Data: $^1$H-NMR (400 MHz, DMSO d6) 1.60-1.92 (m, 3H), 1.99-2.07 (m, 1H), 3.10-3.18 (m, 1H), 3.90 (br.d, J=14, 1H), 4.19 (d, J=10 Hz, 1H), 4.39-4.49 (m, 1H), 6.75 (dd, J=3, 9, 1H), 6.98-7.11 (m, 4H), 7.20-7.27 (m, 1H), 9.22 (d, J=9, 1H).

Example 73 trans-N-(7-Chloro-14-fluoro-2,3,4,14b-tetrahydro-1H-dibenzo[b,f]pyrido[1,2-d][1,4]oxazepin-1-yl)-2,2,2-trifluoroacetamide (Structure 61 of Scheme XV where R5=14-F and R10=H)

Preparation according to the procedures described in Example 72 for trans-N-(7-chloro-11-fluoro-2,3,4,14b-tetrahydro-1H-dibenzo[b,f]pyrido[1,2-d][1,4]oxazepin-1-yl)-2,2,2-trifluoroacetamide starting from 2,6-difluorobenzaldehyde (0.54 mL, 5 mmol) delivered the crude title compound. This compound was purified by column chromatography on silica gel with heptanes/ethyl acetate, column chromatography on silica gel with toluene/ethyl acetate=9/1 and finally crystallization from acetonitrile to yield the title compound (136 mg, 6% overall yield). Data: $^1$H-NMR (400 MHz, DMSO d6) 1.57-1.76 (m, 2H), 1.89-2.04 (m, 2H), 3.09-3.18 (m, 1H), 3.93 (br.d, J=14, 1H), 4.42 (d, J=10, 1H), 4.52-4.62 (m, 1H), 6.74 (dd, J=9, 3, 1H), 6.95-7.16 (m, 4H), 7.27-7.33 (m, 1H), 9.30 (d, J=9, 1H).

Example 74 trans-N-(7-Chloro-12-fluoro-2,3,4,14b-tetrahydro-1H-dibenzo[b,f]pyrido[1,2-d][1,4]oxazepin-1-yl)-2,2,2-trifluoroacetamide (Structure 61 of Scheme XV where R5=12-F and R10=H)

Preparation according to the procedures described in Example 72 for trans-N-(7-chloro-11-fluoro-2,3,4,14b-tetrahydro-1H-dibenzo[b,f]pyrido[1,2-d][1,4]oxazepin-1-yl)-2,2,2-trifluoroacetamide starting from 2,4-difluorobenzaldehyde (0.55 mL, 5 mmol) delivered the crude title compound. This compound was purified by column chromatography on silica gel with heptanes/ethyl acetate and HPLC on a Luna column (10u C(18(2), 250×50 mm) using a gradient of acetonitrile/water to acetonitrile in 30 minutes at a flow of 50 mL/min. to yield the title compound (62 mg, 3% overall yield). Data: $^1$H-NMR (400 MHz, DMSO d6) 1.59-1.86 (m, 3H), 1.98-2.06 (m, 1H), 3.08-3.17 (m, 1H), 3.87 (br.d, J=13, 1H), 4.13 (d, J=10, 1H), 4.35-4.45 (m, 1H), 6.76 (dd, J=8, 3, 1H), 6.92-6.98 (m, 1H), 7.08 (s, 1H), 7.12-7.23 (m, 3H), 9.18 (d, J=9, 1H).

Example 75 trans-N-(7-Chloro-12,13-difluoro-2,3,4,14b-tetrahydro-1H-dibenzo[b,f]pyrido[1,2-d][1,4]oxazepin-1-yl)-2,2,2-trifluoroacetamide (Structure 61 of Scheme XV where R1=H, R2=H, R3=Cl, R4=H, R5=12-F, R10=13-F)

4-Bromo-2-[(2,4,5-trifluorophenyl)methyleneamino]phenol (Structure 59 of Scheme XV where where R5=4-F, R10=5-F)

2,4,5-Trifluorobenzaldehyde (0.56 mL, 5 mmol) was added to a stirred solution of 5-chloro-2-hydroxyaniline (0.72 g, 5 mmol) in ethanol (5 mL). Within minutes a solid was formed and an additional amount of ethanol (10 mL) was added. The solid was isolated by filtration and dried to give the desired product (1.17 g, 82%).

8-Chloro-2,3-difluorodibenzo[b,f][1,4]oxazepine (Structure 60 of Scheme XV where where R5=3-F, R10=2-F)

A solution of 4-bromo-2-[(2,4,5-trifluorophenyl)methyleneamino]Phenol (1.17 g, 4.1 mmol) in DMSO (2.4 mL) and N,N-diisopropylethylamine (1.2 mL) was heated in a microwave oven at 160° C. After 5 minutes the reaction mixture was allowed to cool and water was added. Filtration and drying gave the title compound (1.03 g, 95%).

trans-N-(7-Chloro-12,13-difluoro-2,3,4,14b-tetrahydro-1H-dibenzo[b,f]pyrido[1,2-d][1,4]oxazepin-1-yl)-2,2,2-trifluoroacetamide (Structure 61 of Scheme XV where R5=12-F and R10=13-F)

The procedure described in Example 72 for the preparation of trans-N-(7-Chloro-11-fluoro-2,3,4,14b-tetrahydro-1H-dibenzo[b,f]pyrido[1,2-d][1,4]oxazepin-1-yl)-2,2,2-trifluoroacetamide (Structure 61 of scheme XV where R5=11-F, R10=H) from intermediate 8-chloro-4-fluorodibenzo[b,f][1,4]oxazepine (Structure 60 of scheme XV) was applied to 8-chloro-2,3-difluorodibenzo[b,f][1.4]oxazepine (Structure 60 of scheme XV where R5=3-F and R10=2-F) (1.03 g, 3.87 mmol). The crude product was purified by column chromatography on silica gel with toluene/ethyl acetate=9/1 to give the title compound (44 mg, 3% overall yield). Data: $^1$H-NMR (400 MHz, CDCl$_3$): 1.66(dq, J=12, 4.5, 1H), 1.80-1.92(m, 2H), 2.28-2.34(m, 1H), 3.19(m, 1H), 3.86(m, 1H), 4.30(d, J=10, 1H), 4.66(m, 1H), 6.02(m, 1H), 6.59(m, 1H), 6.72(dd, J=8.8 3.2, 1H), 6.79(m, 1H), 6.90(d, J=3.2, 1H), 7.02(d, J=8, 1H).

Example 76 trans-N-(7-Chloro-1,2,3,4,10,14b-hexahydro-10-methyl-dibenzo[b,f]pyrido[1,2-d][1,4]diazepin-1-yl)-2,2,2-trifluoroacetamide (Structure 67 of scheme XVI)

4-Chloro-N-methyl-2-nitro-N-phenylphenylamine (Structure 62 of Scheme XVI)

4-Chloro-1-fluoro-2-nitrobenzene (20.0 g, 0.11 mol) and K$_2$CO$_3$ (15.7 g, 0.11 mol) were dissolved in N-methylaniline (37 mL, 0.34 mol) and subsequently heated to 180° C. After 5 h, the reaction mixture was cooled to room temperature, diluted with $CH_2Cl_2$ (750 mL) and washed with $H_2O$ (500 mL), aq. citric acid (5% 500 mL) and brine (500 mL). The organic layer was dried ($Na_2SO_4$) and concentrated under reduced pressure. The residual oil was chromatographed over silica (cyclohexane/$CH_2Cl_2$, 9/1, v/v) giving title compound containing ~30% starting material. The compound was subsequently stirred in cold hexane and the resulting red crystals were filtered resulting in pure crystalline product (16.5 g, 57% yield). Data: melting point: 59-62° C., Rf 0.65 (cyclohexane/ethyl acetate, 4/1, v/v).

4-Chloro-$N^1$-methyl-$N^1$-phenylbenzene-1,2-diamine (Structure 63 of Scheme XVI)

To a solution of 4-chloro-N-methyl-2-nitro-N-phenylphenylamine (12.5 g, 46.3 mmol) in ethanol (250 mL) was added $SnCl_2.2H_2O$ (37.5 gr., 0.17 mol). The solution was heated to 40° C. and stirred for 6 h. The reaction mixture was concentrated in vacuo and subsequently diluted with ethyl acetate (500 mL) and washed with H 20 (500 mL), a cooled (0° C.) aq. solution of NaOH (1 M, 200 mL), $H_2O$ (500 mL) and brine (500 mL). The organic layer was dried ($Na_2SO_4$), filtered and concentrated under reduced presssure. The crude compound was applied onto a silica column and eluted with heptane/ethyl acetate (8/2, v/v) affording the title compound (9.3 g, 87% yield). Data: Rf 0.65 (heptane/ethyl acetate, 7/3, v/v), (m/z)=233 $(M+H)^+$.

N-[5-chloro-2-(methylphenylamino)phenyl]formamide (Structure 64 of Scheme XVI)

4-Chloro-$N^1$-methyl-$N^1$-phenylbenzene-1,2-diamine (9.3 g, 40.1 mmol) was dissolved in formic acid (60 mL) and heated to reflux. After 2 h, the reaction mixture was concentrated in vacuo. The residue was dissolved in ethyl acetate (500 mL) and washed with aq. $NaHCO_3$ (5%, 500 mL). The organic layer was dried, filtered and concentrated under reduced pressure. The residual oil was chromatographed over silica (cyclohexane/$CH_2Cl_2$, 9/1, v/v) to give pure title compound (10.4 g, 100% yield). Data: Rf 0.25 (heptane/ethyl acetate, 3/1, v/v). (m/z)=261 $(M+H)^+$.

3-chloro-5-methyl-5H-dibenzo[b,f][1,4]diazepine (Structure 65 of Scheme XVI)

To a three-necked flask was added PPA (150 g), which was subsequently heated to 120° C. and vigorously stirred. $POCl_3$ was added dropwise over 90 minutes (caution: foaming) after which formamide (10.4 g, 40.1 mmol) was added to the reaction mixture in 4 consecutive portions. The reaction mixture was stirred for 2 h at 120° C. and then cooled to room temperature. aq. $NaHCO_3$ (300 mL) was cautiously added to the reaction mixture and the reaction mixture was neutralized by further additions of $NaHCO_3$ (s) until pH~8. Subsequently, ethyl acetate (1 L) was added and the salts were removed by filtration. The organic layer was washed with $H_2O$ (500 mL) and brine (500 mL), dried ($Na_2SO_4$), filtered and concentrated in vacuo. Purification by silica gel column chromatography (heptane/ethyl acetate, 8/2, v/v) afforded pure 3-chloro-5-methyl-5H-dibenzo[b,f][1,4]diazepine (8.8 g, 91% yield). (m/z)=243 $(M+H)^+$.

trans-7-Chloro-1,2,3,4,10,14b-hexahydro-10-methyl-4-oxodibenzo[b,f]pyrido[1,2-d][1,4]diazepine-1-carboxylic Acid (Structure 32 of Scheme IX, where X=N (Me), R1=H, R2=H, R3=Cl, R4=H, R5=H, R10=H)

A solution of 3-chloro-5-methyl-5H-dibenzo[b,f][1,4]diazepine (1.0 g, 4.1 mmol) and glutaric anhydride (0.64 g, 5.6 mmol) in xylene (2.5 mL) was stirred at 140° C. After 48 hours the reaction mixture was allowed to cool to room temperature and ether was added. Filtration gave the title compound (1.1 g, 72%) as a solid.

trans-(7-Chloro-1,2,3,4,10,14b-hexahydro-10-methyl-4-oxodibenzo[b,f]pyrido[1,2-d][1,4]diazepin-1-yl)carbamic Acid Methyl Ester (Structure 33 of Scheme IX, where X=N (Me), R1=H, R2=H, R3=Cl, R4=H, R5=H, R10=H, R22=$CH_3$)

General method 22 was applied to trans-7-chloro-1,2,3,4,10,14b-hexahydro-10-methyl-4-oxodibenzo[b,f]pyrido[1,2-d][1,4]diazepine-1-carboxylic acid (1.1 g, 3.0 mmol) and using methanol as alcohol afforded crude title compound (1.4 g, 100%) that was used in the next synthetic step without further purification.

trans-7-Chloro-1,2,3,4,10,14b-hexahydro-10-methyldibenzo[b,f]pyrido[1,2-d][1,4]diazepin-1-yl)carbamic Acid Methyl Ester (Structure 34 of Scheme IX, where X=N (Me), R1=H, R2=H, R3=Cl, R4=H, R5=H, R10=H, R22=$CH_3$)

General method 23 was applied to trans-7-chloro-1,2,3,4,10,14b-hexahydro-10-methyl-4-oxodibenzo[b,f]pyrido[1,2-d][1,4]diazepin-1-yl)carbamic Acid Methyl Ester (1.4 g, 100%) to give the crude title compound. This residue was triturated with ether to give the title compound (0.67 g, 61%) as a solid.

trans-7-Chloro-1,2,3,4,10,14b-hexahydro-10-methyldibenzo[b,f]pyrido[1,2-d][1,4]diazepine-1-amine (Structure 35 of Scheme IX, where X=N(Me), R1=H, R2=H, R3=Cl, R4=H, R5=H, R10=H)

General method 24 was applied to trans-7-chloro-1,2,3,4,10,14b-hexahydro-10-methyldibenzo[b,f]pyrido[1,2-d][1,4]diazepin-1-yl)carbamic acid methyl ester (0.67 g, 1.8 mmol) to give the crude title compound as a solution in ethyl acetate (100 mL). A solid material was formed upon storage at 5° C. for 16 hours. This solid was isolated (0.15 g, 21%) and the mother liquor was concentrated. The residue was treated with ether. The resulting solids were removed by filtration and the filtrate concentrated to give additional title compound (0.32 g, 56%). Both quantities of title compound were used in the next step without further purification.

trans-N-(7-Chloro-1,2,3,4,10,14b-hexahydro-10-methyldibenzo[b,f]pyrido[1,2-d][1,4]-diazepin-1-yl)-2,2,2-trifluoroacetamide (Structure 67 of Scheme XVI)

Preparation according to general method 25 using trans-7-chloro-1,2,3,4,10,14b-hexahydro-10-methyldibenzo[b,f]pyrido[1,2-d][1,4]diazepine-1-amine (0.25 g, 0.69 mmol) delivered the crude title compound. This residue was triturated with ether to give the title compound (0.17 g, 60%) as a solid. Data: $^1$H-NMR (400 MHz, $CDCl_3$) 1.62-1.89 (m, 3H), 2.27 (dq, J=5.0, 5.0, 12.4, 1H), 3.20 (m, 1H), 3.30 (s, 3H), 3.63 (m, 1H), 4.08 (m, 1H), 4.80 (m, 1H), 6.07 (br, 1NH), 6.71-7.27 (m, 7 ArH).

Example 77 trans-[(7-Chloro-1,2,3,4,10,14b-hexahydro-10-methyldibenzo[b,f]pyrido[1,2-d][1,4]diazepin-1-yl) amino]acetic Acid (Structure 69 of Scheme XVI)

Ethyl trans-[(7-chloro-1,2,3,4,10,14b-hexahydro-10-methyldibenzo[b,f]pyrido[1,2-d][1,4]diazepin-1-yl)amino]acetate (Structure 68 of Scheme XVI)

To a suspension of trans-7-chloro-1,2,3,4,10,14b-hexahydro-10-methyldibenzo[b,f]pyrido[1,2-d][1,4]-diazepin-1-ylamine (100 mg, 0.25 mmol) in DMF (2 mL) was added ethyl bromoacetate (56 μl, 0.51 mmol) and triethylamine (107 ul, 0.76 mmol). The resulting reaction mixture was heated to 60° C. and stirred for 5 h. The mixture was poured into water and extracted with ethyl acetate (3×). The organic layers were washed with sat (aq) NaHCO$_3$ and brine. After drying (MgSO$_4$), the solvents were removed under reduced pressure. The crude product was purified on silica with heptane/ethyl acetate 8:2 to afford 80 mg (80%) of the title compound.

trans-[(7-Chloro-1,2,3,4,10,14b-hexahydro-10-methyldibenzo[b,f]pyrido[1,2-d][1,4]diazepin-1-yl)amino]acetic Acid (Structure 69 of Scheme XVI)

To a solution of ethyl trans-[(7-chloro-1,2,3,4,10,14b-hexahydro-10-methyldibenzo[b,f]pyrido[1,2-d][1,4]diazepin-1-yl)amino]acetate (35 mg, 0.09 mmol) in dioxane (1 mL) was added 4N (aq) NaOH (250 ul). The reaction mixture was stirred at 65° C. for 1.5 h. It was diluted with water (25 mL) whereafter the pH was adjusted to pH 2 with 2N (aq) HCL. The mixture was extracted with ethyl acetate (2×), washed with water and brine, dried (MgSO$_4$) and evaporated. The crude product was purified with LC-MS to afford the title compound (4 mg, 12%). Data (m/z)=372 (M+H)$^+$.

Example 78 trans-N-(7-chloro-1,2,3,4,10,14b-hexahydrodibenzo [b,f]pyrido[1,2-d][1,4]diazepin-1-yl)-2,2,2-trifluoroacetamide (Structure 75 of Scheme XVII)

2-[(4-Chloro-2-nitrophenyl)amino]benzoic Acid (Structure 70 of Scheme XVII)

A solution of 4-chloro-1-fluoro-2-nitrobenzene (20 g, 114 mmol) and anthranilic acid (17.4 g, 127 mmol) in pentanol (250 mL) was heated to 120° C. in a Dean-Stark apparatus. Copper (126 mg, 2 mmol) was added, followed by potassium carbonate (12.7 g, 92 mmol). The resulting reaction mixture was stirred at 120° C. for 0.5 h and at 140° C. for 2 h. Subsequently, water and 1N (aq.) NaOH were added to dissolve the product. Then, the pH was adjusted to pH 5 and the water layer was extracted with ethyl acetate (3×). The combined organic layers were washed with water and brine, dried and evaporated. Ethanol was added to the obtained product. The title compound (14.4 g, 43%) was collected by filtration of the ethanol mixture.

2-[(2-Amino-4-chlorophenyl)amino]benzoic Acid (Structure 71 of Scheme XVI)

To a solution of 2-[(4-chloro-2-nitrophenyl)amino]benzoic acid (12.8 g, 43.7 mmol) in ethyl acetate (300 mL) was added platinum on sulfide coal 5%. The reaction mixture was hydrogenated at 2 bar for 5 h. After filtration through dicalite, washing with ethyl acetate and removal of the solvent under reduced pressure the title compound (11.8 g, 100%) was obtained.

8-Chloro-5,10-dihydrodibenzo[b,f][1,4]diazepin-11-one (Structure 72 of Scheme XVII)

A solution of 2-[(2-amino-4-chlorophenyl)amino]benzoic acid (11.8 g, 45 mmol) in xylene (150 mL) was heated to reflux in a Dean-Stark apparatus. The reaction mixture was stirred at reflux temperature for 31 h. After removal of the xylene in vacuo, the title compound was obtained. There was still starting material present. Therefore the product was dissolved in xylene (150 mL) again and stirring was continued overnight at reflux temperature in a Dean-Stark apparatus. After removal of the xylene under reduced pressure the title compound (12.4 g, 50.6 mmol) was obtained.

8-Chloro-10,11-dihydro-5H-dibenzo[b,f][1,4]diazepine (Structure 73 of Scheme XVII)

THF (250 mL) was cooled to 0° C. whereafter LiAlH$_4$ (6.7 g, 177 mmol) was added portionwise. Subsequently, 8-chloro-5,10-dihydrodibenzo[b,f][1,4]diazepin-11-one (12.4 g, 45 mmol) was added portionwise followed by THF (100 mL). The resulting reaction mixture was heated to reflux and stirred overnight at reflux temperature. After cooling down the mixture to 0° C., sat. (aq) Na$_2$SO$_4$ was added dropwise. Stirring was continued for 15 minutes, whereafter the reaction mixture was filtrated through dicalite. The volatiles were removed under reduced pressure to afford the crude product. A mixture of toluene and ethyl acetate was added to the crude product. The solid material (5.4 g, 52%) was collected through flitration, followed by drying overnight at 40° C. under reduced pressure.

8-Chloro-5H-dibenzo[b,f][1,4]diazepine (Structure 74 of Scheme XVII)

To a solution of 8-chloro-10,11-dihydro-5H-dibenzo[b,f] [1,4]diazepine (8.75 g, 37.9 mmol) in CH$_2$Cl$_2$ (375 mL) was added MnO$_2$ (14.5 g, 166 mmol). The reaction mixture was stirred at room temperature for 1.5 h. After filtration through dicalite, washing with CH$_2$Cl$_2$, the volatiles were removed in vacuo. The crude product was dissolved in ethanol (250 mL) wherafter 2N (aq) NaOH (20 mL) was added. This mixture was stirred at room temperature for 2.5 h. The reaction mixture was filtrated through dicalite and washed with CH$_2$Cl$_2$. After removal of the solvent under reduced pressure, the residu was dissolved in ethanol (350 mL). NaOH (2N, 20 mL) was added and the mixture was stirred for 3 h. Water was added and the mixture was extracted with ethyl acetate (3×). The combined organic layers were washed with brine, dried and evaporated to afford the title compound (8.9 g, 38.9 mmol).

trans-7-Chloro-1,2,3,4,10,14b-hexahydro-4-oxodibenzo[b, f]pyrido[1,2-d][1,4]diazepine-1-carboxylic Acid (Structure 32 of Scheme IX where X=N(H), R1=H, R2=H, R3=Cl, R4=H, R5=H, R10=H)

This compound was prepared by general method 21, after acid/base extraction of the reaction mixture to afford the crude title compound (4.4 g, 34%).

trans-7-Chloro-1,2,3,4,10,14b-hexahydro-4-oxodibenzo[b, f]pyrido[1,2-d][1,4]diazepin-1-yl)carbamic Acid Methyl Ester (Structure 33 of Scheme IX where X=N(H), R1=H, R2=H, R3=Cl, R4=H, R5=H, R10=H, R22=CH$_3$)

This compound was prepared by general method 22. Methanol was used as alcohol to afford the crude title compound (437 mg, >100%).

trans-7-Chloro-1,2,3,4,10,14b-hexahydrodibenzo[b,f]pyrido[1,2-d][1,4]diazepin-1-yl)carbamic Acid Methyl Ester (Structure 34 of Scheme IX where X=N(H), R1=H, R2=H, R3=Cl, R4=H, R5=H, R10=H, R22=CH$_3$)

This compound was prepared by general method 23 to afford the crude title compound (0.51 g, 100%).

trans-7-Chloro-1,2,3,4,10,14b-hexahydrodibenzo[b,f]pyrido[1,2-d][1,4]diazepine-1-amine (Structure 35 of Scheme IX where X=N(H), R1=H, R2=H, R3=Cl, R4=H, R5=H, R10=H)

To a solution of trans-7-chloro-1,2,3,4,10,14b-hexahydrodibenzo[b,f]pyrido[1,2-d][1,4]diazepin-1-yl)carbamic acid methyl ester (0.51 g, 0.95 mmol) in ethylene glycol (6 mL) was added KOH (0.37 g, 6.6 mmol). The reaction mixture was heated to 100° C. and stirred overnight at 140° C. After cooling of the reaction mixture water and ethyl acetate were added. The mixture was extracted with ethyl acetate (3×). The organic layers were washed with water and brine, dried (Na$_2$SO$_4$) and evaporated to give the crude product (350 mg, 100%).

trans-N-(7-Chloro-1,2,3,4,10,14b-hexahydrodibenzo[b,f]pyrido[1,2-d][1,4]diazepin-1-yl)-2,2,2-trifluoroacetamide (Structure 75 of Scheme XVII)

To a solution of trans-7-chloro-1,2,3,4,10,14b-hexahydrodibenzo[b,f]pyrido[1,2-d][1,4]diazepine-1-amine (Structure 35 of scheme IX where X=N(H), R1=H, R2=H, R3=Cl, R4=H, R5=H, R10=H) (350 mg, 1.17 mmol) in methanol (22 mL) and triethylamine (0.7 mL) was added ethyl trifluoroacetate (1.5 mL). The reaction mixture was stirred at room temperature for 3 h. Water was added and the mixture was extracted with ethyl acetate (3×). The organic layers were washed with brine, dried (Na$_2$SO$_4$) and evaporated. After purification on silica with heptane/ethyl acetate 6:4 the title compound (90 mg, 19%) was obtained. Data: $^1$H-NMR (400 MHz, CDCl$_3$) 1.69 (m, 1H), 1.86-1.94 (m, 2H), 2.11 (m, 1H), 2.99-3.09 (m, 2H), 4.47 (d, 1H), 4.86 (m, 1H), 5.79 (s, 1H, NH), 6.62 (d, J=8.2, 1H), 6.75 (dd, J=7.8, 1H), 6.89 (t, J=7.8, 1H), 6.91 (dd, J=8.2, J=2.7, 1H), 7.10 (d, J=2.7, 1H), 7.18 (t, J=7.8, 1H), 7.24 (d, J=7.8, 1H).

Examples 79A and B (1α,2β,14bα)-N-(7-Chloro-2,3,4,14b-tetrahydro-2-methyl-1H-dibenzo[b,f]pyrido[1,2-d][1,4]oxazepin-1-yl)-2,2,2-trifluoroacetamide (Structure 86 of Scheme XVIII)

(1α,2α,14bα)-N-(7-Chloro-2,3,4,14b-tetrahydro-2-methyl-1H-dibenzo[b,f]pyrido[1,2-d][1,4]oxazepin-1-yl)-2,2,2-trifluoroacetamide (Structure 87 of Scheme XVIII)

N-(5-Chloro-2-phenoxyphenyl)formamide (Structure 76 of Scheme XVIII)

This compound was generated by general method 29 from 5-chloro-2-phenoxybenzeneamine to afford N-(5-chloro-2-phenoxyphenyl)formamide (29.5 g, 94%). (m/z)=248 (M+H)$^+$.

8-Chlorodibenzo[b,f][1,4]oxazepine (Structure 77 of Scheme XVIII)

This compound was generated by general method 30 to afford 8-Chlorodibenzo[b,f][1,4]oxazepine (24.5 g, 89%). (m/z)=230 (M+H)$^+$.

trans-7-Chloro-2-methyl-2,3,4,14b-tetrahydro-4-oxo-1H-dibenzo[b,f]pyrido[1,2-d][1,4]oxazepine-1-carboxylic Acid (Structure 78 of Scheme XVIII)

This compound was generated by general method 21 by using 3-methylglutaric anhydride (4). A mixture of two isomers (1/1) (2.2 g, 66%) was obtained by crystallisation from diethyl ether. (m/z)=358 (M+H)$^+$.

trans-(7-Chloro-2-methyl-2,3,4,14b-tetrahydro-4-oxo-1H-dibenzo[b,f]pyrido[1,2-d][1,4]oxazepin-1-yl)carbamic Acid Methyl Ester (Structure 79 of Scheme XVIII)

This compound was generated by general method 22 by using methanol as alcohol to afford the crude title compound (2.6 g, >100%). (m/z)=387 (M+H)$^+$.

trans-(7-Chloro-2-methyl-2,3,4,14b-tetrahydro-1H-dibenzo[b,f]pyrido[1,2-d][1,4]oxazepin-1-yl)carbamic Acid Methyl Ester (Structures 80, 81 and 82 of Scheme XVIII)

This compound was generated by general method 23. The crude product was chromatographed with heptane/ethyl acetate 6:4 to afford (1α,2β,14bα)-(7-chloro-2-methyl-2,3,4,14b-tetrahydro-1H-dibenzo[b,f]pyrido[1,2-d][1,4]oxazepin-1-yl)carbamic acid methyl ester (Structure 82 of scheme XVII) (301 mg, 11%, trans) and a mixture of two other isomers (1α,2α,14bα)-(7-chloro-2-methyl-2,3,4,14b-tetrahydro-1H-dibenzo[b,f]pyrido[1,2-d][1,4]oxazepin-1-yl) carbamic acid methyl ester (Structure 80 of scheme XVIII) and (1α,2α,14bβ)-(7-chloro-2-methyl-2,3,4,14b-tetrahydro-1H-dibenzo[b,f]pyrido[1,2-d][1,4]oxazepin-1-yl)carbamic acid methyl ester (Structure 81 of scheme XVIII) (1.6 g, 63%, trans and cis). (m/z)=373 (M+H)$^+$.

trans-7-Chloro-2-methyl-2,3,4,14b-tetrahydro-1H-dibenzo[b,f]pyrido[1,2-d][1,4]oxazepine-1-amine (Structures 83 and 84 of Scheme XVIII This compound was generated by general method 24 starting with a mixture of (1α,2α,14bα)-(7-chloro-2-methyl-2,3,4,14b-tetrahydro-1H-dibenzo[b,f]pyrido[1,2-d][1,4]oxazepin-1-yl)carbamic acid methyl ester (Structure 80 of scheme XVII) and (1α,2α,14bβ)-(7-chloro-2-methyl-2,3,4,14b-tetrahydro-1H-dibenzo[b,f]pyrido[1,2-d][1,4]oxazepin-1-yl)carbamic acid methyl ester (Structure 81 of scheme XVII) to afford a mixture of two isomers (1α,2α,14bα)-7-chloro-2-methyl-2,3,4,14b-tetrahydro-1H-dibenzo[b,f]pyrido[1,2-d][1,4]oxazepine-1-amine (Structure 83 of scheme XVII) and (1α,2α,14bβ)-7-chloro-2-methyl-2,3,4,14b-tetrahydro-1H-dibenzo[b,f]pyrido[1,2-d][1,4]oxazepine-1-amine (Structure 84 of scheme XVII) (1.3 g, 96%).

(1α,2β,14bα)-7-chloro-2-methyl-2,3,4,14b-tetrahydro-1H-dibenzo[b,f]pyrido[1,2-d][1,4]oxazepine-1-amine (Structure 85 of Scheme XVII)

This compound was generated from (1α,2β,14bα)-(7-chloro-2-methyl-2,3,4,14b-tetrahydro-1H-dibenzo[b,f]pyrido[1,2-d][1,4]oxazepin-1-yl)carbamic acid methyl ester by general method 24 to afford the title compound (Structure 85 from scheme XVII) (130 mg, 51%, trans).

(1α,2β,14bα)-N-(7-Chloro-2,3,4,14b-tetrahydro-2-methyl-1H-dibenzo[b,f]pyrido[1,2-d][1,4]oxazepin-1-yl)-2,2,2-trifluoroacetamide (Structure 86 from Scheme XVII)

This compound was generated by general method 25 starting from compound 85 to afford the title compound. After purification with HPLC (53 mg, 31%, trans) was obtained. Data: $^1$H-NMR (400 MHz, CDCl$_3$) 1.02-1.04 (d, J=6.4, 3H), 1.58 (m, 1H), 1.78 (m, 1H), 1.98 (m, 1H), 3.22-3.31 (td, J=12.2, J=2.2, 1H), 3.91 (m, 1H), 4.13-4.18 (d, J=10.0, 1H), 4.23-4.30 (t, J=10.0, 1H), 6.64-7.27 (7 ArH). (m/z)=411 (M+H)$^+$.

(1α,2α,14bα)-N-(7-Chloro-2,3,4,14b-tetrahydro-2-methyl-1H-dibenzo[b,f]pyrido[1,2-d][1,4]oxazepin-1-yl)-2,2,2-trifluoroacetamide (Structure 87 from Scheme XVII)

This compound was generated by general method 25 starting with a mixture of isomers 83 and 84 to afford a mixture of products 87 and 88. After purification with HPLC the title compound (115 mg, 13%) was obtained. Data: $^1$H-NMR (400 MHz, DMSO) 1.00-1.04 (d, J=7.0, 3H), 1.73-1.79 (q, J=6.0, 2H), 2.24-2.35 (m, 1H), 3.31-3.52 (m, 2H), 4.55-4.60 (d, J=8.3, 1H), 4.65-4.72 (m, 1H), 6.71-7.38 (7 ArH), 9.07-9.12 (d, J=9.8, NH). (m/z)=411 (M+H)$^+$.

Example 80

Progesterone Receptor-B Activity in a Transactivation.

The (anti-)progestagenic activity of a compound of the invention (EC 50 and intrinsic activity) was determined in an in vitro bioassay of Chinese hamster ovary (CHO) cells stably transfected with the human progesterone receptor-B expression plasmid and with a reporter plasmid in which the MMTV-promoter is linked to the luciferase reporter gene. The cell-line is known under the name CHO-PRB-pMMTV-LUC 1E2-A2 (Dijkema R et al (1998) J Steroid Biochem Mol Biol, 64:147-56). The cells were cultured with charcoal-treated supplemented defined bovine calf serum from Hyclone (Utah, USA) in Dulbecco's Modified Eagles Medium/Nutrient Mixture F-12 (DMEM/HAM F12 in ratio 1:1) from Gibco (Paisley, UK).

The antiprogestagenic activity of a compound of the invention was determined by the inhibition of the transactivation via the progesterone receptor-B of the enzyme luciferase in the presence of 1 nM (16α)-16-ethyl-21-hydroxy-19-norpregn-4-ene-3,20-dione and compared with the reference antiprogestagen (6β,11β,17β)-11-[4-(dimethylamino)phenyl]-4',5'-dihydro-6-methylspiro[estra-4,9-diene-17,2'(3'H)-furan]-3-one, the activity of which was set at 100%. Agonistic ligands do not inhibit transactivation of luciferase activity induced by 0.1 nM Org 2058, whereas strong and weak antiprogestagens can inhibit transactivation dependent on the dose level used.

Progestagenic activity with an $EC_{50}$ between 10000 and 100 nM was found for the compounds of Examples 1, 3, 5, 9, 10, 12, 14, 15, 16, 17, 18, 27, 28, 30, 31, 36, 37, 39, 40, 42B, 43, 44, 48, 49, 50, 56, 64 and 67. The compounds of Examples 11, 13, 21, 24, 29, 38A, 45, 46, 55, 62, 68, 69, 70, 72, 74, 78 and 79B showed an $EC_{50}$ between 100 and 10 nm, whereas the compounds of Examples 6, 7, 8, 13 (1S14bR isomer), 19, 20, 22, 23, 25, 26, 38B, 41, 42A, 47, 51, 52, 53, 54, 57, 58, 59, 60, 61, 63, 71, 73, 75, 76 and 79A showed an $EC_{50}$<10 nM. The intrinsic activity relative to (16α)-16-ethyl-21-hydroxy-19-norpregn-4-ene-3,20-dione was >10% in all compounds tested.

Anti-progestagenic activity with an $EC_{50}$ between 10000 and 100 nM was found for the compounds of Examples 5, 9, 10, 15, 21, 32, 33, 35, 38A, 39 and 41. The compounds of Examples 7, 8, 11, 22 (1S,14bR isomer), 29, 48 and 49 showed an $EC_{50}$ between 100 and 10 nm, whereas the compound of Example 13 (1S,14bR isomer) showed an $EC_{50}$<10 nM. The intrinsic activity relative to (6β,11β,17β)-11-[4-(dimethylamino)phenyl]-4',5'-dihydro-6-methylspiro[estra-4,9-diene-17,2'(3'H)-furan]-3-one was >15% in all compounds tested.

The invention claimed is:

1. A compound according to Formula I, or a pharmaceutically acceptable salt thereof wherein R1, R3, R4, R5 and R10 independently are selected from the group consisting of H, halogen, (1-4C)alkyl, (2-4C)alkenyl, (2-4C)alkynyl, OH, CN, O(1-4C)alkyl, $S(O)_m$(1-4C)alkyl, optionally substituted with one or more halogen atoms, C(O)(1-4C)alkyl, OC(O)(1-4C)alkyl and NR19R20, R2 is selected from the group consisting of H, halogen, $NO_2$, NR11R12, (1-4C)alkyl, (2-4C)alkenyl, (2-4C)alkynyl, OH, O(1-4C)alkyl, S(1-4C)alkyl and OC(O)(1-4C)alkyl, R6 is selected from the group consisting of H, C(Y)R15, C(O)OR16, C(S)NR17, (1-6C)alkyl, (1-6C)alkoxy-substituted (1-4C)alkyl and $(CH_2)_n$C(O)OR21, R7 is H or R7 is selected from the group consisting of (1-4C)alkyl, (2-4C)alkenyl and (2-4C)alkynyl, all optionally substituted with one or more halogen atoms, R8 and R9 independently are selected from the group consisting of H and (1-4C)alkyl, R11 and R12 independently are selected from the group consisting of H, (1-4C)alkyl, (2-4C)alkenyl, (2-4C)alkynyl, (1-6C)alkoxycarbonyl, (1-4C)alkylsulfonyl, and (6-10C)arylsulfonyl, R15 is H or R15 is selected from the group consisting of (1-6C)alkyl, (3-6C)cycloalkyl, (2-4C)alkenyl or (2-4C)alkynyl, (6-10C)aryl, 1,4-bisaryl, amino(1-4C)alkyl, hydroxyl(1-4C)alkyl, and carboxy(1-4C)alkyl, all optionally substituted with one or more halogen atoms, R16 is (1-6C)alkyl, optionally substituted with one or more halogen atoms, R17 is selected from the group consisting of (1-4C)alkyl, (2-4C)alkenyl, (2-4C)alkynyl and (3-6C) cycloalkyl, all optionally substituted with one or more halogen atoms, X is O, Y is selected from the group consisting of O, S, and NH, R18 is selected from the group consisting of H and (1-4C)alkyl, R19 is selected from the group consisting of H and (1-4C)alkyl, R20 is selected from the group consisting of H, (1-4C)alkyl, $CH_2$(6-10C)aryl, C(O)(1-6C)alkyl and C(O)NH(1-4C)alkyl, R21 is selected from the group consisting of H and (1-6C)alkyl, m is 0, 1 or 2, and n is 1, 2 or 3, provided that (i) when R1, R2, R3, R4, and R5 are H, R8, R9 and R10 are H, and R6 is ethyl or $C(O)CH_3$ then R7 is not H;

(ii) when R1, R2, R3, R4, and R5 are H, R8, R9 and R10 are H, and R6 is methyl then R7 is not methyl; and (iii) when R1, R2, R3, R4, and R5 are H, R8, R9 and R10 are H, and R6 is H then R7 is not H or ethyl.

2. The compound according to claim 1, wherein R2 is selected from the group consisting of H, halogen, $NO_2$, and NR11R12; and R11 and R12 independently are selected from the group consisting of H, (1-6C)alkoxycarbonyl, (1-4C)alkylsulfonyl and (6-10C)arylsulfonyl.

3. The compound according to claim 1, wherein R1 and R5 are H and R3 and R4 are selected from H or halogen.

4. The compound according to claim 1, wherein

R6 is selected from H or C(Y)R15 and

R15 is (1-4C)alkyl optionally substituted with one or more halogen atoms or H.

5. The compound according to claim 1, wherein

R2 is selected from the group consisting of H, halogen and NO$_2$; and

R15 is (1-2C)alkyl optionally substituted with one or more halogen atoms.

6. The compounds according to claim 1, wherein

R11 is H and R12 is selected from the group consisting of (1-6C)alkoxycarbonyl, (1-4C) alkylsulfonyl and (6-10C)arylsulfonyl.

7. The compound according to claim 1, wherein

R2 is H,

R3 is halogen,

R15 is methyl, optionally substituted with 1-3 halogen atoms and

Y is O or S.

8. The compound according to claim 1, wherein R4 is H and X is O.

9. The compound according to claim 1, wherein R2 is H or halogen,

R3 and/or R4 are independently selected from the group consisting of H, CN, halogen, (2-4C)alkenyl and C(O)(1-4C)alkyl, and R5 and/or R10 are independently selected from H or halogen.

10. The compound according to claim 1, wherein R8 and R9 are H.

11. The compound according to claim 9, wherein R6 is H or C(Y)R15 and

R15 is (1-4C)alkyl, optionally substituted with one or more halogen atoms, or H.

12. The compound according to claim 11, wherein Y is O or S, and

R15 is methyl, optionally substituted with one or more halogen atoms.

13. A pharmaceutical composition, comprising:

the compound according to claim 1 or a pharmaceutically acceptable salt thereof and pharmaceutically acceptable auxiliaries.

* * * * *